United States Patent
Cheung et al.

(10) Patent No.: US 8,471,027 B2
(45) Date of Patent: Jun. 25, 2013

(54) ADAMANTYL COMPOUNDS

(75) Inventors: Adrian Wai-Hing Cheung, Glen Rock, NJ (US); Kevin Richard Guertin, Verona, NJ (US); Nancy-Ellen Haynes, Cranford, NJ (US); Eric Mertz, Fair Lawn, NJ (US); Lida Qi, Killingworth, CT (US); Yimin Qian, Wayne, NJ (US); Nathan Robert Scott, Livingston, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/437,984

(22) Filed: Apr. 3, 2012

(65) Prior Publication Data

US 2012/0258982 A1   Oct. 11, 2012

Related U.S. Application Data

(60) Provisional application No. 61/472,220, filed on Apr. 6, 2011.

(51) Int. Cl.
*C07D 215/233* (2006.01)
*C07D 471/04* (2006.01)

(52) U.S. Cl.
USPC .......................................... 546/123; 546/156

(58) Field of Classification Search
None
See application file for complete search history.

(56) References Cited

FOREIGN PATENT DOCUMENTS

| WO | 2005/097800 | 10/2005 |
|----|-------------|---------|
| WO | 2006/024627 | 3/2006 |
| WO | 2007/107470 | 9/2007 |
| WO | 2008/041075 | 4/2008 |
| WO | 2008/138920 | 11/2008 |
| WO | 2009/015917 | 2/2009 |

OTHER PUBLICATIONS (Intl Search Report for PCT/EP2012/056122 May 22, 2012).
Jirgensons et al., Synthesis 12:1709-1712 ( 2000).
Mendelson et al., Synthetic Comm. 26(3):603-610 ( 1996).
Calet et al., J. Am. Chem. Soc. 111:931-934 ( 1989).
Gauuan et al., Bioorganic & Medicinal Chemistry 10:3013-3021 ( 2002).
Yin et al., Organic Letters 4(20):3481-3484 ( 2002).
Adediran et al., Bioorganic & Medicinal Chemistry 9:1175-1183 ( 2001).

*Primary Examiner* — Janet Andres
*Assistant Examiner* — Timothy R Rozof

(57) ABSTRACT

The invention relates to JNK inhibitors and corresponding methods, formulations, and compositions for inhibiting JNK and treating JNK-mediated disorders. The application discloses JNK inhibitors, as described below in Formula I:

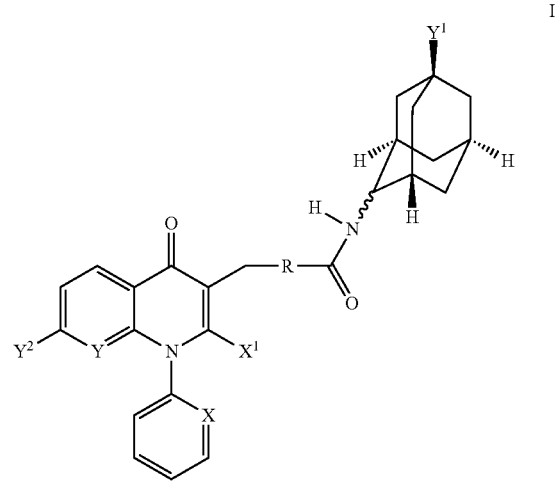

wherein the variables are as defined herein. The compounds and compositions disclosed herein are useful to modulate the activity of JNK and treat diseases associated with JNK activity. Disclosed are methods and formulations for inhibiting JNK and treating JNK-mediated disorders, and the like, with the compounds, and processes for making said compounds, and corresponding compositions, disclosed herein.

15 Claims, No Drawings

ADAMANTYL COMPOUNDS

PRIORITY TO RELATED APPLICATIONS

This application claims the benefit of U.S. Provisional Patent Application No. 61/472,220, filed on Apr. 6, 2011, which is hereby incorporated by reference in its entirety.

FIELD OF THE INVENTION

The c-Jun N-terminal kinases (JNKs) are members of mitogen-activated protein kinase family along with p38 and extracellular signal-regulated kinases (ERKs). Three distinct genes (jnk1, jnk2 and jnk3) encoding 10 splice variants have been identified. JNK1 and JNK2 are expressed in a wide variety of tissues, whereas JNK3 is mainly expressed in neurons, and to a lesser extent in heart and testes. Members of JNK family are activated by pro-inflammatory cytokines such as tumor necrosis factor α (TNF-α) and interleukin-1β(IL-1β), as well as environmental stresses. The activation of JNKs is mediated by its upstream kinases, MKK4 and MKK7, via dual phosphorylation of Thr-183 and Tyr-185. It has been shown that MKK4 and MKK7 can be activated by the diverse upstream kinases, including MEKK1 and MEKK4, depending upon the external stimuli and cellular context. The specificity of JNK signaling is achieved by forming a JNK-specific signaling complex containing multiple components of the kinase cascade by use of scaffold proteins called JNK-interacting proteins. JNKs have been shown to play important roles in inflammation, T cell functions, apoptosis and cellular survival by phosphorylating specific substrates, including transcription factors such as c-Jun, the component of activator protein-1 (AP1) family, and ATF2, as well as non-transcription factors such as IRS-1 and Bcl-2. Over-activation of JNK is believed to be an important mechanism in autoimmune, inflammatory, metabolic, neurological diseases as well as cancer.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients and rodent arthritic joints from animal models of arthritis. In addition, inhibition of JNK activation by selective JNK inhibitors blocked proinflammatory cytokines and MMP production in human synoviocytes, macrophages and lymphocytes. Importantly, administration of the selective JNK inhibitors in rats with adjuvant arthritis or in mice with collagen-induced arthritis effectively protected joints from destruction and significantly reduced paw swelling by inhibiting cytokine and collagenase expression.

Asthma is a chronic inflammatory disease of airways, characterized by the presence of a cellular inflammatory process and by bronchial hyper-responsiveness associated with structural changes of the airways. This disorder has been shown to be driven by many cell types in the airways, including T lymphocytes, eosinophils, mast cells, neutrophils and epithelial cells. JNKs have emerged as promising therapeutic targets for asthma based upon the recent proof-of-concept studies: it has been shown that JNK inhibitors significantly blocked RANTES production in activated human airway smooth cells. More importantly, the JNK inhibitors showed good efficacy in chronic rat and mouse models for their abilities to reduce cellular infiltration, inflammation, hyper-responsiveness, smooth muscle proliferation, and IgE production. These observations suggest important roles of JNKs in the allergic inflammation and airway remodeling process associated with hyper-responsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions. Activation of the JNK pathway by pro-inflammatory cytokines and oxidative stresses negatively regulates insulin signaling via phosphorylation of insulin receptor substrate-1 (IRS-1) at $Ser^{307}$, therefore contributes to insulin resistance and glucose tolerance. Compelling genetic evidence came from elegant animal model studies using $jnk^{-/-}$ mice crossed with either genetic (ob/ob) obese mice or dietary obese mice. Loss of JNK1($JNK1^{-/-}$), but not JNK2 functions ($jnk2^{-/-}$), protected obese mice from body gains, increased steady-state levels of blood glucose, and decreased plasma insulin levels. These studies demonstrated the potential utility of JNK inhibitor in the treatment of obesity/type 2 diabetes.

Neurodegenerative diseases, such as Alzheimer's (AD), Parkinson's (PD) and Stroke are CNS diseases characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli. Over-activation of JNK was observed in human brains from AD patients or rodent brain sections derived from animal models of neurodegenerative diseases. For example, increased phospho-JNKs were detected in the post-mortem brains from the AD patients. Administration of JNK inhibitory peptide (JIP-1 peptide) in the rodent model of AD induced by β-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra. In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death. These data suggest JNK3 was mainly responsible for glutamate excitotoxicity, an important component in ischemic conditions. Taken together, data has emerged suggesting JNKs as attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to AP1 activation has recently been implicated to contribute to the cellular survival of specific cancer types such as glial tumors and BCL-ABL transformed B lymphoblasts. In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML (acute myeloid leukemia) patients has been causally linked to the sustained JNK activity present in these AML samples. Activation of JNK in leukemic cells resulted in induced expression of efflux pumps such as mdr1 and MRP1 responsible for multidrug resistance. Also, genes with a survival benefit in response to oxidative stress including glutathione-S-transferase π and γ-glutamyl cysteine synthase were also upregulated by the activated JNK pathway.

Kidney diseases are characterized by loss of nephron function caused by progressive glomerulosclerosis and tubulointerstitial fibrosis. Renal disease may develop as a consequence of many conditions including inflammation, hypertension, diabetes, or acute tissue damage caused by antibiotics, contrast agents, or other nephrotoxic substances. JNK signaling has been shown to be upregulated in pathology specimens from many human renal diseases, including immune and non-immune mediated glomerulonephritis, diabetic nephropathy, hypertension, acute injury, and appears to play a signaling role in polycystic kidney disease. Compelling evidence for a central role of JNK and the therapeutic potential of JNK inhibitors is supported by studies in animal models of renal injury. JNK was increased in a rat anti-glomerular basement membrane induced glomerulonephritis model and renal function was improved by a specific inhibitor in both acute and chronic disease paradigms. JNK was also increased in the Dahl salt-sensitive hypertensive rat, a model of hypertensive renal disease, as well as in models of renal ischemia-reperfusion injury. The cellular mechanisms by which JNK may contribute to renal injury are, in part, by up-regulation of pro-inflammatory mediators in macrophages, as well as by activation of pro-fibrotic, and pro-apoptotic pathways directly in cells of the renal glomerulus and the tubular epithelium. The ability to improve renal function by inhibition of JNK in multiple disease models, suggests JNKs as attractive targets for therapy of renal diseases of various etiology.

SUMMARY OF THE INVENTION

In one aspect, the application provides a compound of formula I

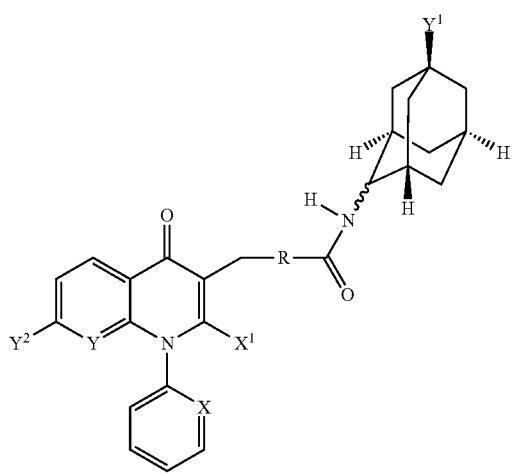

I wherein:
R is phenyl, or pyridonyl, optionally substituted with one or more R';
R' is halo or methoxy;

X is CH or N;
$X^1$ is H or C(=O)OCH$_3$ or 2-oxazole;
Y is CH or N;
$Y^1$ is OH, OC(=O)$Y^{1'}$, N($Y^{1'}$)$_2$, NHS(=O)$_2Y^{1'}$, NHC(=O)$Y^{1'}$, NHC(=O)C(CH$_3$)$_2$OH, NHCH$_2$C(CH$_3$)$_2$OH, or NHC(=O)C(CH$_3$)$_2$OC(=O)$Y^{1'}$;
each $Y^{1'}$ is independently H, lower alkyl, lower hydroxyalkyl, or cycloalkyl;
$Y^2$ is H, halo, or haloalkyl;
or a pharmaceutically acceptable salt thereof.

In one aspect, the application provides a method of treating a JNK-mediated disorder in a subject having a JNK-mediated disorder, said method comprising administering to a subject in need thereof a therapeutically effective amount of any of the above compounds.

In certain embodiments of the method of treating a JNK-mediated disorder, the JNK-mediated disorder is kidney disease.

In one aspect, the application provides a pharmaceutical composition comprising the compound of any one of the above embodiments, admixed with at least one pharmaceutically acceptable carrier, excipient or diluent.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise. Thus, the phrase "a" or "an" entity' as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R, X, $X^1$, $Y^1$, and $Y^2$) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

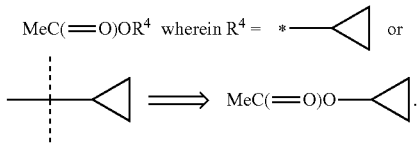

The symbol "⌇" as used herein refers to a bond that may be in either the cis or trans configuration.

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth.

Certain compounds of the invention may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)λCH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and diphenylmethyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "acyl" as used herein denotes a group of formula —C(=O)R wherein R is hydrogen or lower alkyl as defined herein. The term "alkylcarbonyl" as used herein denotes a group of formula C(=O)R wherein R is alkyl as defined herein. The term $C_{1-6}$ acyl refers to a group —C(=O)R wherein R contains 1-6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH₂CH(i-Pr)CH₂—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

"Aryl" means a monovalent cyclic aromatic hydrocarbon moiety consisting of a mono-, bi- or tricyclic aromatic ring.

The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

The term "base" includes, but is not limited to, NaOH, KOH, LiOH and alkali metal carbonates such as potassium carbonate, sodium carbonate, lithium carbonate, sodium bicarbonate, cesium carbonate and the like.

"Cycloalkyl" or "carbocyclic ring" means a monovalent saturated carbocyclic moiety consisting of monocyclic, bicyclic or tricyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Heterocycloalkyl lower alkyl" mean a moiety of the formula —$R^a$—$R^b$, where $R^a$ is lower alkylene and $R^b$ is heterocycloalkyl as defined herein.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocyclyl", "heterocycle", or "heterocycloalkyl" as used herein denotes a monovalent saturated cyclic radical, consisting of one or more rings, preferably one to two rings, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The term "hydroxyalkyl" as used herein denotes an alkyl radical as herein defined wherein one to three hydrogen atoms on different carbon atoms is/are replaced by hydroxyl groups.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDC), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-$BuMe_2Si$ (TBDMS), triethylamine (TEA or $Et_3$ N), 2,2,6,6-tetramethylpiperidine 1-oxyl (TEMPO), triflate or $CF_3SO_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

"Heteroalkyl" means an alkyl moiety as defined herein, including a branched $C_4$-$C_7$ alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is O, $R^d$ is hydrogen, alkyl, cycloalkyl, or cycloalkylalkyl; when n is 1, $R^d$ is alkyl, cycloalkyl, or cycloalkylalkyl; and when n is 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-amino-ethyl, 3-aminopropyl, 2-methylsulfonylethyl, aminosulfonylmethyl, aminosulfonylethyl, amino-sulfonylpropyl, methylaminosulfonylmethyl, methylaminosulfonylethyl, methylaminosulfonyl-propyl, and the like.

"Heteroaryl" means a monocyclic or bicyclic moiety of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, pyridazinyl, quinolinyl, isoquinolinyl, benzofuryl, benzofuranyl, benzothiophenyl, benzothiopyranyl, benz-imidazolyl, benzoxazolyl, benzooxadiazolyl, benzothiazolyl, benzothiadiazolyl, benzopyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo," "halogen," and "halide" are used interchangeably herein and refer to fluoro, chloro, bromo, and iodo.

"Haloalkyl" means alkyl as defined herein in which one or more hydrogen has been replaced with same or different halogen. The term "lower haloalkyl" denotes a straight or branched chain hydrocarbon residue containing 1 to 6 carbon atoms substituted with one or more halogen atom. Exemplary haloalkyls include —$CH_2Cl$, —$CH_2CF_3$, —$CH_2CCl_3$, —$CF_2CF_3$, —$CF_3$, and the like.

"Heterocyclyl" or "heterocycloalkyl" means a monovalent saturated moiety, consisting of one to two rings, incorporating one, two, or three or four heteroatoms (chosen from nitrogen, oxygen or sulfur). The heterocyclyl ring may be optionally fuse to a heteroaryl group as defined herein. The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydro-pyranyl, thiamorpholinyl, thiamorpholinylsulfoxide, thiamorpholinylsulfone, dihydroquinolinyl, dihydroisoquinolinyl, tetrahydroquinolinyl, tetrahydroisoquinolinyl, octahydro-pyrrolo[1,2-a]pyrazine, octahydro-pyrido[1,2-a]pyrazine, 5,6,7,8-tetrahydro-[1,2,4]triazolo[4,3-a]pyrazine, 5,6,7,8-tetrahydro-imidazo[1,2-a]pyrazine and the like.

"Optionally substituted" means a substituent which is substituted independently with zero to three substituents selected from lower alkyl, halo, OH, cyano, amino, nitro, lower alkoxy, or halo-lower alkyl.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzene-sulfonyloxy, tosyloxy, and thienyloxy, dihalophosphinoyloxy, optionally substituted benzyloxy, isopropyloxy, acyloxy, and the like.

"Optional" or "optionally" means that the subsequently described event or circumstance may but need not occur, and that the description includes instances where the event or circumstance occurs and instances in which it does not.

"Agonist" refers to a compound that enhances the activity of another compound or receptor site.

"Antagonist" refers to a compound that diminishes or prevents the action of another compound or receptor site.

The term "drug candidate" refers to a compound or preparation which is to be tested for possible effect in the treatment of a disease state in an animal, regardless of whether said drug candidate has any known biological activity.

The term "homologous" as used herein refers to a protein that performs substantially the same function in another subject species and shares substantial sequence identity, to the extent that they are recognized in the art as being different versions of the same protein, differing primarily in the species in which they are found. Thus, for example, human ERG, mouse ERG, and rat ERG are all considered homologous to each other.

"Modulator" means a molecule that interacts with a target. The interactions include, but are not limited to, agonist, antagonist, and the like, as defined herein.

"Disease" and "Disease state" means any disease, condition, symptom, disorder or indication.

The term "cell line" refers to a clone of immortalized mammalian cells. A "stable" cell line is a cell line that exhibits substantially consistent characteristics over time (e.g., with each doubling). A stable cell line within the scope of this invention provides a substantial proportion of cells that are capable of providing a seal resistance of greater than about 50 MOhm, a current amplitude of greater than about 200 pA, and provide a current amplitude that does not vary by more than approximately 20% over one hour under control conditions.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" includes mammals and birds. "Mammals" means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

"Pharmacological effect" as used herein encompasses effects produced in the subject that achieve the intended purpose of a therapy. For example, a pharmacological effect would be one that results in the prevention, alleviation or reduction of urinary incontinence in a treated subject.

"Treating" or "treatment" of a disease state includes (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms; or (iii) relieving the disease state, i.e., causing temporary or permanent regression of the disease state or its clinical symptoms.

All patents and publications identified herein are incorporated herein by reference in their entirety.

Inhibitors of JNK

In one aspect, the application provides a compound of formula I

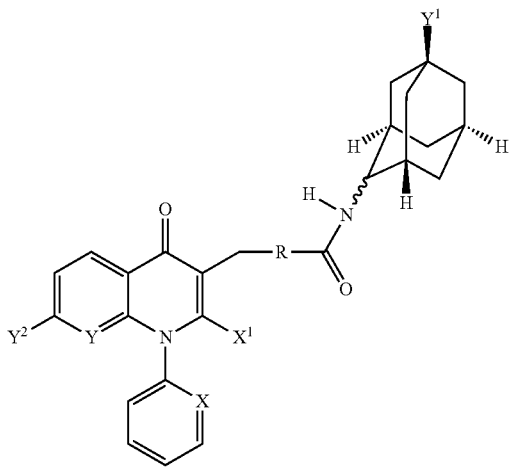

wherein:
wherein:
R is phenyl, or pyridonyl, optionally substituted with one or more R';
R' is halo or methoxy;
X is CH or N;
$X^1$ is H or C(=O)OCH$_3$ or 2-oxazole;
Y is CH or N;
$Y^1$ is OH, OC(=O)$Y^{1'}$, N($Y^{1'}$)$_2$, NHS(=O)$_2Y^{1'}$, NHC(=O)$Y^{1'}$, NHC(=O)C(CH$_3$)$_2$OH, NHCH$_2$C(CH$_3$)$_2$OH, or NHC(=O)C(CH$_3$)$_2$OC(=O)$Y^{1'}$;
each $Y^{1'}$ is independently H, lower alkyl, lower hydroxyalkyl, or cycloalkyl;
$Y^2$ is H, halo, or haloalkyl;
or a pharmaceutically acceptable salt thereof.

In one variation of formula I, X is CH, and $X^1$ is C(=O)OCH$_3$.

In one variation of formula I, R is phenyl.

In one variation of formula I, R is phenyl, X is CH, and $X^1$ is C(=O)OCH$_3$.

In one variation of formula I, Y is CH and $Y^2$ is Cl.

In one variation of formula I, Y is N and $Y^2$ is H.

In one variation of formula I, X is CH, $X^1$ is C(=O)OCH$_3$, R is phenyl, Y is CH and $Y^2$ is Cl.

In one variation of formula I, X is CH, $X^1$ is C(=O)OCH$_3$, R is phenyl, Y is N and $Y^2$ is H.

In one variation of formula I, $Y^1$ is OH or OC(=O)$Y^{1'}$.

In one variation of formula I, X is CH, $X^1$ is C(=O)OCH$_3$, R is phenyl, and $Y^1$ is OH.

In one variation of formula I, $Y^1$ is NH$_2$.

In one variation of formula I, X is CH, X is C(=O)OCH$_3$, R is phenyl, and $Y^1$ is NH$_2$.

In one variation of formula I, $Y^1$ is NHS(=O)$_2Y^{1'}$.

In one variation of formula I, X is CH, $X^1$ is C(=O)OCH$_3$, R is phenyl, and $Y^1$ is NHS(=O)$_2Y^{1'}$.

In one variation of formula I, $Y^1$ is NHC(=O)$Y^{1'}$.

In one variation of formula I, X is CH, $X^1$ is C(=O)OCH$_3$, R is phenyl, and $Y^1$ is NHC(=O)$Y^{1'}$.

In one variation of formula I, $Y^1$ is NHC(=O)C(CH$_3$)$_2$OC(=O)CH$_3$.

In one variation of formula I, X is CH, $X^1$ is C(=O)OCH$_3$, R is phenyl, and $Y^1$ is NHC(=O)C(CH$_3$)$_2$OC(=O)CH$_3$.

In one variation of formula I, $Y^1$ is NHC(=O)C(CH$_3$)$_2$OH.

In one variation of formula I, X is CH, $X^1$ is C(=O)OCH$_3$, R is phenyl, and $Y^1$ is NHC(=O)C(CH$_3$)$_2$OH.

In one variation of formula I, $Y^1$ is NHC(=O)CH$_3$.

In one variation of formula I, X is CH, X$^1$ is C(=O)OCH$_3$, R is phenyl, and Y is NHC(=O)CH$_3$.

In one variation of formula I, Y$^1$ is NHC(=O)C(CH$_3$)$_3$.

In one variation of formula I, X is CH, X$^1$ is C(=O)OCH$_3$, R is phenyl, and Y$^1$ is NHC(=O)C(CH$_3$)$_3$.

In one aspect, the application provides a compound selected from the group consisting of:

rel-3-[4-((1S,2S,3R,5S,7S)-5-Hydroxy-adamantan-2-ylcarbamoyl)-benzyl]-4-oxo-1-phenyl-1,4-dihydro-[1,8]naphthyridine-2-carboxylic acid methyl ester;

rel-3-[4-((1S,2R,3R,5S,7S)-5-Hydroxy-adamantan-2-ylcarbamoyl)-benzyl]-4-oxo-1-phenyl-1,4-dihydro-[1,8]naphthyridine-2-carboxylic acid methyl ester;

rel-7-Chloro-3-[4-((1S,2S,3R,5S,7S)-5-hydroxy-adamantan-2-ylcarbamoyl)-benzyl]-4-oxo-1-phenyl-1,4-dihydro-quinoline-2-carboxylic acid methyl ester;

rel-7-Chloro-3-[4-((1S,2R,3R,5S,7S)-5-hydroxy-adamantan-2-ylcarbamoyl)-benzyl]-4-oxo-1-phenyl-1,4-dihydro-quinoline-2-carboxylic acid methyl ester;

rel-4-(7-Chloro-4-oxo-1-pyridin-2-yl-1,4-dihydro-quinolin-3-ylmethyl)-N-((1S,2S,3R,5S,7S)-5-hydroxy-adamantan-2-yl)-benzamide;

rel-3-[4-((1S,2S,3R,5S,7S)-5-Acetoxy-adamantan-2-ylcarbamoyl)-benzyl]-7-chloro-4-oxo-1-phenyl-1,4-dihydro-quinoline-2-carboxylic acid methyl ester;

rel-3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester;

rel-3-[4-((1S,2R,3R,5S,7S)-5-amino-adamantan-2-ylcarbamoyl)-benzyl]-4-oxo-1-phenyl-1,4-dihydro-[1,8]naphthyridine-2-carboxylic acid methyl ester;

rel-3-[4-((1S,2S,3R,5S,7S)-5-Amino-adamantan-2-ylcarbamoyl)-benzyl]-7-chloro-4-oxo-1-phenyl-1,4-dihydro-quinoline-2-carboxylic acid methyl ester;

rel-3-[4-((1S,2S,3R,5S,7S)-5-Acetylamino-adamantan-2-ylcarbamoyl)-benzyl]-7-chloro-4-oxo-1-phenyl-1,4-dihydro-quinoline-2-carboxylic acid methyl ester;

rel-7-Chloro-3-{4-[(1S,2S,3R,5S,7S)-5-(2,2-dimethyl-propionylamino)-adamantan-2-ylcarbamoyl]-benzyl}-4-oxo-1-phenyl-1,4-dihydro-quinoline-2-carboxylic acid methyl ester;

rel-3-{4-[(1S,2S,3R,5S,7S)-5-(2-Acetoxy-2-methyl-propionylamino)-adamantan-2-ylcarbamoyl]-benzyl}-7-chloro-4-oxo-1-phenyl-1,4-dihydro-quinoline-2-carboxylic acid methyl ester;

rel-7-Chloro-3-{4-[(1S,2S,3R,5S,7S)-5-(2-hydroxy-2-methyl-propionylamino)-adamantan-2-ylcarbamoyl]-benzyl}-4-oxo-1-phenyl-1,4-dihydro-quinoline-2-carboxylic acid methyl ester;

rel-7-Chloro-3-[4-((1S,2S,3R,5S,7S)-5-cyclopropanesulfonylamino-adamantan-2-ylcarbamoyl)-benzyl]-4-oxo-1-phenyl-1,4-dihydro-quinoline-2-carboxylic acid methyl ester;

rel-7-Chloro-3-[4-((1S,2S,3R,5S,7S)-5-methanesulfonylamino-adamantan-2-ylcarbamoyl)-benzyl]-4-oxo-1-phenyl-1,4-dihydro-quinoline-2-carboxylic acid methyl ester;

rel-7-Chloro-3-{4-[(1S,2S,3R,5S,7S)-5-(2-hydroxy-2-methyl-propylamino)-adamantan-2-ylcarbamoyl]-benzyl}-4-oxo-1-phenyl-1,4-dihydro-quinoline-2-carboxylic acid methyl ester;

rel-3-[4-((1S,2S,3R,5S,7S)-5-Acetylamino-adamantan-2-ylcarbamoyl)-benzyl]-4-oxo-1-phenyl-1,4-dihydro-[1,8]naphthyridine-2-carboxylic acid methyl ester;

rel-3-[4-((1S,2S,3R,5S,7S)-5-Cyclopropanesulfonylamino-adamantan-2-ylcarbamoyl)-benzyl]-4-oxo-1-phenyl-1,4-dihydro-[1,8]naphthyridine-2-carboxylic acid methyl ester;

rel-3-[4-((1S,2S,3R,5S,7S)-5-Methanesulfonylamino-adamantan-2-ylcarbamoyl)-benzyl]-4-oxo-1-phenyl-1,4-dihydro-[1,8]naphthyridine-2-carboxylic acid methyl ester;

rel-3-{4-[(1S,2S,3R,5S,7S)-5-(2,2-Dimethyl-propionylamino)-adamantan-2-ylcarbamoyl]-benzyl}-4-oxo-1-phenyl-1,4-dihydro-[1,8]naphthyridine-2-carboxylic acid methyl ester;

rel-3-{4-[(1S,2S,3R,5S,7S)-5-(2-Acetoxy-2-methyl-propionylamino)-adamantan-2-ylcarbamoyl]-benzyl}-4-oxo-1-phenyl-1,4-dihydro-[1,8]naphthyridine-2-carboxylic acid methyl ester;

rel-3-{4-[(1S,2S,3R,5S,7S)-5-(2-Hydroxy-2-methyl-propionylamino)-adamantan-2-ylcarbamoyl]-benzyl}-4-oxo-1-phenyl-1,4-dihydro-[1,8]naphthyridine-2-carboxylic acid methyl;

rel-3-[4-((1S,2S,3R,5S,7S)-5-Hydroxy-adamantan-2-ylcarbamoyl)-2-methoxy-benzyl]-4-oxo-1-phenyl-1,4-dihydro-[1,8]naphthyridine-2-carboxylic acid methyl ester;

rel-3-[2-Fluoro-4-((1S,2S,3R,5S,7S)-5-hydroxy-adamantan-2-ylcarbamoyl)-benzyl]-4-oxo-1-phenyl-1,4-dihydro-[1,8]naphthyridine-2-carboxylic acid methyl ester;

rel-3-[4-((1S,2S,3R,5S,7S)-5-Hydroxy-adamantan-2-ylcarbamoyl)-benzyl]-4-oxo-1-phenyl-7-trifluoromethyl-1,4-dihydro-[1,8]naphthyridine-2-carboxylic acid methyl ester;

rel-7-Chloro-3-[4-((1S,2S,3R,5S,7S)-5-hydroxy-adamantan-2-ylcarbamoyl)-2-oxo-2H-pyridin-1-ylmethyl]-4-oxo-1-phenyl-1,4-dihydro-quinoline-2-carboxylic acid methyl ester; and Rel-4-(7-Chloro-2-oxazol-2-yl-4-oxo-1-phenyl-1,4-dihydro-quinolin-3-ylmethyl)-N-((1S,2S,3R,5S,7S)-5-hydroxy-adamantan-2-yl)-benzamide.

In one aspect, the application provides a method of treating a JNK-mediated disorder in a subject having a JNK-mediated disorder, said method comprising administering to a subject in need thereof a therapeutically effective amount of any of the above compounds.

In certain embodiments of the method of treating a JNK-mediated disorder, the JNK-mediated disorder is characterized by cellular proliferation.

In certain embodiments of the method of treating a JNK-mediated disorder, the JNK-mediated disorder is arthritis.

In certain embodiments of the method of treating a JNK-mediated disorder, the JNK-mediated disorder is rheumatoid arthritis.

In certain embodiments of the method of treating a JNK-mediated disorder, the JNK-mediated disorder is asthma.

In certain embodiments of the method of treating a JNK-mediated disorder, the JNK-mediated disorder is diabetes.

In certain embodiments of the method of treating a JNK-mediated disorder, the JNK-mediated disorder is Alzheimer's disease.

In certain embodiments of the method of treating a JNK-mediated disorder, the JNK-mediated disorder is Parkinson's disease.

In certain embodiments of the method of treating a JNK-mediated disorder, the JNK-mediated disorder is ischemic stroke.

In certain embodiments of the method of treating a JNK-mediated disorder, the JNK-mediated disorder is cancer.

In certain embodiments of the method for treating a JNK-mediated disorder, wherein the JNK-mediated disorder is cancer, the cancer is brain cancer.

In certain embodiments of the method for treating a JNK-mediated disorder, wherein the JNK-mediated disorder is cancer, the cancer is leukemia.

In certain embodiments of the method of treating a JNK-mediated disorder, the JNK-mediated disorder is kidney disease.

In one aspect, the application provides a pharmaceutical composition comprising the compound of any one of the above embodiments, admixed with at least one pharmaceutically acceptable carrier, excipient or diluent.

In one aspect, the application provides a method for treating a JNK-mediated disorder comprising co-administering to a patient in need thereof a therapeutically effective amount of an anti-inflammatory compound in combination with the compound of any of the above embodiments, variations, or aspects (not just for inflammation).

The application provides a use of a compound of Formula I or Formula II in the preparation of a medicament for the treatment of autoimmune and inflammatory diseases associated with JNK modulation.

A compound, method, or use as described herein.

All publications cited in this disclosure are incorporated herein by reference in their entirety.

Compounds

The compounds described below are JNK inhibitors useful for inhibiting JNK and treating JNK-mediated disorders, and the like. Examples of representative compounds encompassed by the present invention and within the scope of the invention are provided in Table I as compounds.

In general, the nomenclature used in this application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE 1

| Compound | Structure | Nomenclature |
|---|---|---|
| I-1 | 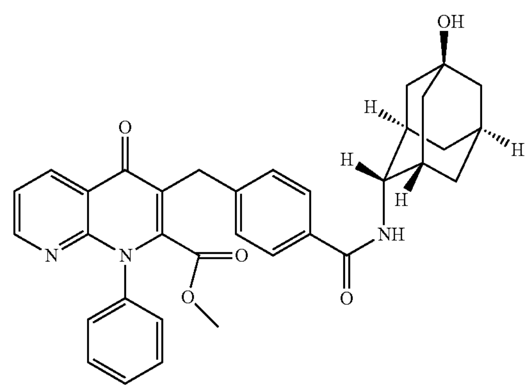 [SMILES: COC(=O)c1c(Cc2ccc(C(=O)N[C@@H]3[C@@H]4C[C@@H]5C[C@H]3C[C@@](O)(C5)C4)cc2)c(=O)c2cccnc2n1-c1ccccc1] | rel-3-[4-((1S,2S,3R,5S,7S)-5-Hydroxy-adamantan-2-ylcarbamoyl)-benzyl]-4-oxo-1-phenyl-1,4-dihydro-[1,8]naphthyridine-2-carboxylic acid methyl ester |
| I-2 | 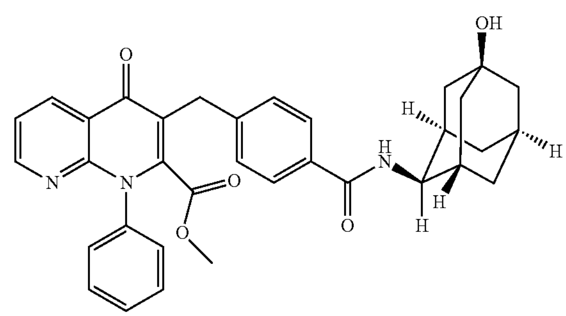 [SMILES: COC(=O)c1c(Cc2ccc(C(=O)N[C@H]3[C@@H]4C[C@@H]5C[C@H]3C[C@@](O)(C5)C4)cc2)c(=O)c2cccnc2n1-c1ccccc1] | rel-3-[4-((1S,2R,3R,5S,7S)-5-Hydroxy-adamantan-2-ylcarbamoyl)-benzyl]-4-oxo-1-phenyl-1,4-dihydro-[1,8]naphthyridine-2-carboxylic acid methyl ester |
| I-3 | 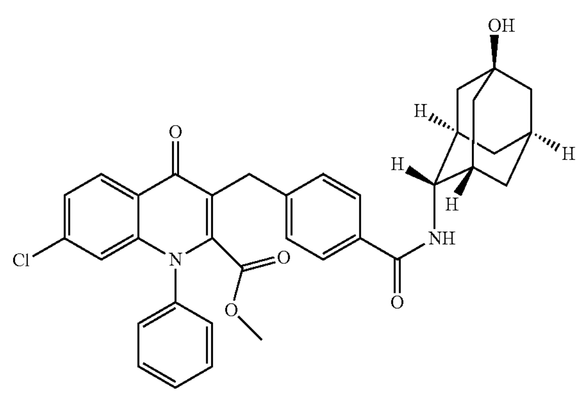 [SMILES: COC(=O)c1c(Cc2ccc(C(=O)N[C@@H]3[C@@H]4C[C@@H]5C[C@H]3C[C@@](O)(C5)C4)cc2)c(=O)c2ccc(Cl)cc2n1-c1ccccc1] | rel-7-Chloro-3-[4-((1S,2S,3R,5S,7S)-5-hydroxy-adamantan-2-ylcarbamoyl)-benzyl]-4-oxo-1-phenyl-1,4-dihydro-quinoline-2-carboxylic acid methyl ester |

TABLE 1-continued

| Compound | Structure | Nomenclature |
|---|---|---|
| I-4 | 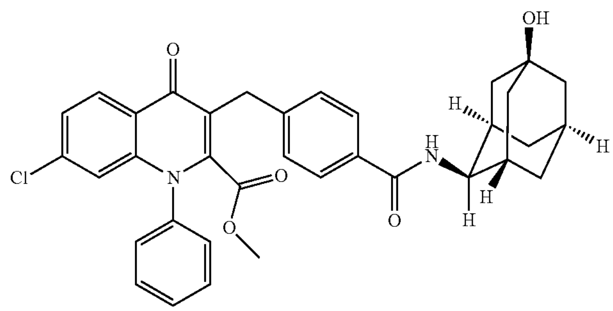 [SMILES: COC(=O)c1c(Cc2ccc(C(=O)N[C@H]3[C@@H]4C[C@@H]5C[C@H]3C[C@@](O)(C5)C4)cc2)c(=O)c2ccc(Cl)cc2n1-c1ccccc1] | rel-7-Chloro-3-[4-((1S,2R,3R,5S,7S)-5-hydroxy-adamantan-2-ylcarbamoyl)-benzyl]-4-oxo-1-phenyl-1,4-dihydro-quinoline-2-carboxylic acid methyl ester |
| I-5 | 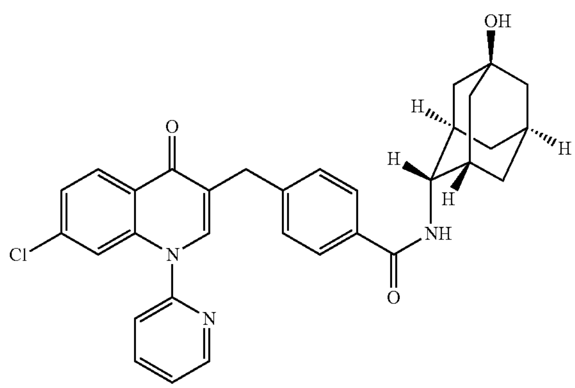 [SMILES: O=C(N[C@@H]1[C@@H]2C[C@@H]3C[C@H]1C[C@@](O)(C3)C2)c1ccc(Cc2cn(-c3ccccn3)c3cc(Cl)ccc3c2=O)cc1] | rel-4-(7-Chloro-4-oxo-1-pyridin-2-yl-1,4-dihydro-quinolin-3-ylmethyl)-N-((1S,2S,3R,5S,7S)-5-hydroxy-adamantan-2-yl)-benzamide |
| I-6 | 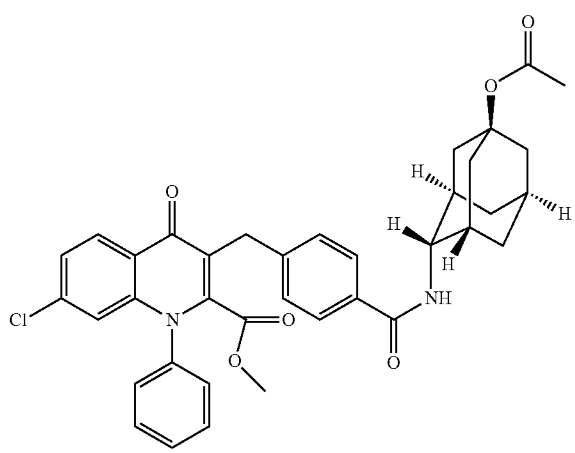 [SMILES: COC(=O)c1c(Cc2ccc(C(=O)N[C@@H]3[C@@H]4C[C@@H]5C[C@H]3C[C@@](OC(C)=O)(C5)C4)cc2)c(=O)c2ccc(Cl)cc2n1-c1ccccc1] | rel-3-[4-((1S,2S,3R,5S,7S)-5-Acetoxy-adamantan-2-ylcarbamoyl)-benzyl]-7-chloro-4-oxo-1-phenyl-1,4-dihydro-quinoline-2-carboxylic acid methyl ester |
| I-7 | 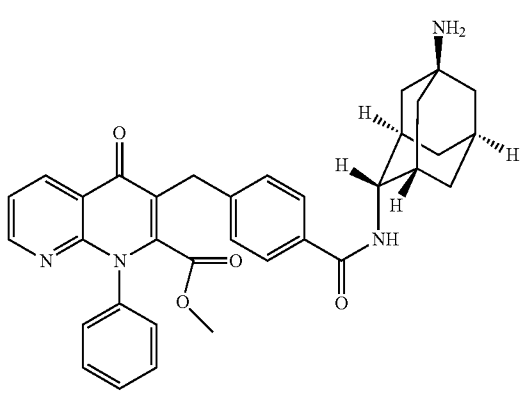 [SMILES: COC(=O)c1c(Cc2ccc(C(=O)N[C@@H]3[C@@H]4C[C@@H]5C[C@H]3C[C@@](N)(C5)C4)cc2)c(=O)c2cccnc2n1-c1ccccc1] | rel-3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester |

TABLE 1-continued

| Compound | Structure | Nomenclature |
|---|---|---|
| I-8 | 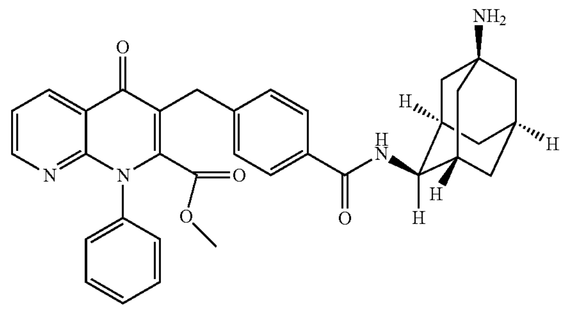 | rel-3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester |
| I-9 | 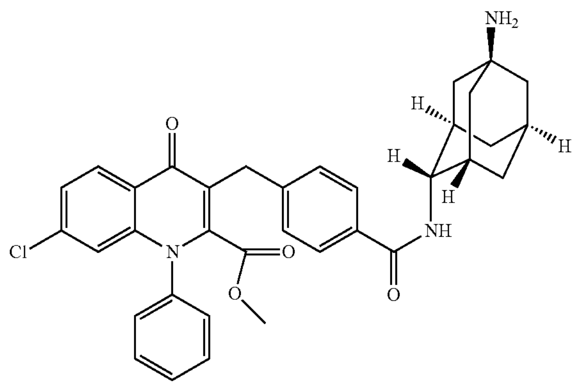 [SMILES: COC(=O)c1c(Cc2ccc(C(=O)N[C@@H]3[C@@H]4C[C@@H]5C[C@H]3C[C@@](N)(C5)C4)cc2)c(=O)c2ccc(Cl)cc2n1-c1ccccc1] | rel-3-[4-((1S,2S,3R,5S,7S)-5-Amino-adamantan-2-ylcarbamoyl)-benzyl]-7-chloro-4-oxo-1-phenyl-1,4-dihydro-quinoline-2-carboxylic acid methyl ester |
| I-10 | 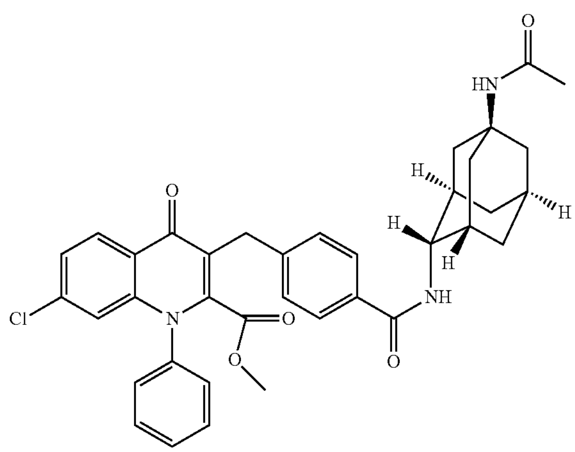 | rel-3-[4-((1S,2S,3R,5S,7S)-5-Acetylamino-adamantan-2-ylcarbamoyl)-benzyl]-7-chloro-4-oxo-1-phenyl-1,4-dihydro-quinoline-2-carboxylic acid methyl ester |
| I-11 | 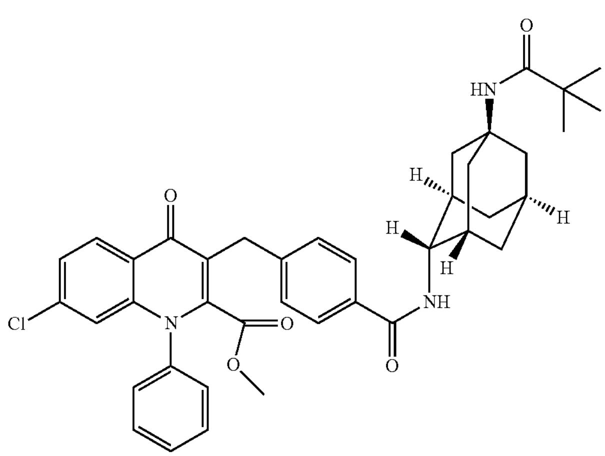 [SMILES: COC(=O)c1c(Cc2ccc(C(=O)N[C@@H]3[C@@H]4C[C@@H]5C[C@H]3C[C@@](NC(=O)C(C)(C)C)(C5)C4)cc2)c(=O)c2ccc(Cl)cc2n1-c1ccccc1] | rel-7-Chloro-3-{4-[(1S,2S,3R,5S,7S)-5-(2,2-dimethyl-propionylamino)-adamantan-2-ylcarbamoyl]-benzyl}-4-oxo-1-phenyl-1,4-dihydro-quinoline-2-carboxylic acid methyl ester |

| Compound | Structure | Nomenclature |
|---|---|---|
| I-12 | 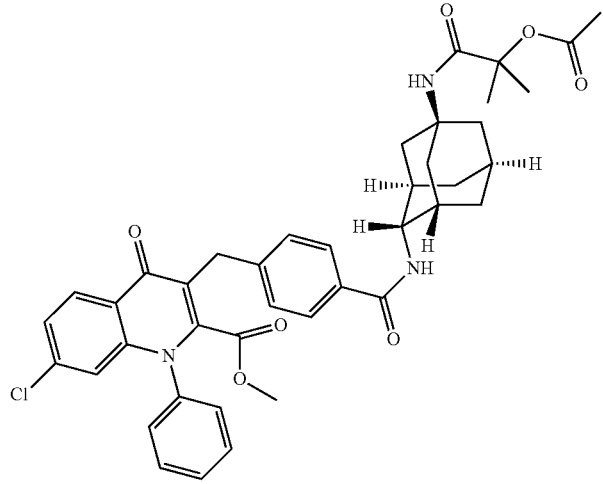 [SMILES: COC(=O)c1c(Cc2ccc(C(=O)N[C@@H]3[C@@H]4C[C@@H]5C[C@H]3C[C@@](NC(=O)C(C)(C)OC(C)=O)(C5)C4)cc2)c(=O)c2ccc(Cl)cc2n1-c1ccccc1] | rel-3-{4-[(1S,2S,3R,5S,7S)-5-(2-Acetoxy-2-methyl-propionylamino)-adamantan-2-ylcarbamoyl]-benzyl}-7-chloro-4-oxo-1-phenyl-1,4-dihydro-quinoline-2-carboxylic acid methyl ester |
| I-13 | 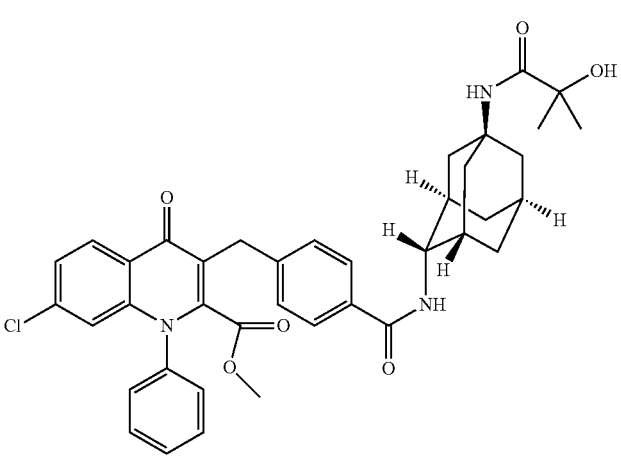 [SMILES: COC(=O)c1c(Cc2ccc(C(=O)N[C@@H]3[C@@H]4C[C@@H]5C[C@H]3C[C@@](NC(=O)C(C)(C)O)(C5)C4)cc2)c(=O)c2ccc(Cl)cc2n1-c1ccccc1] | rel-7-Chloro-3-{4-[(1S,2S,3R,5S,7S)-5-(2-hydroxy-2-methyl-propionylamino)-adamantan-2-ylcarbamoyl]-benzyl}-4-oxo-1-phenyl-1,4-dihydro-quinoline-2-carboxylic acid methyl ester |
| I-14 | 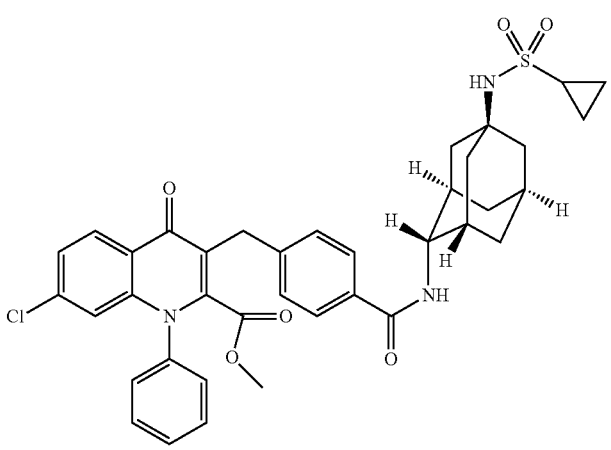 [SMILES: COC(=O)c1c(Cc2ccc(C(=O)N[C@@H]3[C@@H]4C[C@@H]5C[C@H]3C[C@@](NS(=O)(=O)C3CC3)(C5)C4)cc2)c(=O)c2ccc(Cl)cc2n1-c1ccccc1] | rel-7-Chloro-3-[4-((1S,2S,3R,5S,7S)-5-cyclopropanesulfonylamino-adamantan-2-ylcarbamoyl)-benzyl]-4-oxo-1-phenyl-1,4-dihydro-quinoline-2-carboxylic acid methyl ester |

TABLE 1-continued

| Compound | Structure | Nomenclature |
|---|---|---|
| I-15 | 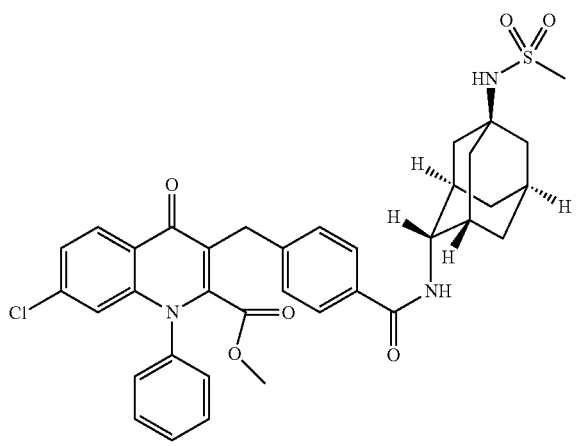 [SMILES: COC(=O)c1c(Cc2ccc(C(=O)N[C@@H]3[C@@H]4C[C@@H]5C[C@H]3C[C@@](NS(C)(=O)=O)(C5)C4)cc2)c(=O)c2ccc(Cl)cc2n1-c1ccccc1] | rel-7-Chloro-3-[4-((1S,2S,3R,5S,7S)-5-methanesulfonylamino-adamantan-2-ylcarbamoyl)-benzyl]-4-oxo-1-phenyl-1,4-dihydro-quinoline-2-carboxylic acid methyl ester |
| I-16 | 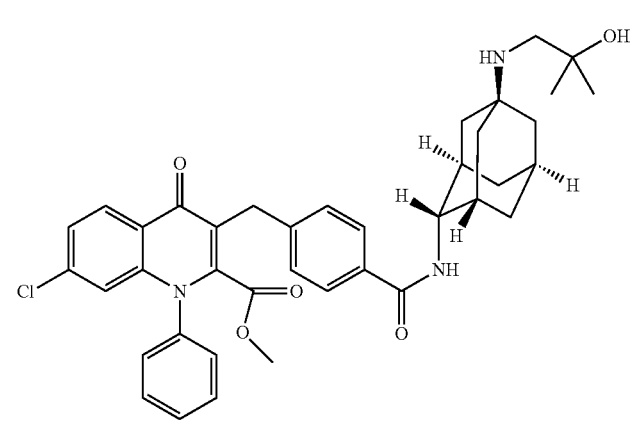 [SMILES: COC(=O)c1c(Cc2ccc(C(=O)N[C@@H]3[C@@H]4C[C@@H]5C[C@H]3C[C@@](NCC(C)(C)O)(C5)C4)cc2)c(=O)c2ccc(Cl)cc2n1-c1ccccc1] | rel-7-Chloro-3-{4-[(1S,2S,3R,5S,7S)-5-(2-hydroxy-2-methyl-propylamino)-adamantan-2-ylcarbamoyl]-benzyl}-4-oxo-1-phenyl-1,4-dihydro-quinoline-2-carboxylic acid methyl ester |
| I-17 | 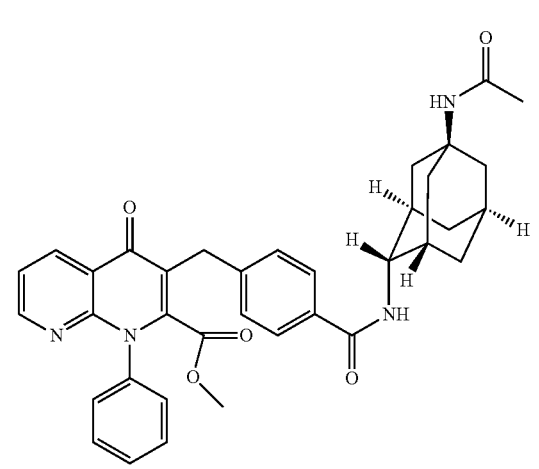 [SMILES: COC(=O)c1c(Cc2ccc(C(=O)N[C@@H]3[C@@H]4C[C@@H]5C[C@H]3C[C@@](NC(C)=O)(C5)C4)cc2)c(=O)c2cccnc2n1-c1ccccc1] | rel-3-[4-((1S,2S,3R,5S,7S)-5-Acetylamino-adamantan-2-ylcarbamoyl)-benzyl]-4-oxo-1-phenyl-1,4-dihydro-[1,8]naphthyridine-2-carboxylic acid methyl ester |

TABLE 1-continued

| Compound | Structure | Nomenclature |
|---|---|---|
| I-18 | 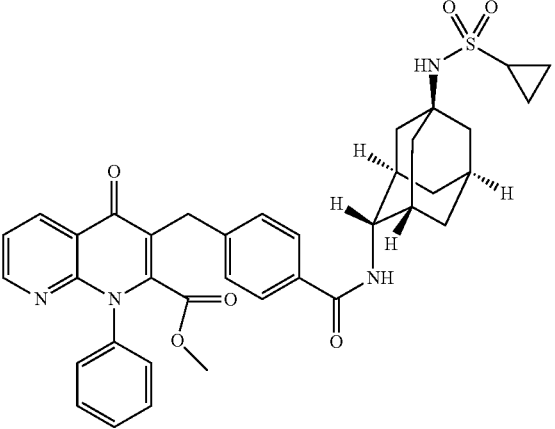 [SMILES: COC(=O)c1c(Cc2ccc(C(=O)N[C@@H]3[C@@H]4C[C@@H]5C[C@H]3C[C@@](NS(=O)(=O)C3CC3)(C5)C4)cc2)c(=O)c2cccnc2n1-c1ccccc1] | rel-3-[4-((1S,2S,3R,5S,7S)-5-Cyclopropanesulfonylamino-adamantan-2-ylcarbamoyl)-benzyl]-4-oxo-1-phenyl-1,4-dihydro-[1,8]naphthyridine-2-carboxylic acid methyl ester |
| I-19 | 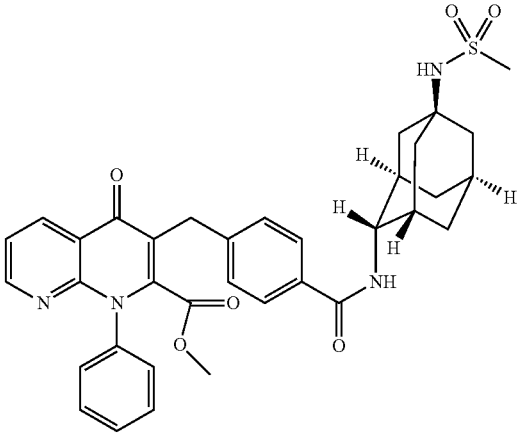 [SMILES: COC(=O)c1c(Cc2ccc(C(=O)N[C@@H]3[C@@H]4C[C@@H]5C[C@H]3C[C@@](NS(C)(=O)=O)(C5)C4)cc2)c(=O)c2cccnc2n1-c1ccccc1] | rel-3-[4-((1S,2S,3R,5S,7S)-5-Methanesulfonylamino-adamantan-2-ylcarbamoyl)-benzyl]-4-oxo-1-phenyl-1,4-dihydro-[1,8]naphthyridine-2-carboxylic acid methyl ester |
| I-20 | 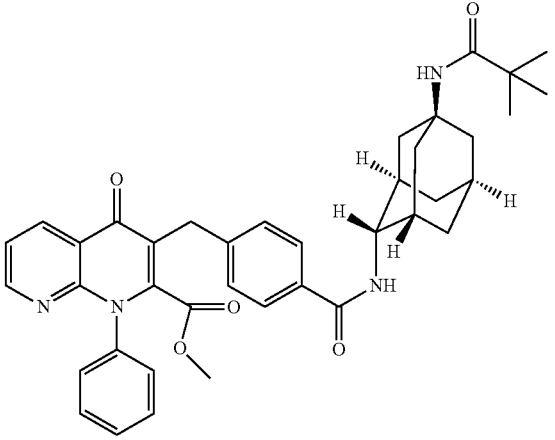 [SMILES: COC(=O)c1c(Cc2ccc(C(=O)N[C@@H]3[C@@H]4C[C@@H]5C[C@H]3C[C@@](NC(=O)C(C)(C)C)(C5)C4)cc2)c(=O)c2cccnc2n1-c1ccccc1] | rel-3-{4-[(1S,2S,3R,5S,7S)-5-(2,2-Dimethyl-propionylamino)-adamantan-2-ylcarbamoyl]-benzyl}-4-oxo-1-phenyl-1,4-dihydro-[1,8]naphthyridine-2-carboxylic acid methyl ester |

TABLE 1-continued

| Compound | Structure | Nomenclature |
| --- | --- | --- |
| I-21 | 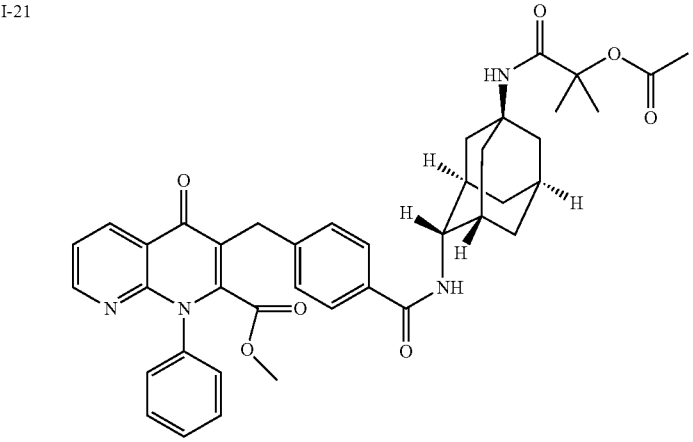 | rel-3-{4-[(1S,2S,3R,5S,7S)-5-(2-Acetoxy-2-methyl-propionylamino)-adamantan-2-ylcarbamoyl]-benzyl}-4-oxo-1-phenyl-1,4-dihydro-[1,8]naphthyridine-2-carboxylic acid methyl ester |
| I-22 | 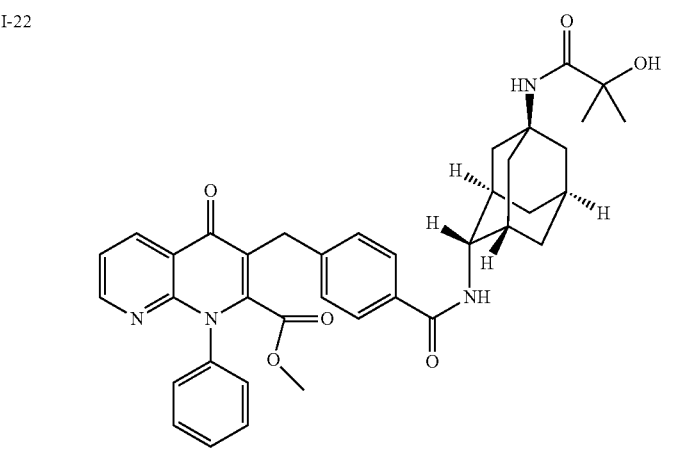 | rel-3-{4-[(1S,2S,3R,5S,7S)-5-(2-Hydroxy-2-methyl-propionylamino)-adamantan-2-ylcarbamoyl]-benzyl}-4-oxo-1-phenyl-1,4-dihydro-[1,8]naphthyridine-2-carboxylic acid methyl |
| I-23 | 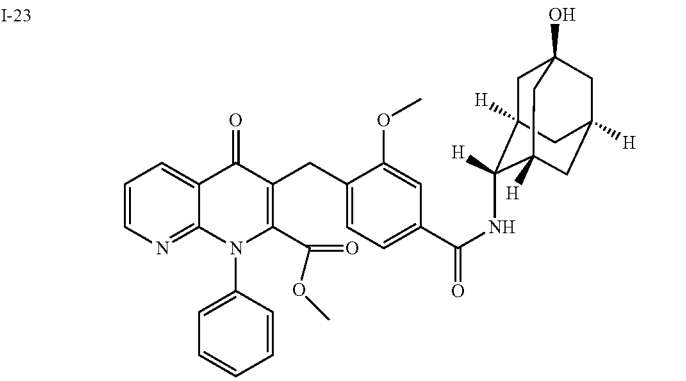 | rel-3-[4-((1S,2S,3R,5S,7S)-5-Hydroxy-adamantan-2-ylcarbamoyl)-2-methoxy-benzyl]-4-oxo-1-phenyl-1,4-dihydro-[1,8]naphthyridine-2-carboxylic acid methyl ester |

TABLE 1-continued

| Compound | Structure | Nomenclature |
|---|---|---|
| I-24 | 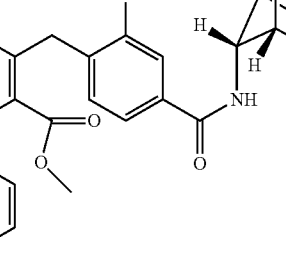 | rel-3-[2-Fluoro-4-((1S,2S,3R,5S,7S)-5-hydroxy-adamantan-2-ylcarbamoyl)-benzyl]-4-oxo-1-phenyl-1,4-dihydro-[1,8]naphthyridine-2-carboxylic acid methyl ester |
| I-25 | 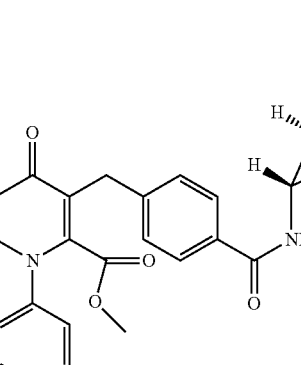 | rel-3-[4-((1S,2S,3R,5S,7S)-5-Hydroxy-adamantan-2-ylcarbamoyl)-benzyl]-4-oxo-1-phenyl-7-trifluoromethyl-1,4-dihydro-[1,8]naphthyridine-2-carboxylic acid methyl ester |
| I-26 | 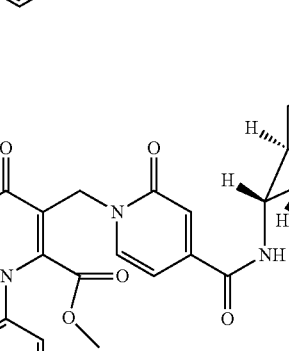 | rel-7-Chloro-3-[4-((1S,2S,3R,5S,7S)-5-hydroxy-adamantan-2-ylcarbamoyl)-2-oxo-2H-pyridin-1-ylmethyl]-4-oxo-1-phenyl-1,4-dihydro-quinoline-2-carboxylic acid methyl ester |
| I-27 | 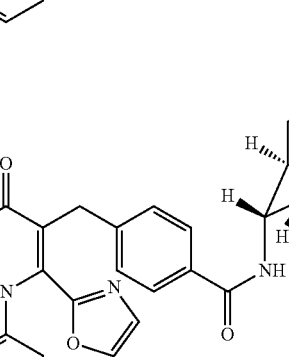 | Rel-4-(7-Chloro-2-oxazol-2-yl-4-oxo-1-phenyl-1,4-dihydro-quinolin-3-ylmethyl)-N-((1S,2S,3R,5S,7S)-5-hydroxy-adamantan-2-yl)-benzamide |

Synthesis—General Reaction Schemes

Scheme 1
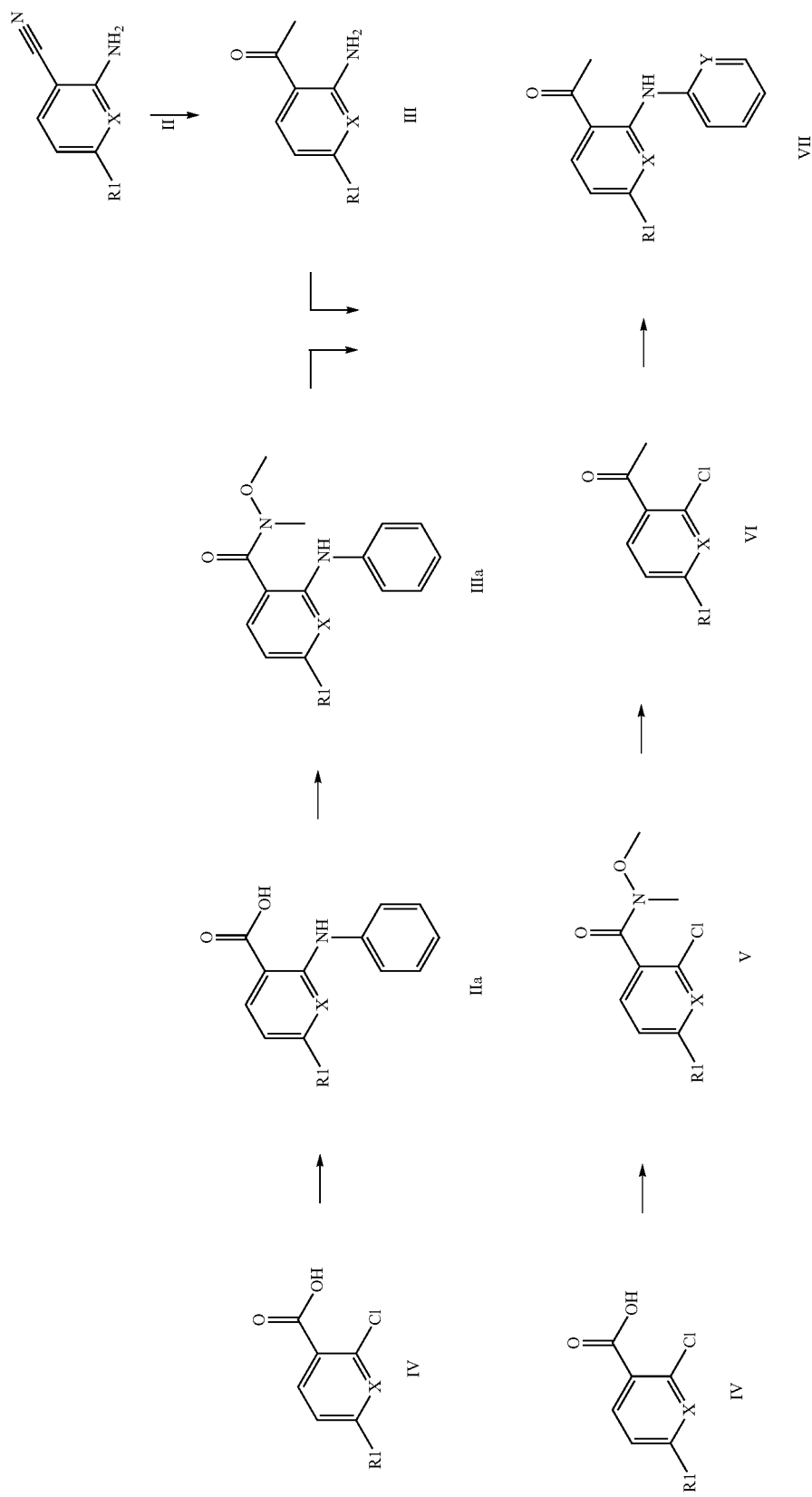

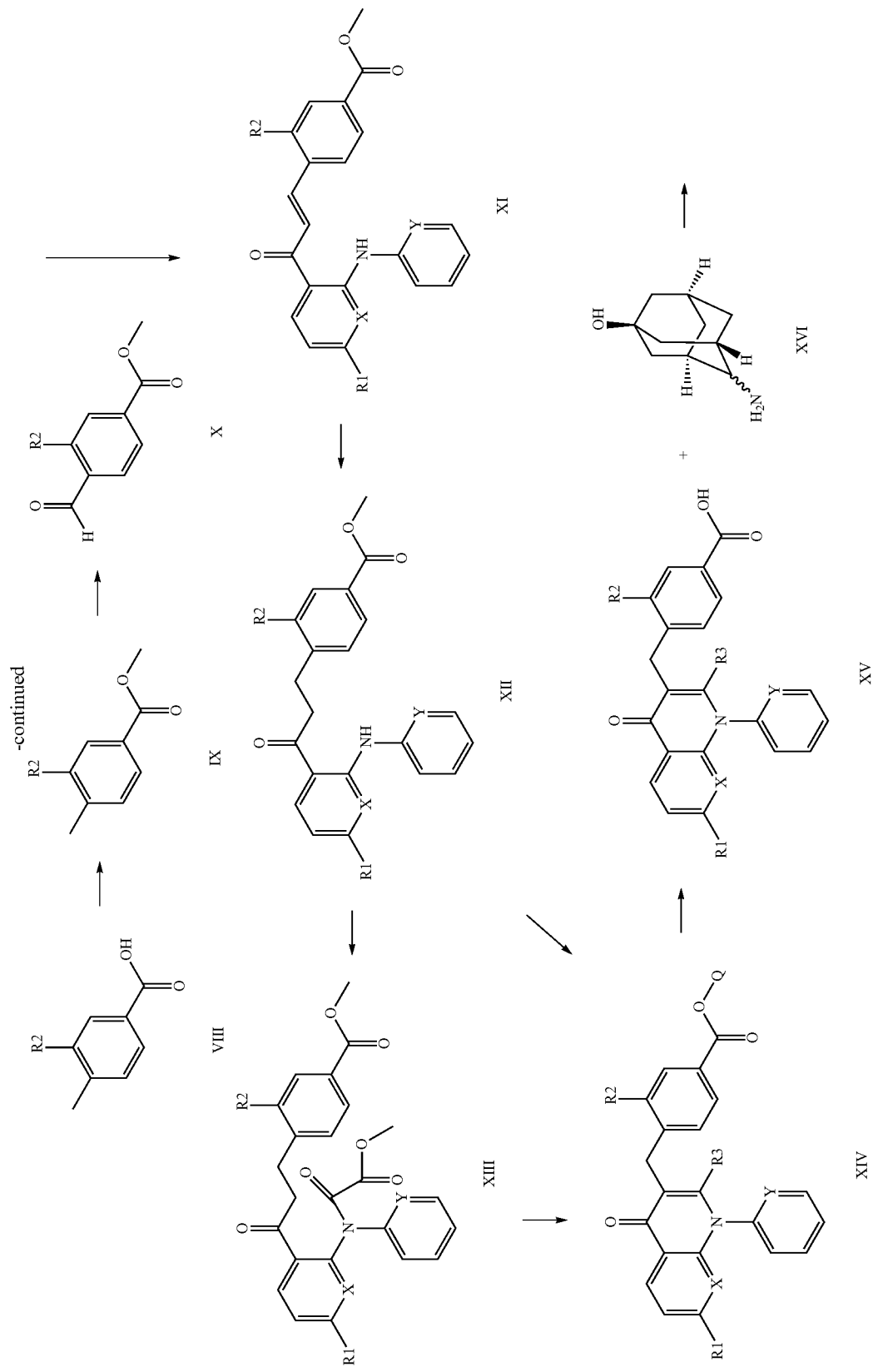

-continued
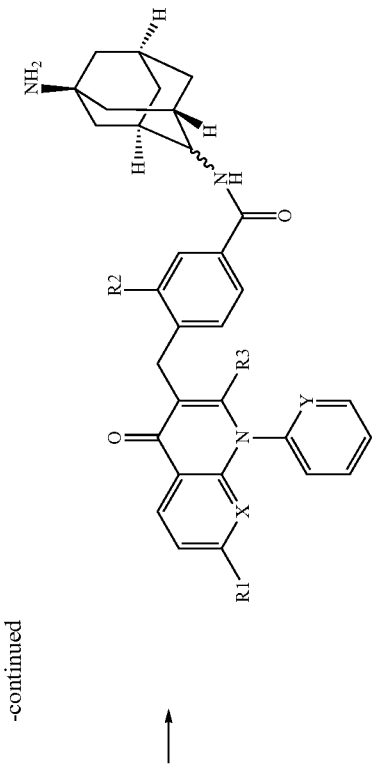
XVII
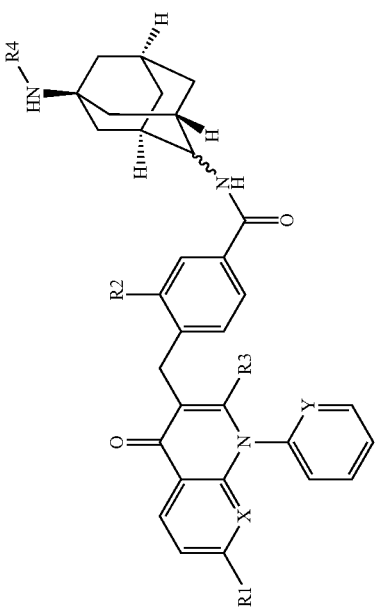
XVIII
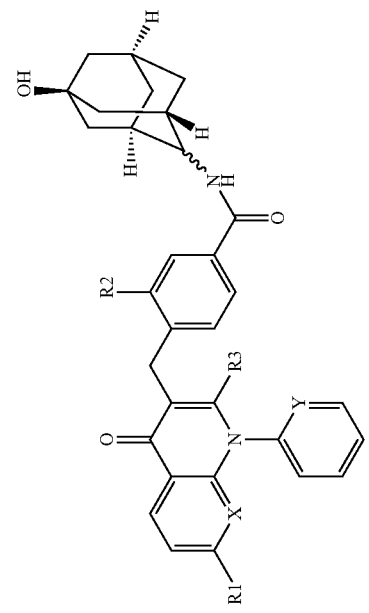
I
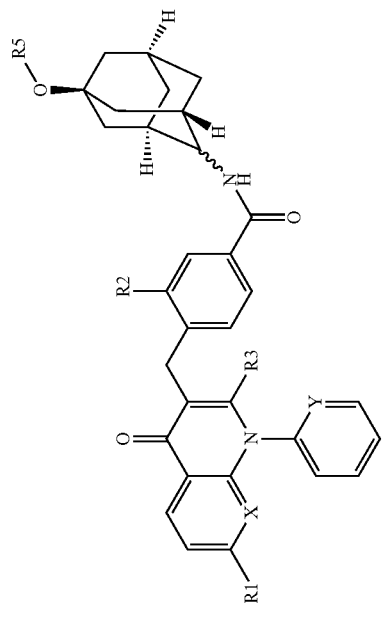
XIX

Scheme 2
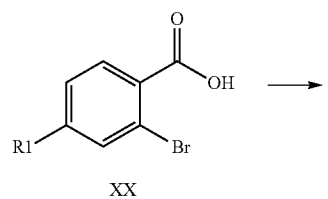
XX
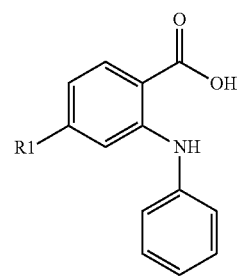
XXI
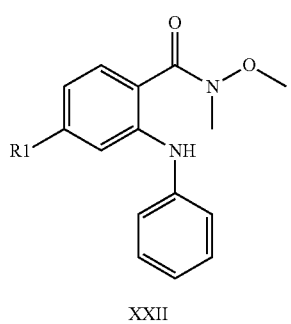
XXII
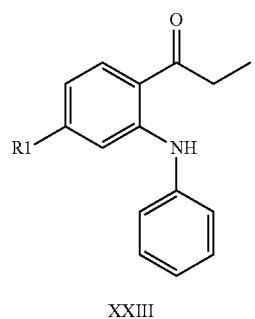
XXIII
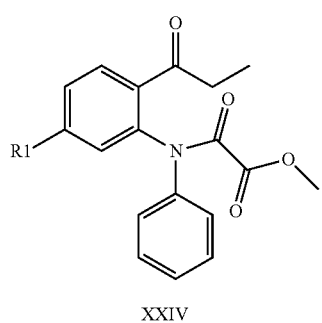
XXIV
-continued
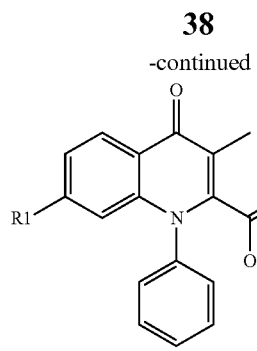
XXV
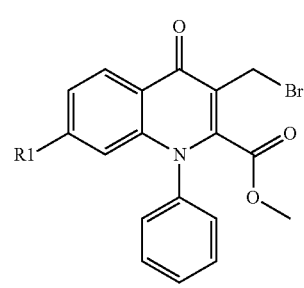
XXVI
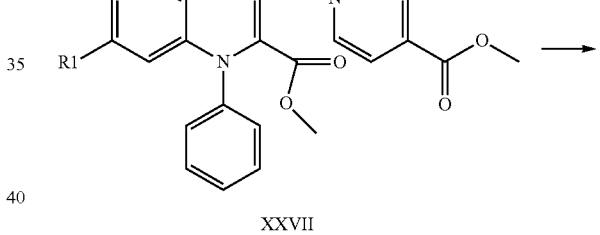
XXVII
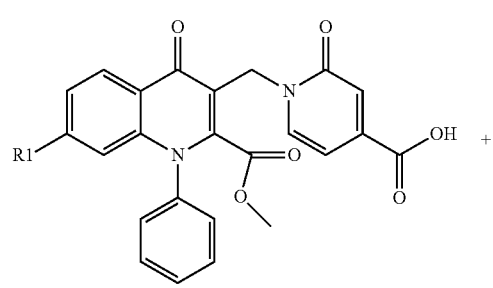
XXVIII
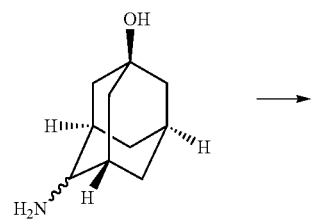
XVI

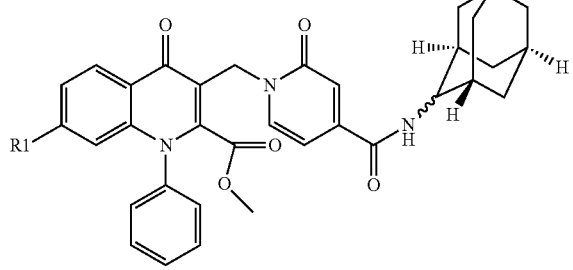

XXIX

The compounds of formula IV where X can be nitrogen and R₁ can be hydrogen or trifluoromethyl and the compound of formula II where X can be carbon and R₁ can be chloro are readily available from commercial sources.

The compound of formula III where X can be carbon and R₁ can be chloro can be prepared from the compound of formula II by treating with an appropriate Grignard reagent (see for example, PCT WO2008/138920 A1).

The compound of formula IIa where X can be nitrogen and R₁ can be trifluoromethyl can be prepared from the compound of formula IV where X can be nitrogen and R₁ can be trifluoromethyl by treatment under basic conditions with aniline (see for example, PCT WO2008/138920 A1).

The compound of formula IIIa where X can be nitrogen and R₁ can be trifluoromethyl can be prepared from the compound of formula IIa where X can be nitrogen and R₁ can be trifluoromethyl by treatment with N,O-dimethyl hydroxylamine hydrochloride under appropriate coupling conditions (see for example, PCT WO2008/138920 A1).

The compound of formula V where X can be nitrogen and R₁ can be hydrogen can be prepared from the compound of formula IV by treating the compound with N,O-dimethyl hydroxylamine hydrochloride under appropriate coupling conditions (see for example, PCT WO2008/138920 A1).

The compound of formula VI where X can be nitrogen and R₁ can be hydrogen can be prepared from the compound of formula V where X can be nitrogen and R₁ can be hydrogen by treating the compound with an appropriate Grignard reagent (see for example, PCT WO2008/138920 A1).

The compound of formula VII where X can be carbon, R₁ can be chloro and Y can be carbon or nitrogen can be prepared from the compound of formula III where X can be carbon, R₁ can be chloro and Y can be carbon or nitrogen by treatment with the appropriate aryl halide under metal coupling conditions (see for example, PCT WO2008/138920 A1).

The compound of formula VII where X can be nitrogen, R₁ can be hydrogen and Y can be carbon can be prepared from the compound of formula VI where X can be nitrogen, R₁ can be hydrogen and Y can be carbon by treatment with an aromatic amine (see for example, PCT WO2008/138920 A1).

The compound of formula VII where X can be nitrogen, R₁ can be trifluoromethyl and Y can be carbon can be prepared from the compound of formula IIIa where X can be nitrogen, R₁ can be trifluoromethyl and Y can be carbon and can be prepared by treatment with an appropriate Grignard reagent (see for example, PCT WO2008/138920 A1).

The compound of formula VIII where R₂ can be fluoro can be readily available from commercial sources.

The compound of formula IX where R₂ can be fluoro can be prepared from the compound of formula VIII where R₂ can be fluoro using standard methods to convert an aryl acid to an aryl methyl ester (see for example, Gauuan, P. J. F, Trova, M. P., Gregor-Boros, L., Bocckino, S. B., Crapo, J. D., and Day, B. J., *Bioorg. Med. Chem.*, 2002, 10, 3013-3021).

The compound of formula X where R₂ can be fluoro can be prepared from the compound of formula IX where R₂ can be fluoro under standard radical bromination condition (see for example, Gauuan, P. J. F, Trova, M. P., Gregor-Boros, L., Bocckino, S. B., Crapo, J. D., and Day, B. J., *Bioorg. Med. Chem.*, 2002, 10, 3013-3021). The resulting bromide may then be directly converted to the corresponding aldehyde using such conditions as silver nitrate (see for example, Gauuan, P. J. F, Trova, M. P., Gregor-Boros, L., Bocckino, S. B., Crapo, J. D., and Day, B. J., *Bioorg. Med. Chem.,* 2002, 10, 3013-3021).

The compound of formula X where R₂ can be hydroxy can be prepared from the corresponding benzoic acid. 4-Formyl-3-hydroxybenzoic acid can be commercially available. The hydroxy acid can be treated under standard methylation condition to provide the compound of formula X where R₂ can be methoxy (see for example, Adediran, S. A., Cabaret, D., Drouillat, B., Pratt, R. F., Wakselman, M., *Bioorg. Med. Chem.*, 2001, 9, 1175-1183).

The compound of formula XI where X can be nitrogen, R₁ can be hydrogen or trifluoromethyl, Y can be carbon and R₂ can be hydrogen, fluoro or methoxy can be prepared by treatment of the compound of formula VII where X can be nitrogen, R₁ can be hydrogen or trifluoromethyl and Y can be carbon with the compound of formula X where R₂ can be hydrogen, fluoro or methoxy under standard aldol condensation conditions (see for example, PCT WO2008/138920 A1).

The compound of formula XI where X can be carbon, R₁ can be chloro, R₂ can be hydrogen and Y can be carbon or nitrogen can be prepared by treatment of the compound of formula VII where X can be carbon, R₁ can be chloro and Y can be carbon or nitrogen with the compound of formula X where R₂ can be hydrogen under standard aldol condensation conditions (see for example, PCT WO2008/138920 A1).

The compound of formula XII where X can be nitrogen, R₁ can be hydrogen or trifluoromethyl, Y can be carbon and R₂ can be hydrogen, fluoro or methoxy can be prepared from the compound of formula XI where X can be nitrogen, R₁ can be hydrogen or trifluoromethyl, Y can be carbon and R₂ can be hydrogen, fluoro or methoxy under standard hydrogenation conditions (see for example, PCT WO2008/138920 A1).

The compound of formula XII where X can be carbon, R₁ can be chloro, Y can be carbon or nitrogen and R₂ can be hydrogen can be prepared from the compound of formula XI where X can be carbon, R₁ can be chloro, Y can be carbon or nitrogen and R₂ can be hydrogen under standard hydrogenation conditions (see for example, PCT WO2008/138920 A1).

The compound of formula XIII where X can be nitrogen, R₁ can be hydrogen or trifluoromethyl, Y can be carbon and R₂ can be hydrogen, fluoro or methoxy can be prepared from the compound of formula XII where X can be nitrogen, R₁ can be hydrogen or trifluoromethyl, Y can be carbon and R₂ can be hydrogen, fluoro or methoxy by treatment with methyl oxalylchloride (see for example, PCT WO2008/138920 A1).

The compound of formula XIII where X can be carbon, R₁ can be chloro, Y can be carbon and R₂ can be hydrogen can be prepared from the compound of formula XII where X can be carbon, R₁ can be chloro, Y can be carbon and R₂ can be hydrogen by treatment with methyl oxalylchloride (see for example, PCT WO2008/138920 A1).

The compound of formula XIV where X can be nitrogen, R₁ can be hydrogen or trifluoromethyl, Y can be carbon, R₂ can be hydrogen, fluoro or methoxy, R₃ can be methyl ester and Q can be hydrogen or methyl can be prepared from the compound of formula XIII where X can be nitrogen, $R_1$ can be hydrogen or trifluoromethyl, Y can be carbon and $R_2$ can be hydrogen, fluoro or methoxy by treatment with potassium carbonate in methanol (see for example, PCT WO2008/138920 A1).

The compound of formula XIV where X can be carbon, $R_1$ can be chloro, Y can be carbon, $R_2$ can be hydrogen, $R_3$ can be methyl ester and Q can be hydrogen or methyl can be prepared from the compound of formula XIII where X can be carbon, $R_1$ can be chloro, Y can be carbon and $R_2$ can be hydrogen by treatment with potassium carbonate in methanol (see for example, PCT WO2008/138920 A1).

The compound of formula XIV where X can be carbon, $R_1$ can be chloro, Y can be nitrogen, $R_2$ can be hydrogen, $R_3$ can be hydrogen and Q can be methyl can be prepared from the compound of formula XII where X can be carbon, $R_1$ can be chloro, Y can be nitrogen and $R_2$ can be hydrogen by treatment with the Vilsmeier reagent (see for example, Mendelson, W. L.; Hayden, S., *Syn. Comm.*, 1996, 26(3), 603-10).

The compound of formula XV where X can be nitrogen, $R_1$ can be hydrogen or trifluoromethyl, Y can be carbon, $R_2$ can be hydrogen, fluoro or methoxy and $R_3$ can be methyl ester can be prepared from the compound of formula XIV where X can be nitrogen, $R_1$ can be hydrogen or trifluoromethyl, Y can be carbon, $R_2$ can be hydrogen, fluoro or methoxy, $R_3$ can be methyl ester and Q can be methyl by hydrolysis of the benzoic methyl ester to the benzoic acid under standard hydrolysis reaction conditions (see for example, PCT WO2008/138920 A1).

The compound of formula XV where X can be carbon, $R_1$ can be chloro, Y can be carbon, $R_2$ can be hydrogen and $R_3$ can be methyl ester can be prepared from the compound of formula XIV where X can be carbon, $R_1$ can be chloro, Y can be carbon, $R_2$ can be hydrogen, $R_3$ can be methyl ester and Q can be methyl by hydrolysis of the benzoic methyl ester to the benzoic acid under standard hydrolysis reaction conditions (see for example, PCT WO2008/138920 A1).

The compound of formula XV where X can be carbon, $R_1$ can be chloro, Y can be nitrogen, $R_2$ can be hydrogen, $R_3$ can be hydrogen can be prepared from the compound of formula XIV where X can be carbon, $R_1$ can be chloro, Y can be nitrogen, $R_2$ can be hydrogen, $R_3$ can be hydrogen and Q can be methyl by hydrolysis of the benzoic methyl ester to the benzoic acid under standard hydrolysis reaction conditions (see for example, PCT WO2008/138920 A1).

The compound of formula XVI (cis isomer, trans isomer or a mixture thereof) can be prepared by known synthetic methods (see for example, PCT WO 2007/107470 A2). The compound of formula XVI, an amine, may be the free amine or a salt of the amine, such as the hydrochloride salt.

The compound of formula I where X can be nitrogen, $R_1$ can be hydrogen or trifluoromethyl, Y can be carbon, $R_2$ can be hydrogen, fluoro or methoxy and $R_3$ can be methyl ester can be prepared from the compound of formula XV where X can be nitrogen, $R_1$ can be hydrogen or trifluoromethyl, Y can be carbon, $R_2$ can be hydrogen, fluoro or methoxy and $R_3$ can be methyl ester by treatment with the compound of formula XVI under appropriate coupling conditions (see for example, PCT WO 2007/107470 A2).

The compound of formula I where X can be carbon, $R_1$ can be chloro, Y can be carbon, $R_2$ can be hydrogen and $R_3$ can be methyl ester can be prepared from the compound of formula XV where X can be carbon, $R_1$ can be chloro, Y can be carbon, $R_2$ can be hydrogen and $R_3$ can be methyl ester by treatment with the compound of formula XVI under appropriate coupling conditions (see for example, PCT WO 2007/107470 A2).

The compound of formula I where X can be carbon, $R_1$ can be chloro, Y can be nitrogen, $R_2$ can be hydrogen and $R_3$ can be hydrogen can be prepared from the compound of formula XV where X can be carbon, $R_1$ can be chloro, Y can be nitrogen, $R_2$ can be hydrogen and $R_3$ can be hydrogen by treatment with the compound of formula XVI under appropriate coupling conditions (see for example, PCT WO 2007/107470 A2).

The compound of formula XVII where X can be nitrogen, $R_1$ can be hydrogen or trifluoromethyl, Y can be carbon, $R_2$ can be hydrogen, fluoro or methoxy and $R_3$ can be methyl ester can be prepared from the compound of formula I where X can be nitrogen, $R_1$ can be hydrogen or trifluoromethyl, Y can be carbon, $R_2$ can be hydrogen, fluoro or methoxy and $R_3$ can be methyl ester by using standard conditions to convert a primary alcohol into a primary amine (see for example, Jirgensons, A., Kauss, V., Kalvinsh, I., Gold, M. R., *Synthesis*, 2000, 12, 1709-1712).

The compound of formula XVII where X can be carbon, $R_1$ can be chloro, Y can be carbon, $R_2$ can be hydrogen and $R_3$ can be a methyl ester can be prepared from the compound of formula I where X can be carbon, $R_1$ can be chloro, Y can be carbon, $R_2$ can be hydrogen and $R_3$ can be methyl ester by using standard conditions to convert a primary alcohol into a primary amine (see for example, Jirgensons, A., Kauss, V., Kalvinsh, I., Gold, M. R., *Synthesis*, 2000, 12, 1709-1712).

The compound of formula XVIII where $R_4$ can be an alkyl carboxyl moiety, X can be nitrogen, $R_1$ can be hydrogen, Y can be carbon, $R_2$ can be hydrogen and $R_3$ can be methyl ester can be prepared from the compound of formula XVII where X can be nitrogen, $R_1$ can be hydrogen, Y can be carbon, $R_2$ can be hydrogen and $R_3$ can be methyl ester using a standard procedure to acylate an amine (see for example, PCT WO2006/024627 A2). If the resulting compound contains a protecting group, the protecting group can be removed under standard deprotection conditions (see for example, Greene, T. W. *Protective Groups in Organic Synthesis*; John Wiley & Sons, Inc.: New York, 1991).

The compound of formula XVIII where $R_4$ can be an alkyl carboxyl moiety, X can be carbon, $R_1$ can be chloro, Y can be carbon, $R_2$ can be hydrogen and $R_3$ can be methyl ester can be prepared from the compound of formula XVII where X can be carbon, $R_1$ can be chloro, Y can be carbon, $R_2$ can be hydrogen and $R_3$ can be methyl ester using a standard procedure to acylate an amine (see for example, PCT WO2006/024627 A2). If the resulting compound contains a protecting group, the protecting group can be removed under standard deprotection conditions (see for example, Greene, T. W. *Protective Groups in Organic Synthesis*; John Wiley & Sons, Inc.: New York, 1991).

The compound of formula XVIII where $R_4$ can be an alkyl sulfonyl moiety, X can be nitrogen, $R_1$ can be hydrogen, Y can be carbon, $R_2$ can be hydrogen and $R_3$ can be methyl ester can be prepared from the compound of formula XVII where X can be nitrogen, $R_1$ can be hydrogen, Y can be carbon, $R_2$ can be hydrogen and $R_3$ can be methyl ester using a standard procedure to sulfonylate an amine (see for example, PCT WO2006/024627 A2). If the resulting sulfonylated compound contains a protecting group, the protecting group can be removed under standard deprotection conditions (see for example, Greene, T. W. *Protective Groups in Organic Synthesis*; John Wiley & Sons, Inc.: New York, 1991).

The compound of formula XVIII where $R_4$ can be an alkyl sulfonyl moiety, X can be carbon, $R_1$ can be chloro, Y can be carbon, $R_2$ can be hydrogen and $R_3$ can be methyl ester can be prepared from the compound of formula XVII where X can be carbon, $R_1$ can be chloro, Y can be carbon, $R_2$ can be hydrogen and $R_3$ can be methyl ester using a standard procedure to sulfonylate an amine (see for example, PCT WO2006/024627 A2). If the resulting sulfonylated compound contains a protecting group, the protecting group can be removed under standard deprotection conditions (see for example, Greene, T. W. *Protective Groups in Organic Synthesis*; John Wiley & Sons, Inc.: New York, 1991).

The compound of formula XVIII where $R_4$ can be an alkyl moiety, X can be nitrogen, $R_1$ can be hydrogen, Y can be carbon, $R_2$ can be hydrogen and $R_3$ can be methyl ester can be prepared from the compound of formula XVII where X can be nitrogen, $R_1$ can be hydrogen, Y can be carbon, $R_2$ can be hydrogen and $R_3$ can be methyl ester using a standard procedure to alkylate an amine (see for example, PCT WO2006/024627 A2). If the resulting compound contains a protecting group, the protecting group can be removed under standard deprotection conditions (see for example, Greene, T. W. *Protective Groups in Organic Synthesis*; John Wiley & Sons, Inc.: New York, 1991).

The compound of formula XVIII where $R_4$ can be an alkyl moiety, X can be carbon, $R_1$ can be chloro, Y can be carbon, $R_2$ can be hydrogen and $R_3$ can be methyl ester can be prepared from the compound of formula XVII where X can be carbon, $R_1$ can be chloro, Y can be carbon, $R_2$ can be hydrogen and $R_3$ can be methyl ester using a standard procedure to alkylate an amine (see for example, PCT WO2006/024627 A2). If the resulting compound contains a protecting group, the protecting group can be removed under standard deprotection conditions (see for example, Greene, T. W. *Protective Groups in Organic Synthesis*; John Wiley & Sons, Inc.: New York, 1991).

The compound of formula XVIII where $R_4$ can be an alkyl moiety, X can be nitrogen, $R_1$ can be hydrogen, Y can be carbon, $R_2$ can be hydrogen and $R_3$ can be methyl ester can be prepared from the compound of formula XVII where X can be nitrogen, $R_1$ can be hydrogen, Y can be carbon, $R_2$ can be hydrogen and $R_3$ can be methyl ester under epoxide ring opening conditions (see for example, Calet, S., Urso, F., Alper, H., *J. Amer. Chem. Soc.*, 1989, 111, 931-934). If the resulting compound contains a protecting group, the protecting group can be removed under standard deprotection conditions (see for example, Greene, T. W. *Protective Groups in Organic Synthesis*; John Wiley & Sons, Inc.: New York, 1991).

The compound of formula XVIII where $R_4$ can be an alkyl moiety, X can be carbon, $R_1$ can be chloro, Y can be carbon, $R_2$ can be hydrogen and $R_3$ can be methyl ester can be prepared from the compound of formula XVII where X can be carbon, $R_1$ can be chloro, Y can be carbon, $R_2$ can be hydrogen and $R_3$ can be methyl ester under epoxide ring opening conditions (see for example, Calet, S., Urso, F., Alper, H., *J. Amer. Chem. Soc.*, 1989, 111, 931-934). If the resulting compound contains a protecting group, the protecting group can be removed under standard deprotection conditions (see for example, Greene, T. W. *Protective Groups in Organic Synthesis*; John Wiley & Sons, Inc.: New York, 1991).

The compound of formula XIX where $R_5$ can be acetyl, X can be carbon, $R_1$ can be chloro, Y can be carbon, $R_2$ can be hydrogen and $R_3$ can be methyl ester can be prepared from the compound of formula I where X can be carbon, $R_1$ can be chloro, Y can be carbon, $R_2$ can be hydrogen and $R_3$ can be methyl ester under the Ritter reaction conditions (see for example, Jirgensons, A., Kauss, V., Kalvinsh, I., Gold, M. R., *Synthesis*, 2000, 12, 1709-1712)

The compound of formula XXI where $R_1$ can be chloro can be prepared from commercially available starting materials, such as 2-bromo-4-chlorobenzoic acid, using standard metal catalyzed aryl halide displacement conditions (see for example, PCT WO2008/138920 A1).

The compound of formula XXII where $R_1$ can be chloro can be prepared from the compound of formula XXI where $R_1$ can be chloro by treatment with N,O-dimethyl hydroxylamine hydrochloride under appropriate coupling conditions (see for example, PCT WO2008/138920 A1).

The compound of formula XXIII where $R_1$ can be chloro can be prepared from the compound of formula XXII where $R_1$ can be chloro by treatment with an appropriate Grignard reagent (see for example, PCT WO2008/138920 A1).

The compound of formula XXIV where $R_1$ can be chloro can be prepared from the compound of formula XXIII where $R_1$ can be chloro by treatment with methyl oxalylchloride (see for example, PCT WO2008/138920 A1).

The compound of formula XXV where $R_1$ can be chloro can be prepared from the compound of formula XXIV where $R_1$ can be chloro by treatment with potassium carbonate in methanol (see for example, PCT WO2008/138920 A1).

The compound of formula XXVI where $R_1$ can be chloro can be prepared from the compound of formula XXV where $R_1$ can be chloro under standard radical bromination condition (see for example, see for example, Gauuan, P. J. F, Trova, M. P., Gregor-Boros, L., Bocckino, S. B., Crapo, J. D., and Day, B. J., *Bioorg. Med. Chem.*, 2002, 10, 3013-3021).

The compound of formula XXVII where $R_1$ can be chloro can be prepared from the compound of formula XXVI where $R_1$ can be chloro by treatment with the appropriate nucleophile under basic conditions (see for example, WO 2008/041075)

The compound of formula XXVIII where $R_1$ can be chloro can be prepared from the compound of formula XXVII where $R_1$ can be chloro by hydrolysis of the benzoic methyl ester to the benzoic acid under standard hydrolysis reaction conditions (see for example, PCT WO2008/138920 A1).

The compound of formula XXIX where $R_1$ can be chloro can be prepared from the compound of formula XXVIII where $R_1$ can be chloro by treatment with the compound of formula XVI under appropriate coupling conditions (see for example, PCT WO 2007/107470 A2).

Scheme 3

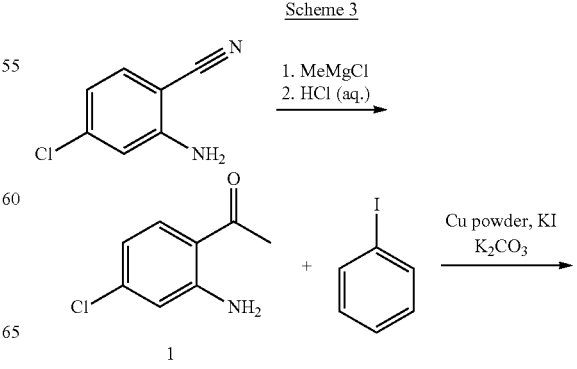

1

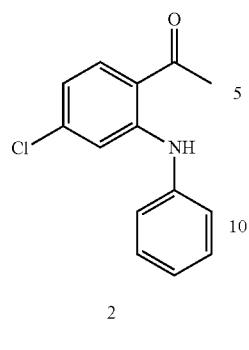

Compound 2 can be synthesized following the reaction outlined in Scheme 3. Commercially available 2-amino-4-chloro-benzonitrile can be treated under standard Grignard conditions followed by acidic workup to afford compound 1 (see for example, PCT WO2005/097800). The amino group of compound 1 can be coupled with the aryl iodide under standard metal catalyzed coupling conditions to afford compound 2 (see for example, PCT WO2008/138920 A1).

Scheme 4

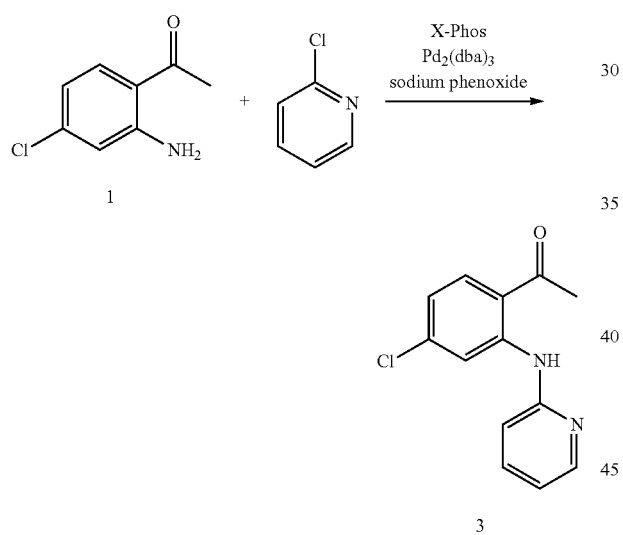

Compound 3 can be synthesized following the reaction outlined in Scheme 4. The amino group of compound 1 can be coupled through the chloro substitution of 2-chloropyridine under standard metal catalyzed coupling conditions to afford compound 3 (see for example, Yin, J., Zhao, M. M., Huffman, M. A., McNamara, J. M., *Org. Lett.*, 2002, 4(20), 3881-3484).

Scheme 5

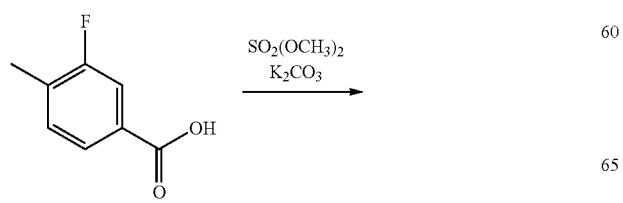

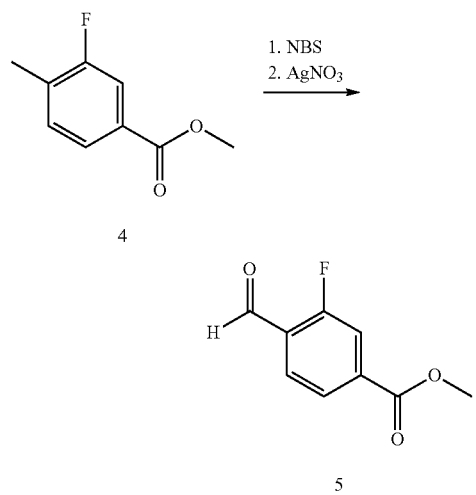

Compound 5 can be synthesized following the reactions outlined in Scheme 5. Commercially available 3-fluoro-4-methyl-benzoic acid can be converted to the methyl benzoate under standard conditions to form a methyl ester (see for example, Gauuan, P. J. F, Trova, M. P., Gregor-Boros, L., Bocckino, S. B., Crapo, J. D., and Day, B. J., *Bioorg. Med. Chem.*, 2002, 10, 3013-3021). The methyl group adjacent to the fluoro substituent of compound 4 can be brominated using standard radical bromination conditions (see for example, Gauuan, P. J. F, Trova, M. P., Gregor-Boros, L., Bocckino, S. B., Crapo, J. D., and Day, B. J., *Bioorg. Med. Chem.*, 2002, 10, 3013-3021) and then converted to the corresponding aldehyde using such reagents as silver nitrate (see for example, Gauuan, P. J. F, Trova, M. P., Gregor-Boros, L., Bocckino, S. B., Crapo, J. D., and Day, B. J., *Bioorg. Med. Chem.*, 2002, 10, 3013-3021).

Scheme 6

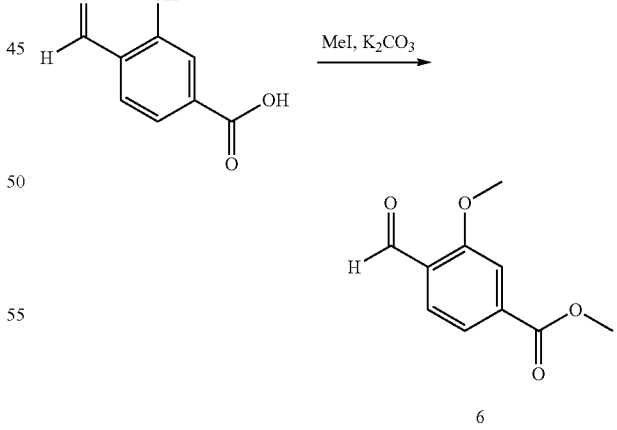

Compound 6 can be synthesized following the reactions outlined in Scheme 6. Commercially available 4-formyl-3-hydroxy-benzoic acid can be converted to compound 6 under standard methylation conditions (see for example, Adediran, S. A., Cabaret, D., Drouillat, B., Pratt, R. F., Wakselman, M., *Bioorg. Med. Chem.*, 2001, 9, 1175-1183).

Scheme 7
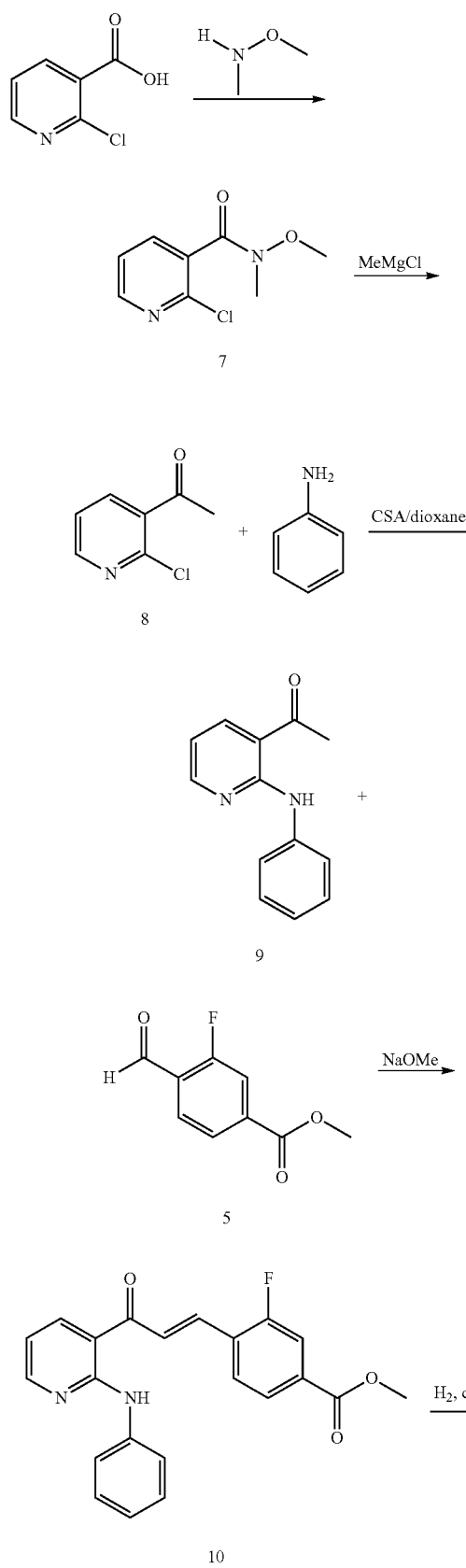
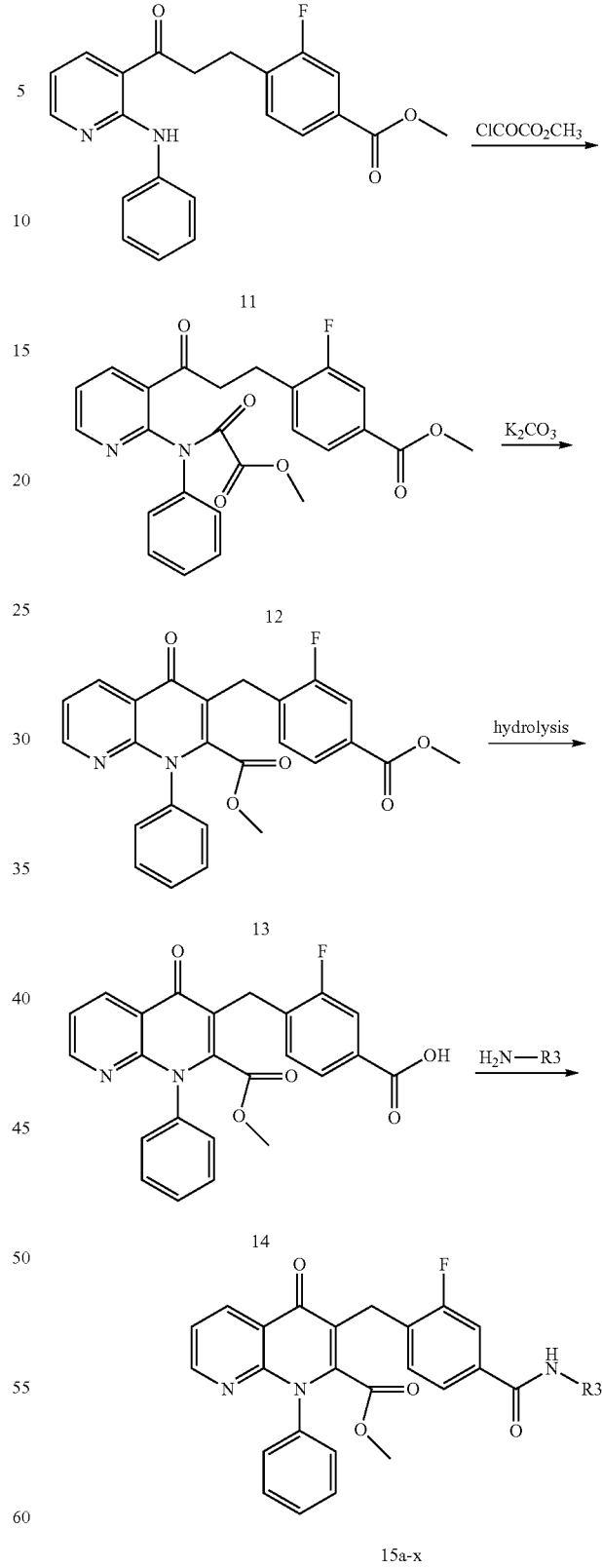
Compound 15a-x can be synthesized following the reactions outlined in Scheme 7. Commercially available 2-chloronicotinic acid can be treated with N,O-hydroxylamine hydrochloride under standard coupling conditions to form the Weinreb amide, compound 7 (see for example, PCT WO2008/138920 A1). Compound 7 can be treated with methyl magnesium chloride under standard Grignard conditions to provide compound 8 (see for example, PCT WO2008/138920 A1). Compound 8 can be treated with aniline under standard displacement conditions to provide compound 9 (see for example, PCT WO2008/138920 A1). The resulting ketone, compound 9, can then be treated with aldehyde 5 under standard aldol condensation conditions to provide the olefin, compound 10 (see for example, PCT WO2008/138920 A1). The olefin, compound 10, may then be reduced under standard hydrogenation conditions to provide the saturated system, compound 11 (see for example, PCT WO2008/138920 A1). Compound 11 may then be treated with methyl oxalylchloride to give compound 12 (see for example, PCT WO2008/138920 A1). The methyl oxalylate, compound 12, may then be cyclized using potassium carbonate to give compound 13 (see for example, PCT WO2008/138920 A1). If the benzoate of the cyclized product, compound 13, did not already hydrolyze during the reaction conditions used to affect the cyclization, compound 13 may be treated under standard hydrolysis conditions to form the corresponding benzoic acid derivative, compound 14 (see for example, PCT WO2008/138920 A1). The resulting benzoic acid, compound 14, in the presence of appropriate amines may then be treated under standard amide bond forming conditions to afford compounds 15a-x (see for example, PCT WO2008/138920 A1).

Scheme 8

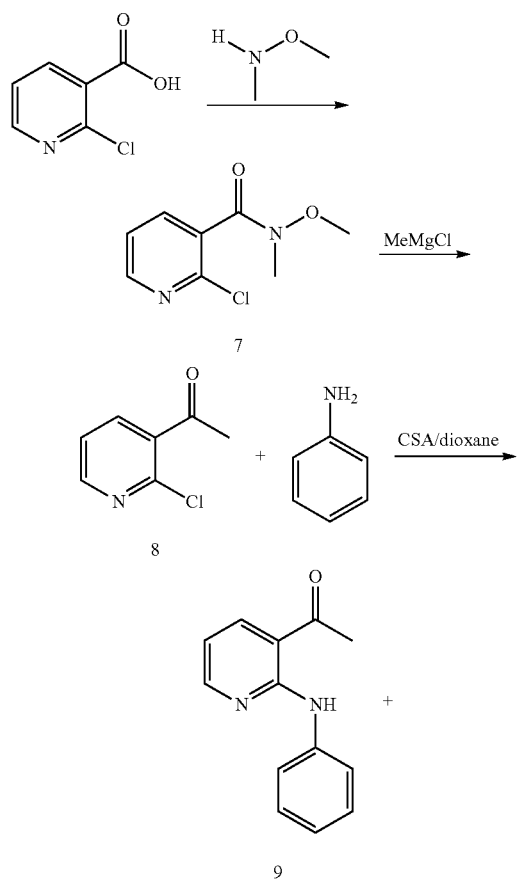

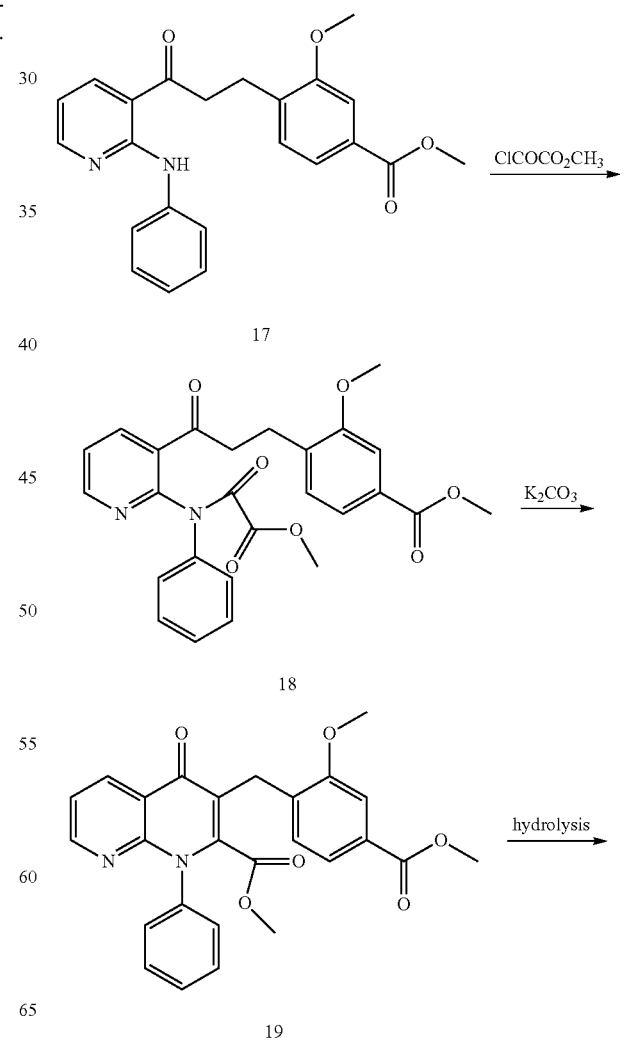

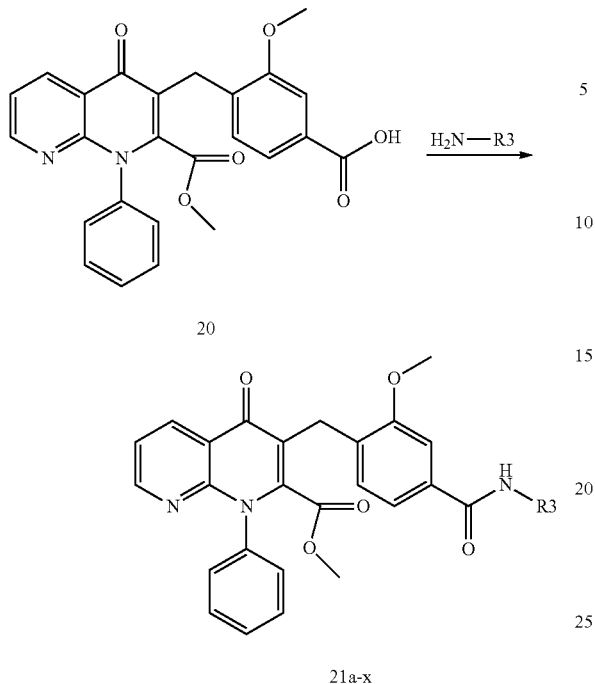

20

21a-x

Scheme 9

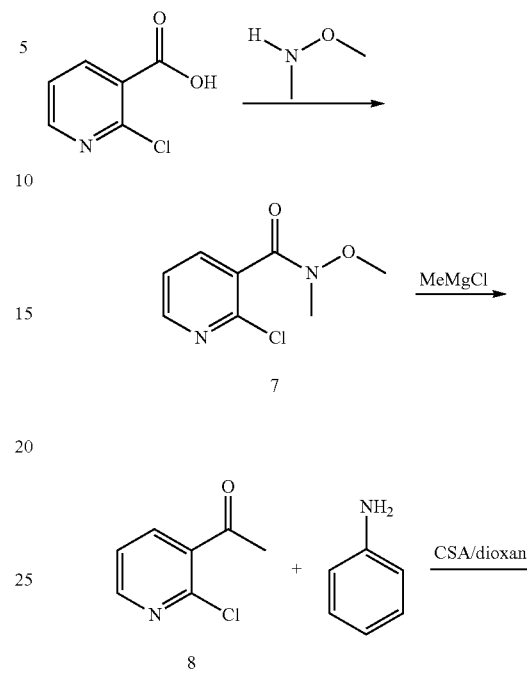

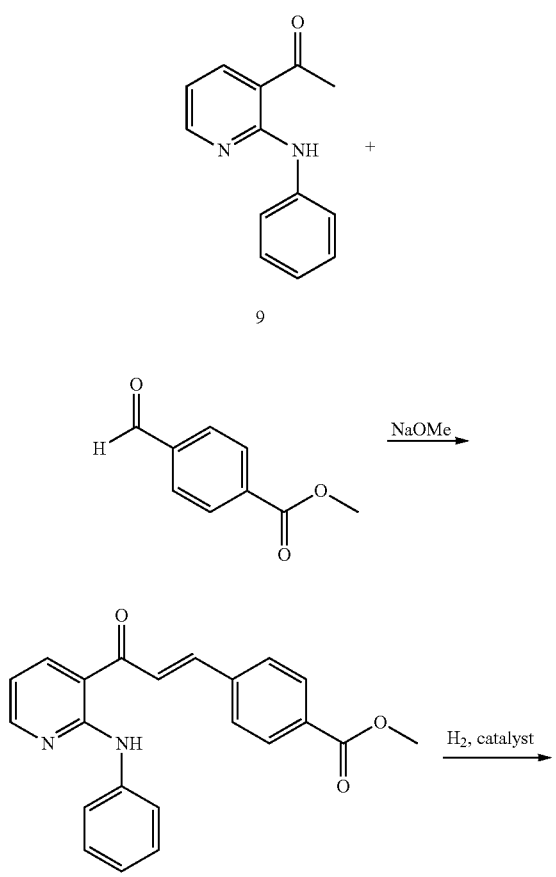

Compound 21a-x can be synthesized following the reactions outlined in Scheme 8. Commercially available 2-chloronicotinic acid can be treated with N,O-hydroxylamine hydrochloride under standard coupling conditions to form the Weinreb amide, compound 7 (see for example, PCT WO2008/138920 A1). Compound 7 can be treated with methyl magnesium chloride under standard Grignard conditions to provide compound 8 (see for example, PCT WO2008/138920 A1). Compound 8 can be treated with aniline under standard displacement conditions to produce compound 9 (see for example, PCT WO2008/138920 A1). The resulting ketone, compound 9, can then be treated with aldehyde 6 under standard aldol condensation conditions to provide the olefin, compound 16 (see for example, PCT WO2008/138920 A1). The olefin, compound 16, may then be reduced under standard hydrogenation conditions to provide compound 17 (see for example, PCT WO2008/138920 A1). Compound 17 may then be treated with methyl oxalylchloride to give compound 18 (see for example, PCT WO2008/138920 A1). The methyl oxalylate, compound 18, may then be cyclized using potassium carbonate to give compound 19 (see for example, PCT WO2008/138920 A1). If the benzoate of the cyclized product, compound 19, did not already hydrolyze during the reaction conditions used to affect the cyclization, compound 19 may be treated under standard hydrolysis conditions to form the corresponding benzoic acid derivative, compound 20 (see for example, PCT WO2008/138920 A1). The resulting benzoic acid, compound 20, in the presence of appropriate amines may then be treated under standard amide bond forming conditions to afford compounds 21a-x (see for example, PCT WO2008/138920 A1).

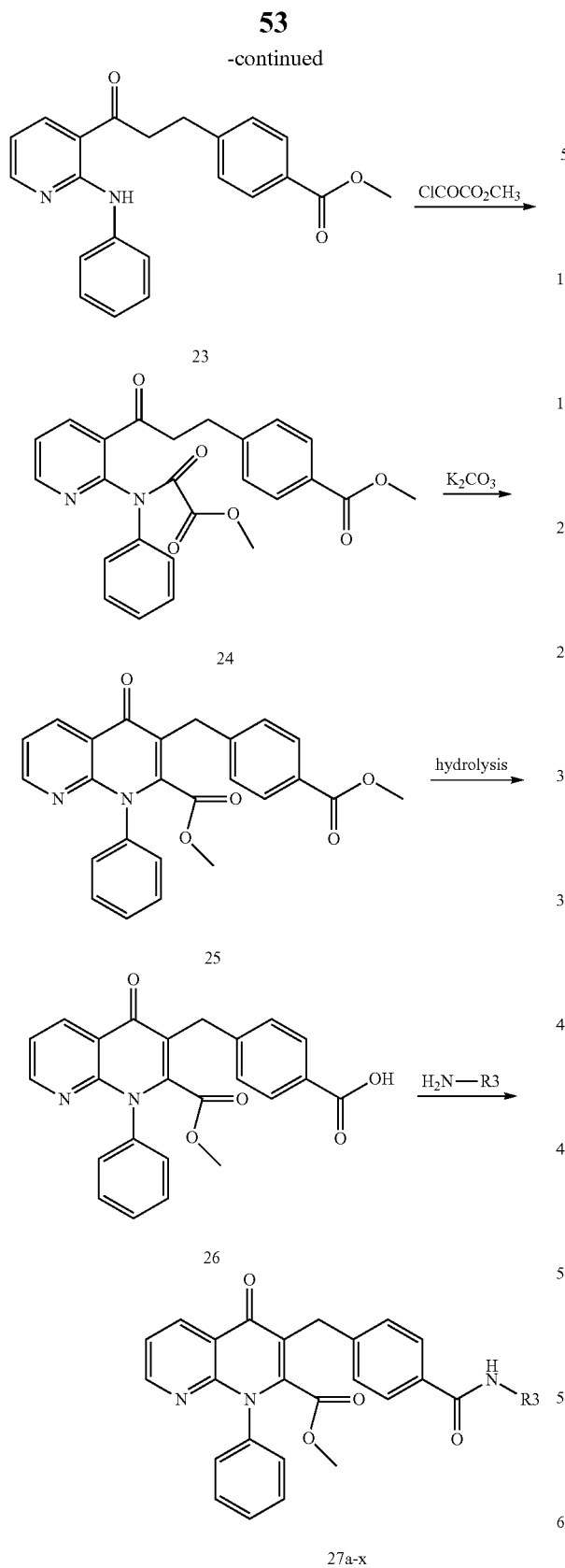

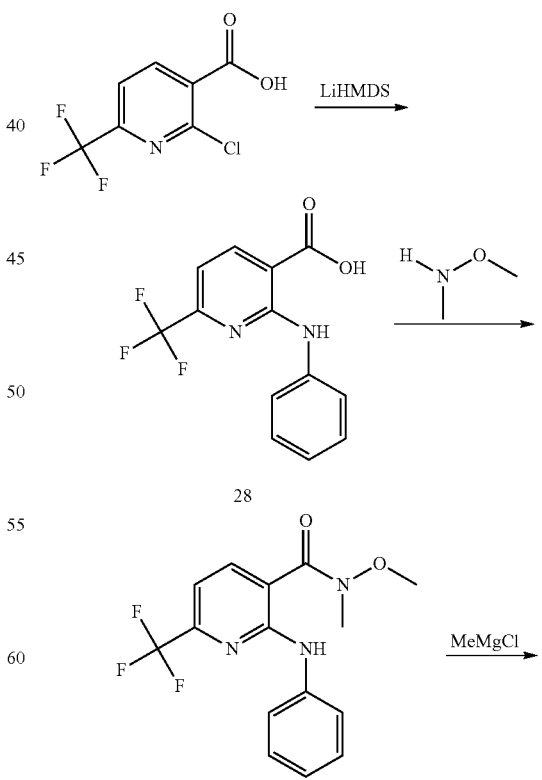

Weinreb amide, compound 7 (see for example, PCT WO2008/138920 A1). Compound 7 can be treated with methyl magnesium bromide under standard Grignard conditions to provide compound 8 (see for example, PCT WO2008/138920 A1). Compound 8 can be treated with aniline under standard displacement conditions to produce compound 9 (see for example, PCT WO2008/138920 A1). The resulting ketone, compound 9, can then be treated with commercially available methyl-4-formylbenzoate under standard aldol condensation conditions to provide the olefin, compound 22 (see for example, PCT WO2008/138920 A1). The olefin, compound 22, may then be reduced under standard hydrogenation conditions to provide compound 23 (see for example, PCT WO2008/138920 A1). Compound 23 may then be treated with methyl oxalylchloride to give compound 24 (see for example, PCT WO2008/138920 A1). The methyl oxylate, compound 24, may then be cyclized using potassium carbonate to give compound 25 (see for example, PCT WO2008/138920 A1). If the benzoate of the cyclized product, compound 25, did not already hydrolyze during the reaction conditions used to affect the cyclization, compound 25 may be treated under standard hydrolysis conditions to form the corresponding benzoic acid derivative, compound 26 (see for example, PCT WO2008/138920 A1). The resulting benzoic acid, compound 26, in the presence of appropriate amines may then be treated under standard amide bond forming conditions to afford compounds 27a-x (see for example, PCT WO2008/138920 A1).

Compound 27a-x can be synthesized following the reactions outlined in Scheme 9. Commercially available 2-chloronicotinic acid can be treated with N,O-hydroxylamine hydrochloride under standard coupling conditions to form the

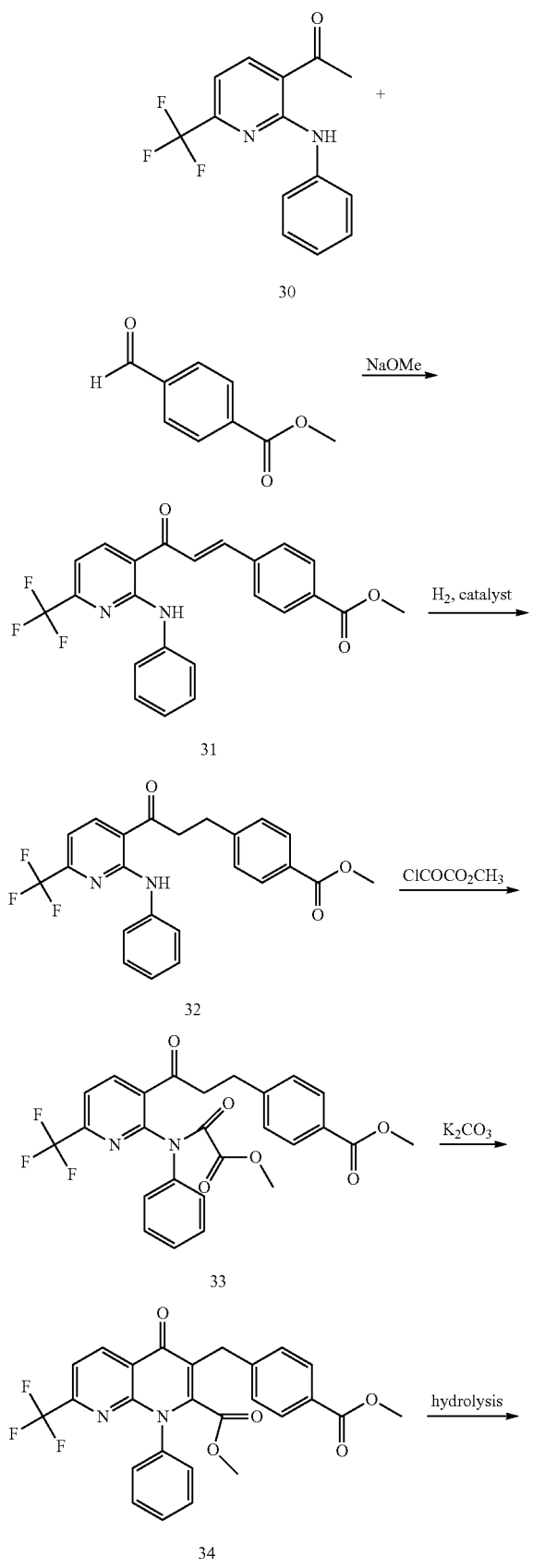

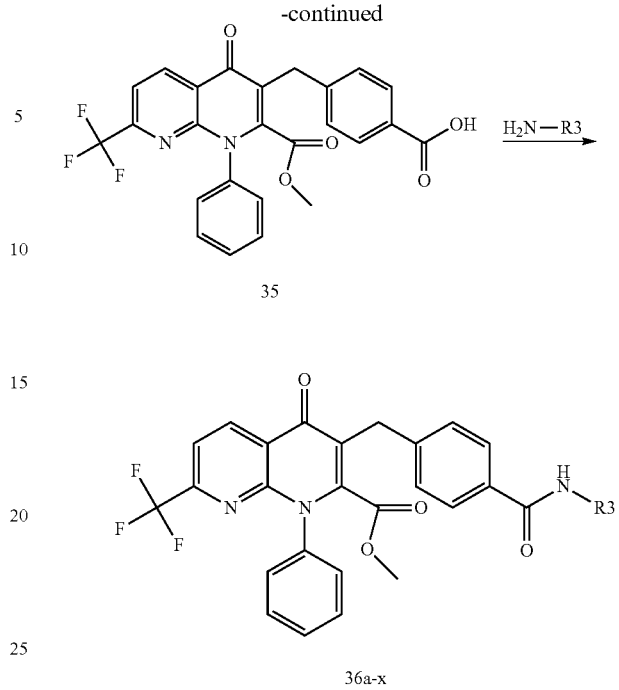

Compound 36a-x can be synthesized following the reactions outlined in Scheme 10. Commercially available 2-chloro-6-trifluoromethyl-nicotinic acid can be treated under standard halide displacement conditions to provide compound 28 (see for example, PCT WO2008/138920 A1). Compound 28 can be treated with N,O-hydroxylamine hydrochloride under standard coupling conditions to form the Weinreb amide, compound 29 (see for example, PCT WO2008/138920 A1). Compound 29 can be treated with methyl magnesium chloride under standard Grignard conditions to provide compound 30 (see for example, PCT WO2008/138920 A1). The resulting ketone, compound 30, can then be treated with commercially available 4-formyl-methylbenzoate under standard aldol condensation conditions to provide the olefin, compound 31 (see for example, PCT WO2008/138920 A1). The olefin, compound 31, may then be reduced under standard hydrogenation conditions to provide compound 32 (see for example, PCT WO2008/138920 A1). Compound 32 may then be treated with methyl oxalyl chloride to give compound 33 (see for example, PCT WO2008/138920 A1). The methyl oxalylate, compound 33, may then be cyclized using potassium carbonate to give compound 34 (see for example, PCT WO2008/138920 A1). If the benzoate of the cyclized product, compound 34, did not already hydrolyze during the reaction conditions used to affect the cyclization, compound 34 may be treated under standard hydrolysis conditions to form the corresponding benzoic acid derivative, compound 35 (see for example, PCT WO2008/138920 A1). The resulting benzoic acid, compound 35, in the presence of appropriate amines may then be treated under standard amide bond forming conditions to afford compounds 36a-x (see for example, PCT WO2008/138920 A1).

Scheme 11

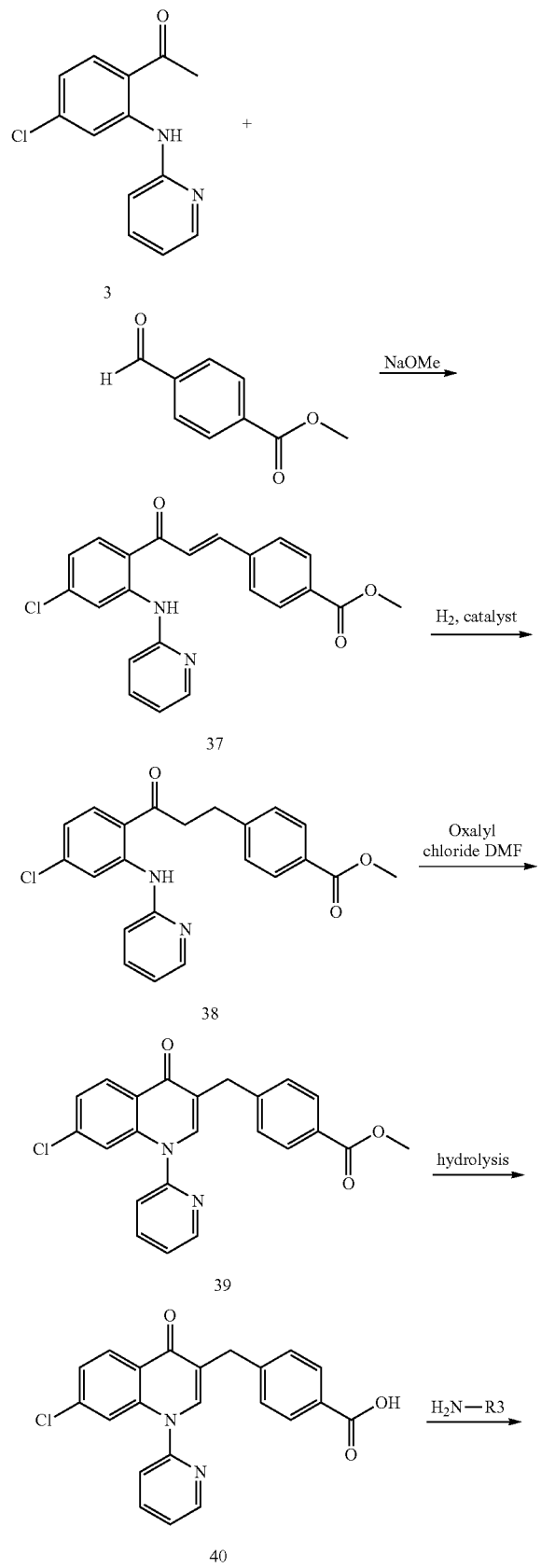

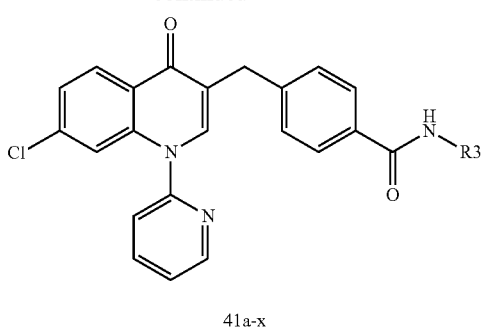

41a-x

Compound 41a-x can be synthesized following the reactions outlined in Scheme 11. Compound 3 can be treated with commercially available 4-formyl-benzoic acid methyl ester under standard aldol condensation conditions to provide the olefin, compound 37 (see for example, PCT WO2008/138920 A1). The olefin, compound 37, may then be reduced under standard hydrogenation conditions to provide compound 38 (see for example, PCT WO2008/138920 A1). Compound 38 may then be treated with the Vilsmeier reagent to give compound 39 (see for example, Mendelson, W. L.; Hayden, S., *Syn. Comm.*, 1996, 26(3), 603-10). The methyl ester of compound 39 may be treated under standard hydrolysis conditions to form the corresponding benzoic acid derivative, compound 40 (see for example, PCT WO2008/138920 A1). The resulting benzoic acid, compound 40, in the presence of appropriate amines may then be treated under standard amide bond forming conditions to afford compounds 41a-x (see for example, PCT WO2008/138920 A1).

Scheme 12

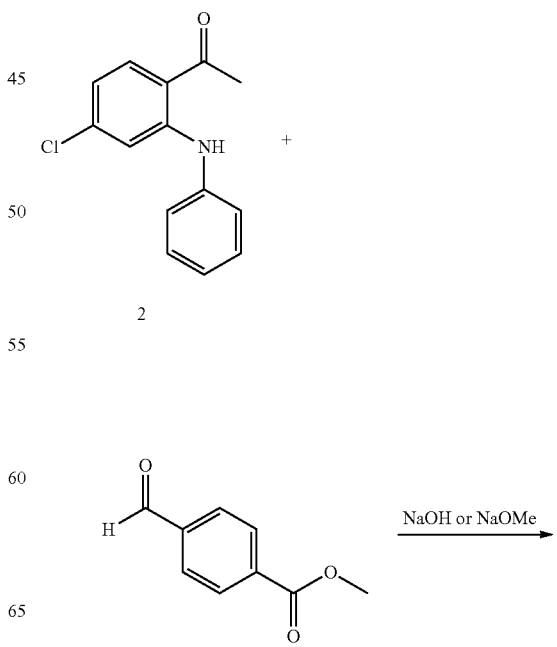

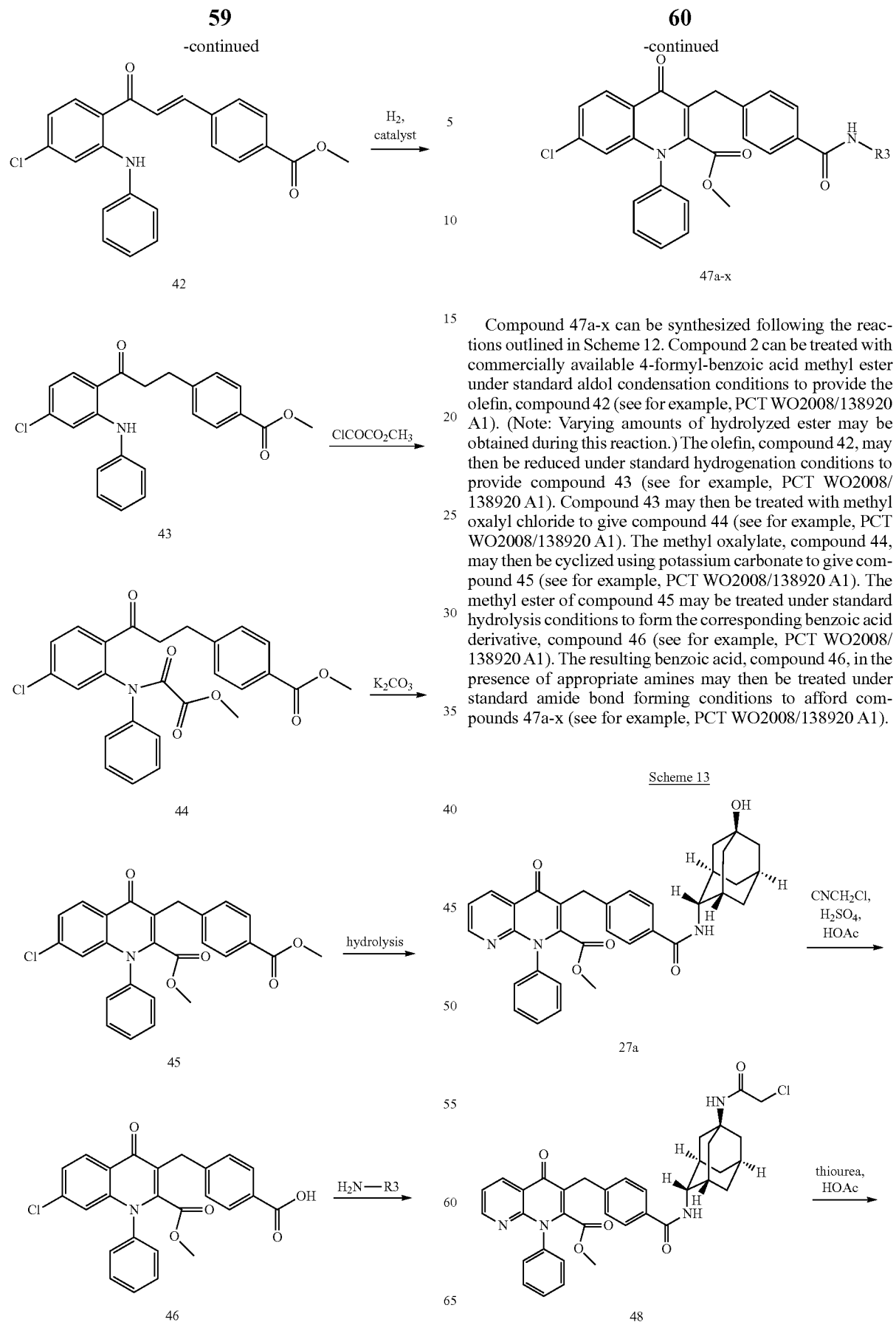

Compound 47a-x can be synthesized following the reactions outlined in Scheme 12. Compound 2 can be treated with commercially available 4-formyl-benzoic acid methyl ester under standard aldol condensation conditions to provide the olefin, compound 42 (see for example, PCT WO2008/138920 A1). (Note: Varying amounts of hydrolyzed ester may be obtained during this reaction.) The olefin, compound 42, may then be reduced under standard hydrogenation conditions to provide compound 43 (see for example, PCT WO2008/138920 A1). Compound 43 may then be treated with methyl oxalyl chloride to give compound 44 (see for example, PCT WO2008/138920 A1). The methyl oxalylate, compound 44, may then be cyclized using potassium carbonate to give compound 45 (see for example, PCT WO2008/138920 A1). The methyl ester of compound 45 may be treated under standard hydrolysis conditions to form the corresponding benzoic acid derivative, compound 46 (see for example, PCT WO2008/138920 A1). The resulting benzoic acid, compound 46, in the presence of appropriate amines may then be treated under standard amide bond forming conditions to afford compounds 47a-x (see for example, PCT WO2008/138920 A1).

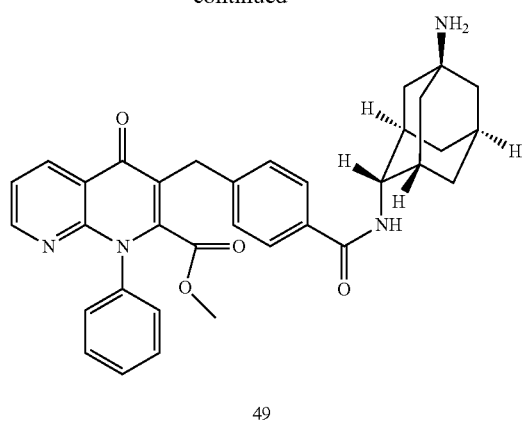

49

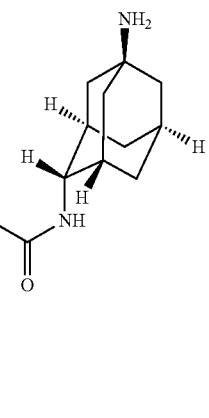

51

Compound 49 can be synthesized following the reactions outlined in Scheme 13. Compound 27a can be treated under standard Ritter reaction conditions to affect the conversion to the chloro acetyl amine, compound 48 (see for example, Jirgensons, A., Kauss, V., Kalvinsh, I., Gold, M. R., *Synthesis*, 2000, 12, 1709-1712). Compound 48 can then be treated under the appropriate conditions to afford compound 49 (see for example, Jirgensons, A., Kauss, V., Kalvinsh, I., Gold, M. R., *Synthesis*, 2000, 12, 1709-1712). Compound 49 can be converted into the appropriate salt, such as hydrochloric acid salt, by treatment with a solution containing the appropriate acid followed by concentration of the resulting solution.

Compound 51 can be synthesized following the reactions outlined in Scheme 14. Compound 47a can be treated under standard Ritter reaction conditions to affect the conversion to the chloro acetyl amine, compound 50 (see for example, Jirgensons, A., Kauss, V., Kalvinsh, I., Gold, M. R., *Synthesis*, 2000, 12, 1709-1712). Compound 50 can then be treated under the appropriate conditions to afford compound 51 (see for example, Jirgensons, A., Kauss, V., Kalvinsh, I., Gold, M. R., *Synthesis*, 2000, 12, 1709-1712). Compound 51 can be converted into the appropriate salt, such as hydrochloric acid salt, by treatment with a solution containing the appropriate acid followed by concentration of the resulting solution.

Scheme 14

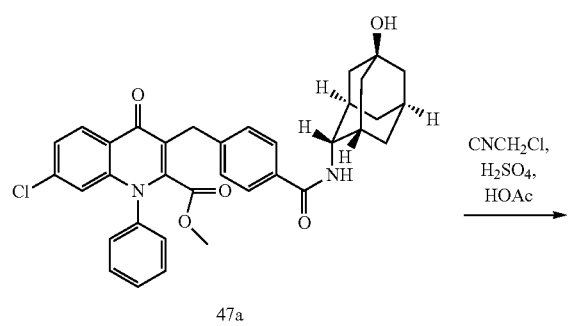

Scheme 15

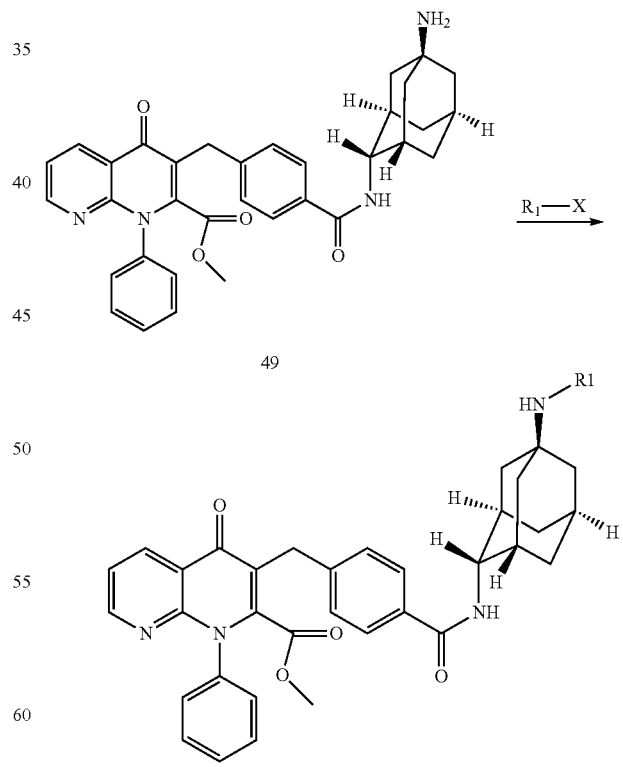

Compounds 52a-x can be synthesized following the reactions outlined in Scheme 15. Compound 49 can be treated under alkylation, acylation or sulfonylation conditions to produce compounds 52a-x (see for example, PCT WO2006/024627 A2). Compound 49 can also be treated under epoxide ring opening conditions to produce compounds 52a-x (see for example, Calet, S., Urso, F., Alper, H., *J. Amer. Chem. Soc.*, 1989, 111, 931-934). Final deprotection or chemical conversion of compounds 52a-x may be required to produce the desired final compound.

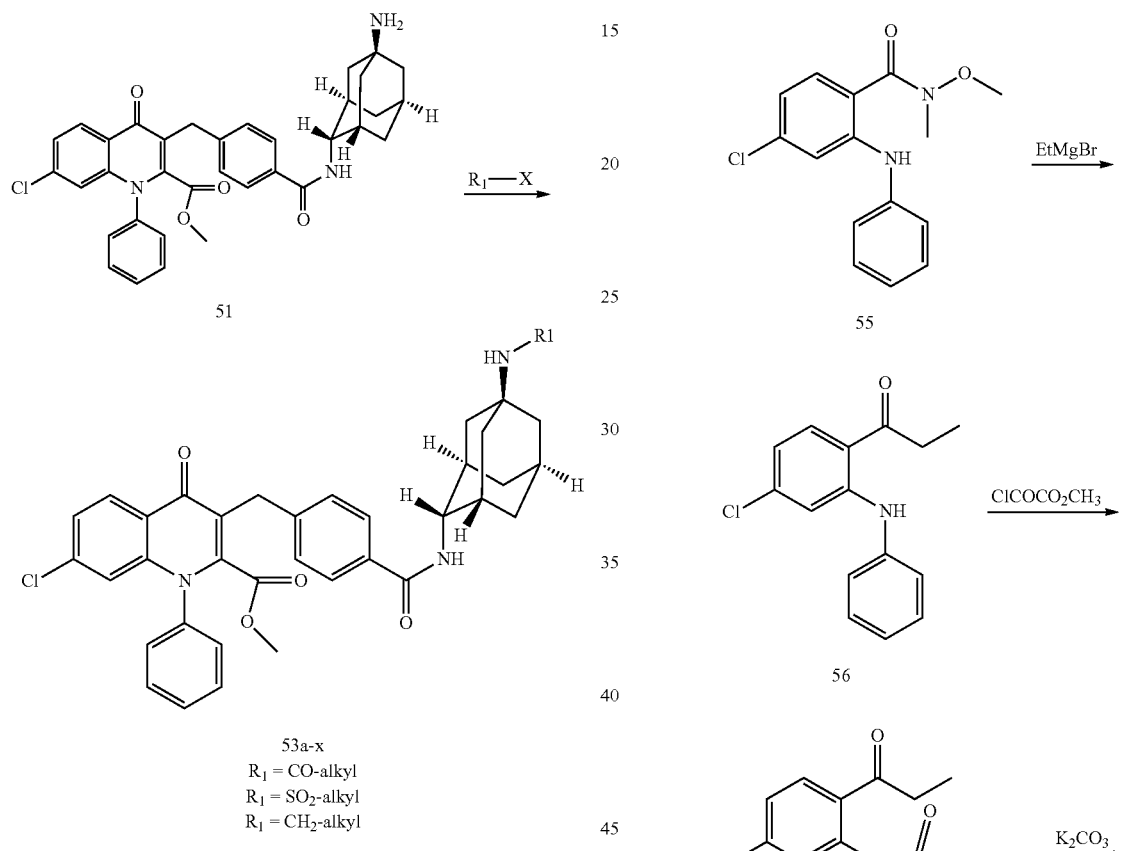

Scheme 16

53a-x
R₁ = CO-alkyl
R₁ = SO₂-alkyl
R₁ = CH₂-alkyl

Compounds 53a-x can be synthesized following the reactions outlined in Scheme 16. Compound 51 can be treated under alkylation, acylation or sulfonylation conditions to produce compounds 53a-x (see for example, PCT WO2006/024627 A2). Compound 51 can also be treated under epoxide ring opening conditions to produce compounds 53a-x (see for example, Calet, S., Urso, F., Alper, H., *J. Amer. Chem. Soc.*, 1989, 111, 931-934). Final deprotection or chemical conversion of compounds 53a-x may be required to produce the desired final compound.

Scheme 17

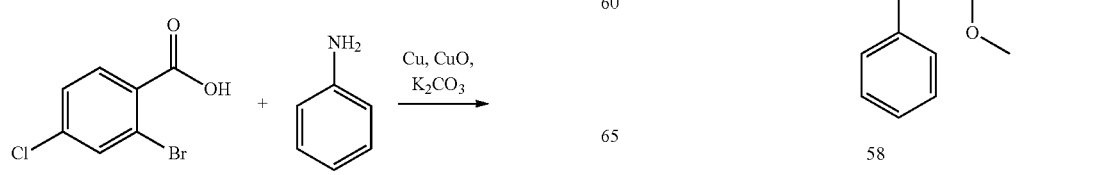

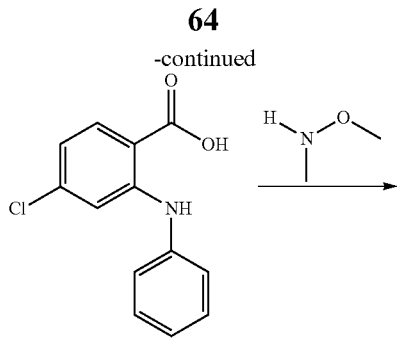

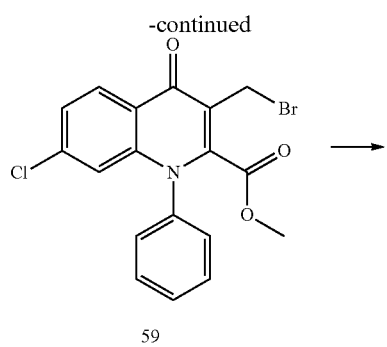
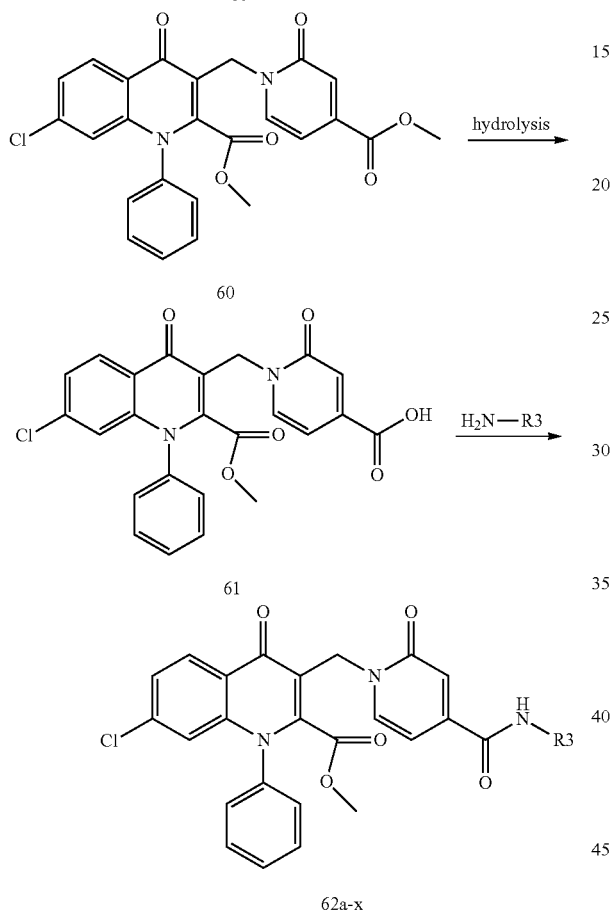

Gregor-Boros, L., Bocckino, S. B., Crapo, J. D., and Day, B. J., *Bioorg. Med. Chem.*, 2002, 10, 3013-3021). Compound 59 may then be treated with an appropriate nucleophile under basic conditions to provide compound 60 (see for example, WO 2008/041075). The methyl ester of compound 60 may be treated under standard hydrolysis conditions to form the corresponding benzoic acid derivative, compound 61 (see for example, WO 2008/138920 A1). The resulting benzoic acid, compound 61, in the presence of appropriate amines may then be treated under standard amide bond forming conditions to afford compounds 62a-x (see for example, WO 2008/138920 A1).

Scheme 18

Compound 62a-x can be synthesized following the reactions outlined in Scheme 17. Commercially available 2-bromo-4-chlorobenzoic acid can be treated with aniline under standard metal catalyzed aryl halide displacement conditions to provide compound 54 (see for example, PCT WO2008/138920 A1). Compound 54 can be treated with N,O-hydroxylamine hydrochloride under standard coupling conditions to form the Weinreb amide, compound 55 (see for example, PCT WO2008/138920 A1). Compound 55 can be treated with ethyl magnesium bromide under standard Grignard conditions to provide compound 56 (see for example, PCT WO2008/138920 A1). Compound 56 may then be treated with methyl oxalyl chloride to give compound 57 (see for example, PCT WO2008/138920 A1). The methyl oxalylate, compound 57, may then be cyclized using potassium carbonate to give compound 58 (see for example, PCT WO2008/138920 A1). Compound 58 may then be treated under standard radical bromination condition to provide compound 59 (see for example, Gauuan, P. J. F, Trova, M. P., Compound 63 can be synthesized following the reactions outlined in Scheme 18. Compound 47a can be treated under standard Ritter reaction conditions to afford compound 63 (see for example, Jirgensons, A., Kauss, V., Kalvinsh, I., Gold, M. R., *Synthesis*, 2000, 12, 1709-1712).

Scheme 19

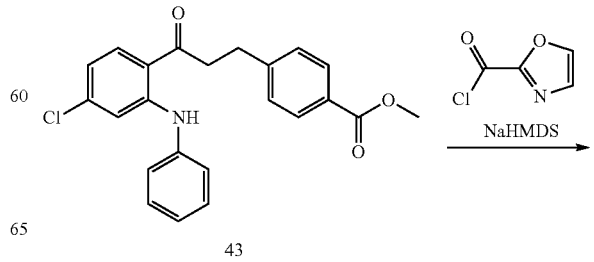

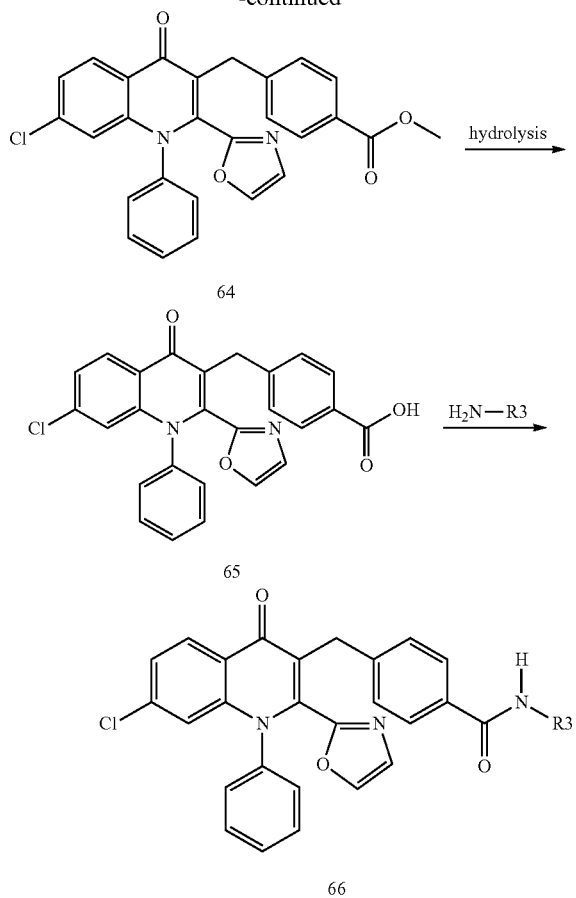

Compound 66 can be synthesized following the reactions outlined in Scheme 19. Compound 43 can be treated with 2-oxazole carbonyl chloride and sodium hexamethyldisilazane to provide quinolone 64 (see for example, PCT WO2008/138920 A1). The methyl ester of compound 64 may be treated under standard hydrolysis conditions to form the corresponding benzoic acid derivative, compound 65. The resulting benzoic acid, compound 65, in the presence of appropriate amines may then be treated under standard amide bond forming conditions to afford compound 66 (see for example, PCT WO2008/138920 A1).

Pharmaceutical Compositions and Administration

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use.

Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxy-methylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may also be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chloro-fluorocarbon (CFC), for example, dichlorodifluoromethane, trichlorofluoromethane, or dichloro-tetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacyclo-heptan-2-one). Sustained release delivery systems are inserted subcutaneously into the sub-dermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Pharmaceutical compositions of the subject Compounds for administration via several routes are prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Additional objects, advantages, and novel features of this invention will become apparent to those skilled in the art upon examination of the following examples thereof, which are not intended to be limiting.

Indications and Methods of Treatment

The compounds of this invention are JNK inhibitors and as such are expected to be effective in the treatment of a wide range of JNK mediated disorders. Exemplary JNK mediated disorders include, but are not limited to, kidney disease, autoimmune disorders, inflammatory disorders, metabolic disorders, neurological disease, and cancer. Accordingly, compounds of the invention can be used to treat one or more of such disorders. In some embodiments, compounds of the invention can be used to treat a JNK mediated disorder such as rheumatoid arthritis, asthma, type II diabetes, Alzheimer's disease, Parkinson's disease or stroke.

In one aspect, the application provides a method of treating a JNK-mediated disorder in a subject having a JNK-mediated disorder, said method comprising administering to a subject in need thereof a therapeutically effective amount of any of the above compounds.

In certain embodiments of the method of treating a JNK-mediated disorder, the JNK-mediated disorder is characterized by cellular proliferation.

In certain embodiments of the method of treating a JNK-mediated disorder, the JNK-mediated disorder is arthritis.

In certain embodiments of the method of treating a JNK-mediated disorder, the arthritis is rheumatoid arthritis.

In certain embodiments of the method of treating a JNK-mediated disorder, the JNK-mediated disorder is asthma.

In certain embodiments of the method of treating a JNK-mediated disorder, the JNK-mediated disorder is diabetes.

In certain embodiments of the method of treating a JNK-mediated disorder, the JNK-mediated disorder is Alzheimer's disease.

In certain embodiments of the method of treating a JNK-mediated disorder, the JNK-mediated disorder is Parkinson's disease.

In certain embodiments of the method of treating a JNK-mediated disorder, the JNK-mediated disorder is ischemic stroke.

In certain embodiments of the method of treating a JNK-mediated disorder, the JNK-mediated disorder is cancer.

In certain embodiments of the method for treating a JNK-mediated disorder, wherein the JNK-mediated disorder is cancer, the cancer is brain cancer.

In certain embodiments of the method for treating a JNK-mediated disorder, wherein the JNK-mediated disorder is cancer, the cancer is leukemia.

In certain embodiments of the method of treating a JNK-mediated disorder, the JNK-mediated disorder is kidney disease.

Combination Therapy (not Just for Inflammation)

In one aspect, the application provides a method for treating a JNK-mediated disorder comprising co-administering to a patient in need thereof a therapeutically effective amount of an anti-inflammatory compound in combination with the compound of any of the above embodiments, variations, or aspects.

EXAMPLES

The following preparations and examples are given to enable those skilled in the art to more clearly understand and to practice the present invention. They should not be considered as limiting the scope of the invention, but merely as being illustrative and representative thereof.

| Abbreviations | |
|---|---|
| Ac$_2$O | Acetic anhydride |
| AcOH | Acetic acid |
| DBU | 1,8-Diazabicyclo[5.4.0]undec-7-ene |
| DCE | 1,2-Dichloroethane |
| DCM | Dichloromethane/Methylene chloride |
| DIPEA | Diisopropylethylamine |
| DMF | N,N-dimethylformamide |
| DMSO | Dimethyl sulfoxide |
| EDCI | 1-(3-Dimethylaminopropyl)-3-ethylcarbodiimide hydrochloride |
| Et$_2$O | Diethyl ether |

| Abbreviations | |
|---|---|
| EtOH | Ethanol/Ethyl alcohol |
| EtOAc | Ethyl acetate |
| HOBt | 1-Hydroxybenzotriazole |
| LDA | Lithium diisopropylamide |
| LiHMDS | Lithium bis(trimethylsilyl)amide |
| m-CPBA | 3-Chloroperoxybenzoic acid |
| MeOH | Methanol/Methyl alcohol |
| MW | Microwaves |
| NMP | 1-Methyl-2-pyrrolidinone |
| PMB | 4-Methoxy benzyl |
| RT | Room temperature |
| TBME | tert-Butyl methyl ether |
| TFA | Trifluoroacetic acid |
| Tf$_2$O | Trifluoromethanesulfonic anhydride |
| THF | Tetrahydrofuran |
| TLC | Thin layer chromatography |

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Preparative reverse-phase high-pressure liquid chromatography (RP HPLC) was performed using one of the following systems: (A). a Waters Delta prep 4000 pump/controller, a 486 detector set at 215 nm, and a LKB Ultrorac fraction collector; or (B). a Sciex LC/MS system with a 150 EX single quad mass spec, a Shimadzu LC system, a LEAP autoinjector, and a Gilson fraction collector. The sample was dissolved in a mixture of acetonitrile/20 mM aqueous ammonium acetate or acetonitrile/water/TFA, applied on a Pursuit C-18 20×100 mm column and eluted at 20 mL/min with a linear gradient of 10%-90% B, where (A): 20 mM aqueous ammonium acetate (pH 7.0) and (B): acetonitrile or (A): water with 0.05% TFA and (B): acetonitrile with 0.05% TFA.

PREPARATIVE EXAMPLES 3-(4-Carboxy-benzyl)-7-chloro-4-oxo-1-phenyl-1,4-dihydro-quinoline-2-carboxylic acid methyl ester

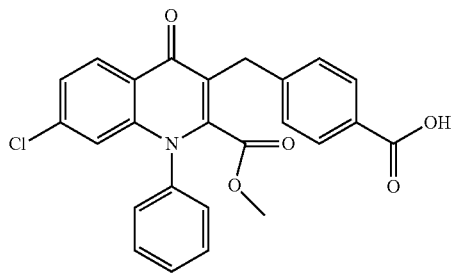 [SMILES: COC(=O)c1c(Cc2ccc(C(=O)O)cc2)c(=O)c2ccc(Cl)cc2n1-c1ccccc1]

A three-necked flask equipped with an addition funnel, a thermometer, and an overhead mechanical stirrer was charged with 2-amino-4-chlorobenzonitrile (150 g, 983 mmol) and tetrahydrofuran (3.0 L). The reaction flask was cooled to 15° C. and then was treated with methyl magnesium chloride (825 mL, 2.48 mol). Upon completion of addition of the methyl magnesium chloride, the cold bath was removed. The reaction was stirred at 25° C. overnight. At this time, the reaction mixture was cooled to 5° C. and then was treated slowly with a solution of water (500 mL) and concentrated hydrochloric acid (300 mL) while maintaining the reaction temperature under 25° C. The resulting thick suspension was stirred at 25° C. for 3 h. At this time, the mixture was cooled to 5° C. and treated with solid sodium hydroxide (300 g) in small portions. The reaction was stirred at 25° C. overnight. At this time, the organics were decanted off. The remaining thick paste was partitioned between water (2 L) and methyl tert-butyl ether (2 L). The organic layers were combined, concentrated in vacuo and then absorbed onto silica. Flash chromatography (4"×16" silica gel column; 1-3% ethyl acetate/hexanes) followed by concentration of the appropriate fractions, slurrying with hexanes, filtration and drying afforded 1-(2-amino-4-chlorophenyl)ethanone (81 g, 48.6%) as a yellow solid. This material was used without further purification.

A 3-necked round-bottomed flask equipped with a mechanic stirrer, a thermocouple probe, a reflux condenser and a nitrogen bubbler was charged with 1-(2-amino-4-chlorophenyl)ethanone (81 g, 478 mmol) in di-n-butyl ether (1 L). The reaction was then treated with pulverized potassium carbonate (200 g, 1.45 mol) and copper powder (5 g, 78 mmol). The reaction mixture was refluxed at 140-145° C. for 3 h. At this time, additional potassium carbonate (100 g, 0.72 mol), iodobenzene (100 g, 0.49 mol) and copper powder (2 g, 31 mmol) was added. The resulting mixture was refluxed overnight. At this time, the reaction was cooled to 25° C., filtered and washed with methyl tert-butyl ether. The filtrate was concentrated in vacuo. Flash chromatography (4"×16" silica gel column; 0-2% ethyl acetate/hexanes) followed by concentration of the appropriate fractions, slurrying with hexanes, filtration and drying afforded 1-(4-chloro-2-phenylamino-phenyl)-ethanone (79.3 g, 67.6%) as a yellow solid. This material was used without further purification.

A 2 L 3-necked round-bottomed flask equipped with a stirrer, a nitrogen bubbler, an addition funnel and a thermometer was charged with 1-(4-chloro-2-(phenylamino)phenyl) ethanone (79.3 g, 323 mmol) and methanol (628 g, 793 mL). The reaction was treated while stirring with a solution of sodium methoxide (25 wt % in methanol, 119 mL, 520 mmol) followed by addition of methyl 4-formylbenzoate (53.0 g, 323 mmol). The reaction mixture was allowed to stir overnight. At this time, the reaction was cooled in an ice bath. The resulting solids were collected by filtration, washed with cold methanol and dried to afford 4-[(E)-3-(4-chloro-2-phenylamino-phenyl)-3-oxo-propenyl]-benzoic acid methyl ester (115 g, 90.9%) as a red solid. This material was used without further purification.

A 500 mL round-bottomed flask equipped with a stirrer was charged with 4-[(E)-3-(4-chloro-2-phenylamino-phenyl)-3-oxo-propenyl]-benzoic acid methyl ester (5.5 g, 14.0 mmol) and ethyl acetate (100 mL). The resulting mixture was stirred under a hydrogen atmosphere for 1 h. At this time, the catalyst was removed by filtration and washed with ethyl acetate. The filtrates were concentrated in vacuo to afford 4-[3-(4-chloro-2-phenylamino-phenyl)-3-oxo-propyl]-benzoic acid methyl ester (5.5 g, 99.5%) as a gummy solid. This material was used without further purification.

A 1 L round-bottomed flask equipped with a magnetic stir bar, a water cooled reflux condenser, a nitrogen bubbler and a thermometer was charged with 4-[3-(4-chloro-2-phenylamino-phenyl)-3-oxo-propyl]-benzoic acid methyl ester (54 g, 137 mmol), toluene (2 L, 18.8 mol) and methyl 2-chloro-2-oxoacetate (200 mL, 2.17 mol). The resulting mixture was heated to reflux overnight. At this time, the reaction mixture was concentrated to a thick gum. This residue was dissolved in methanol (1 L), treated with potassium carbonate (31 g) and stirred overnight. At this time, the reaction was filtered to remove solids. The filtrate was treated with acetic acid (50 mL) and then concentrated in vacuo. The residue was absorbed onto silica gel. Flash chromatography (2"×6" column; 50-66% ethyl acetate/hexanes) followed by concentration of the appropriate fractions produced a solid. This solid was slurried with 1:1 ethyl acetate/hexanes, collected by filtration and dried in vacuo to afford 7-chloro-3-(4-methoxycarbonyl-benzyl)-4-oxo-1-phenyl-1,4-dihydro-quinoline-2-carboxylic acid methyl ester (34 g, 53.7%) as an off-white solid. This material was used without further purification.

A 2 L three necked round bottom flask equipped with a mechanical stirrer, a nitrogen bubbler and a thermometer was charged with 7-chloro-3-(4-methoxycarbonyl-benzyl)-4-oxo-1-phenyl-1,4-dihydro-quinoline-2-carboxylic acid methyl ester (34 g, 73.6 mmol) methanol (600 mL) and 1,4-dioxane (300 mL). The resulting mixture was treated with lithium hydroxide (3.52 g, 146 mmol). The reaction was stirred at 25° C. over the weekend. At this time, the reaction was warmed to 35° C. and was stirred at 35° C. overnight. The reaction was then treated with additional lithium hydroxide (3.5 g, 1.46 mmol) and water (10 mL) and continued to stir at 35° C. overnight. At this time, additional 1,4-dioxane (300 mL) was added to the reaction. The reaction was stirred at 35° C. overnight. The reaction was then warmed to 40° C. where it stirred for 8 h and then was stirred at 35° C. overnight. At this time, the reaction was cooled to 25° C., treated with concentrated hydrochloric acid (25 mL) and methyl acetate (500 mL) and concentrated in vacuo. The resulting solids were collected by filtration, washed with methanol and dried in vacuo to afford 3-(4-carboxy-benzyl)-7-chloro-4-oxo-1-phenyl-1,4-dihydro-quinoline-2-carboxylic acid methyl ester (27.5 g). An additional amount of 3-(4-carboxy-benzyl)-7-chloro-4-oxo-1-phenyl-1,4-dihydro-quinoline-2-carboxylic acid methyl ester (3 g, total yield: 92.5%) was obtained through concentration of the filtrate and collection of the resulting solids. This material was used without further purification.

3-(4-Carboxy-benzyl)-4-oxo-1-phenyl-1,4-dihydro-[1,8]naphthyridine-2-carboxylic acid methyl ester

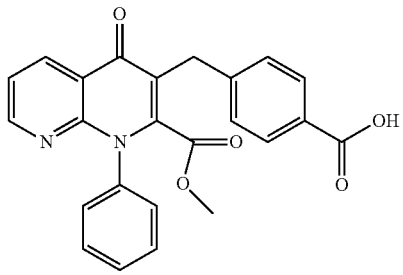 [SMILES: COC(=O)c1c(Cc2ccc(C(=O)O)cc2)c(=O)c2cccnc2n1-c1ccccc1]

A solution of 2-chloronicotinic acid (20.0 g, 127 mmol) in N,N-dimethylformamide (600 mL, 0.21M) was treated with N,N-diisopropylethylamine (66 mL, 379 mmol), N,O-dimethylhydroxylamine hydrochloride (13.63 g, 140 mmol), and benzotriazole-1-yl-oxy-tris-(dimethylamino)-phosphonium hexafluorophosphate (84.25 g, 190 mmol). The reaction was stirred at 25° C. over 3 d. The resulting reaction was concentrated in vacuo, taken up in ethyl acetate (400 mL) and washed with a saturated aqueous ammonium chloride solution (2×250 mL), a saturated aqueous sodium bicarbonate solution (2×250 mL), and a saturated aqueous sodium chloride solution (250 mL). The organics were dried over magnesium sulfate, filtered and rinsed with ethyl acetate, and concentrated in vacuo. Flash chromatography (AnaLogix IntelliFlash 280 column chromatography, 400 g silica gel column, 25-50% ethyl acetate/hexanes) afforded 2-chloro-N-methoxy-N-methyl-nicotinamide (23.58 g, 93%) as a light yellow oil.

A solution of 2-chloro-N-methoxy-N-methyl-nicotinamide (23.6 g, 118 mmol) in tetrahydrofuran (350 mL, 0.34M) at 0° C. was treated dropwise via an addition funnel with methyl magnesium chloride (3.0M solution in tetrahydrofuran, 100 mL, 300 mmol). The reaction became a very thick opaque white mixture and was diluted with additional tetrahydrofuran (150 mL). The reaction was stirred at 0° C. for 1 h. At this time, the reaction was carefully quenched with water (250 mL) and then partitioned between additional water (250 mL) and ethyl acetate (250 mL). The aqueous layer was back extracted with ethyl acetate (2×250 mL). The combined organics were washed with a saturated aqueous sodium chloride solution (250 mL), dried over magnesium sulfate, filtered, rinsed with ethyl acetate, and concentrated in vacuo. Flash chromatography (AnaLogix Intelliflash 280, 400 g silica gel column, 25-50% ethyl acetate/hexanes) afforded 1-(2-chloro-pyridin-3-yl)-ethanone (13.17 g, 72%) as a yellow oil.

A solution of 1-(2-chloro-pyridin-3-yl)-ethanone (6.42 g, 41.3 mmol) and 1,4-dioxane (70 mL, 0.59M) in a large sealed tube vessel was treated with DL-10-camphorsulfonic acid (23.96 g, 103 mmol). The vessel was tightly sealed, placed behind a blast shield, and warmed to 75° C. At this time, the reaction vessel was removed from the oil bath, carefully opened, treated quickly with aniline (5.6 mL, 61.5 mmol), resealed, and lowered back into the oil bath. The reaction was then warmed to 80° C., where it was stirred for 3 h. At this time, the reaction was cooled to 25° C., diluted with ethyl acetate (250 mL) and washed with a saturated aqueous sodium bicarbonate solution (3×250 mL), water (150 mL) and a saturated aqueous sodium chloride solution (150 mL). The organics were dried over magnesium sulfate, filtered, rinsed with ethyl acetate, and concentrated in vacuo. Flash chromatography (AnaLogix Intelliflash 280, 220 g silica gel column, 1-20% ethyl acetate/hexanes) afforded 1-(2-phenylamino-pyridin-3-yl)-ethanone (3.14 g, 36%) as a yellow solid.

A solution of 1-(2-phenylamino-pyridin-3-yl)-ethanone (2.13 g, 10.0 mmol) in methanol (42 mL, 0.24M) was treated with sodium methoxide (25% wt. solution methanol, 4.6 mL, 20.1 mmol) and methyl 4-formylbenzoate (2.04 g, 12.4 mmol). The reaction was stirred at 25° C. over 3 d. At this time, the reaction was diluted with water (100 mL), acidified with a 1N aqueous hydrochloric acid solution, and extracted with a 10% methanol/methylene chloride solution. The combined organics were dried over magnesium sulfate, filtered, rinsed with methylene chloride, and concentrated onto silica gel in vacuo. Flash chromatography (AnaLogix Intelliflash 280, 80 g silica gel column, 20% ethyl acetate/hexanes) afforded 4-[(E)-3-oxo-3-(2-phenylamino-pyridin-3-yl)-propenyl]-benzoic acid methyl ester (3.43 g, 95%) as an orange solid.

A mixture of 4-[(E)-3-oxo-3-(2-phenylamino-pyridin-3-yl)-propenyl]-benzoic acid methyl ester (2.45 g, 6.84 mmol) and ethyl acetate (280 mL, 0.024M) was treated with 10% palladium on carbon (0.24 g, 10% weight of starting material used). The flask was fitted with a hydrogen balloon, and the reaction stirred at 25° C. overnight. At this time, the reaction was filtered through a pad of Celite®, rinsed with ethyl acetate, and concentrated in vacuo. Flash chromatography (AnaLogix Intelliflash 280, 80 g silica gel column, 1-20% ethyl acetate/hexanes) afforded 4-[3-oxo-3-(2-phenylamino-pyridin-3-yl)-propyl]-benzoic acid methyl ester (2.00 g, 81%) as an orange solid.

A solution of 4-[3-oxo-3-(2-phenylamino-pyridin-3-yl)-propyl]-benzoic acid methyl ester (2.00 g, 5.55 mmol) in toluene (100 mL, 0.055M) was treated with methyl oxalyl chloride (5.0 mL, 54.2 mmol). The reaction was warmed to 130° C. where it stirred for 6 h. At this time, the reaction was concentrated in vacuo to afford 4-{3-[2-(methoxyoxalyl-phenyl-amino)-pyridin-3-yl]-3-oxo-propyl}-benzoic acid methyl ester. This material was used without further purification.

A solution of 4-{3-[2-(methoxyoxalyl-phenyl-amino)-pyridin-3-yl]-3-oxo-propyl}-benzoic acid methyl ester (assume 5.55 mmol) in methanol (55 mL, 0.10 M) was treated with potassium carbonate (7.69 g, 55.6 mmol). The reaction was warmed to 85° C. where it stirred for 4 h. At this time, the reaction was cooled to 25° C. and then concentrated in vacuo. The residue was then taken up in water (200 mL) and extracted with diethyl ether (100 mL). The aqueous layer was acidified to pH 2-3 with a 1N aqueous hydrochloric acid solution. The resulting precipitate was filtered, rinsed with water, and dried in vacuo to afford 3-(4-carboxy-benzyl)-4-oxo-1-phenyl-1,4-dihydro-[1,8]naphthyridine-2-carboxylic acid methyl ester (1.89 g, 82% over 2 steps) as a light brown solid.

Example 1 rel-3-[4-((1S,2S,3R,5S,7S)-5-Hydroxy-adamantan-2-ylcarbamoyl)-benzyl]-4-oxo-1-phenyl-1,4-dihydro-[1,8]naphthyridine-2-carboxylic acid methyl ester

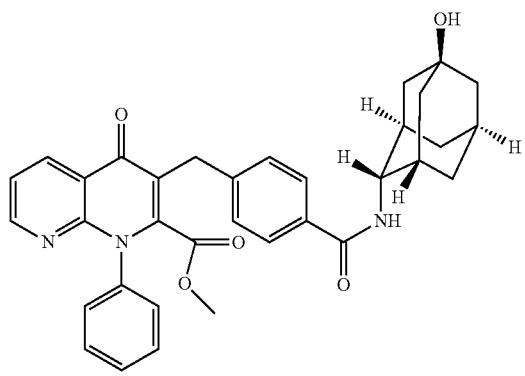 [SMILES: COC(=O)c1c(Cc2ccc(C(=O)N[C@@H]3[C@@H]4C[C@@H]5C[C@H]3C[C@@](O)(C5)C4)cc2)c(=O)c2cccnc2n1-c1ccccc1]

A solution of 3-(4-carboxy-benzyl)-4-oxo-1-phenyl-1,4-dihydro-[1,8]naphthyridine-2-carboxylic acid methyl ester (6.44 g, 15.5 mmol) in methylene chloride (150 mL, 0.1M) was treated with N,N-diisopropylethylamine (20.0 g, 27 mL, 153 mmol), (1S,3R,4S,5S,7S)-4-amino-adamantan-1-ol hydrochloride (see WO2007/107470 A2, 3.33 g, 16.3 mmol), 1-[3-dimethylaminopropyl]-3-ethylcarbodiimide hydrochloride (4.91 g, 25.4 mmol), and 1-hydroxybenzotriazole (3.41 g, 24.7 mmol). The reaction was stirred at 25° C. for 2 d. At this time, the reaction was diluted with methylene chloride (200 mL) and was washed with a 1N aqueous hydrochloric acid solution (2×200 mL), a saturated aqueous sodium bicarbonate solution (2×200 mL), and water (200 mL). The organics were dried over magnesium sulfate, filtered and rinsed with methylene chloride and concentrated in vacuo. The residue was diluted with a small amount of methylene chloride and absorbed onto silica gel. Flash chromatography (AnaLogix IntelliFlash 280, 220 g silica gel column, 100% ethyl acetate followed by 1-5% methanol/methylene chloride). Pure product fractions were combined, concentrated in vacuo and then redissolved in methanol and concentrated in vacuo (four times) and dried under high vacuum to afford 3-[4-((1S,2S,3R,5S,7S)-5-hydroxy-adamantan-2-ylcarbamoyl)-benzyl]-4-oxo-1-phenyl-1,4-dihydro-[1,8]naphthyridine-2-carboxylic acid methyl ester methanol solvate as a fine, light yellow powder (6.59 g, 75%). ES$^+$-HRMS m/e calcd for $C_{34}H_{33}N_3O_5$ [M+H$^+$] 564.2493. Found 564.2493; $^1$H NMR (300 MHz, DMSO-d$_6$) δ ppm 1.32 (d, J=11.49 Hz, 2H) 1.50-1.80 (m, 6H) 1.85-2.17 (m, 5H) 3.45 (s, 3H) 3.77-3.96 (m, 3H) 4.41 (s, 1H) 7.33 (d, J=8.29 Hz, 2H) 7.38-7.59 (m, 6H) 7.69 (d, J=8.29 Hz, 2H) 7.78 (d, J=6.78 Hz, 1H) 8.58 (dd, J=7.91, 1.88 Hz, 1H) 8.68 (dd, J=4.52, 1.88 Hz, 1H).

Example 2 rel-3-[4-((1S,2R,3R,5S,7S)-5-Hydroxy-adamantan-2-ylcarbamoyl)-benzyl]-4-oxo-1-phenyl-1,4-dihydro-[1,8]naphthyridine-2-carboxylic acid methyl ester

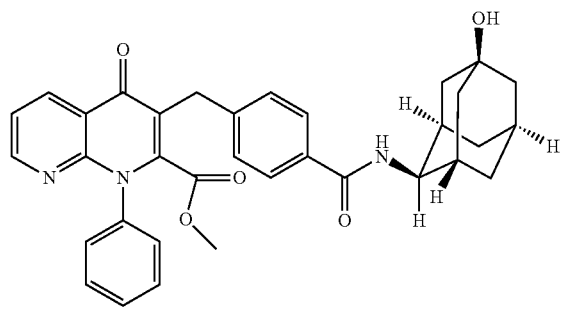

A solution of 3-(4-carboxy-benzyl)-4-oxo-1-phenyl-1,4-dihydro-[1,8]naphthyridine-2-carboxylic acid methyl ester (0.18 g, 0.43 mmol) in N,N-dimethylformamide (2.2 mL, 0.2M) was treated with N,N-diisopropylethylamine (225 µL, 1.29 mmol), 4-amino-adamantan-1-ol hydrochloride (mixture of cis and trans isomers) (83.5 g, 0.45 mmol) and benzotriazole-1-yl-oxy-tris-(dimethylamino)-phosphonium hexafluorophosphate (0.29 g, 0.65 mmol). The reaction was stirred at 25° C. overnight. At this time, the reaction was washed with a saturated aqueous ammonium chloride solution and a saturated aqueous sodium bicarbonate solution. The organics were dried over sodium sulfate, filtered and concentrated in vacuo. Flash chromatography (40 g silica gel column, 0.5-4% methanol/methylene chloride) gave two sets of product fractions. Each set of fractions were combined, concentrated in vacuo and then redissolved in ethanol, concentrated and dried under high vacuum. The product fraction containing a higher rf material afforded 3-[4-((1S,3R,5S,7S)-5-hydroxy-adamantan-2-ylcarbamoyl)-benzyl]-4-oxo-1-phenyl-1,4-dihydro-[1,8]naphthyridine-2-carboxylic acid methyl ester (78.6 mg, 32.1%) as light yellow solid. ES$^+$-HRMS m/e calcd for $C_{34}H_{33}N_3O_5$ [M+H$^+$] 564.2493. Found 564.2493; $^1$H NMR (300 MHz, DMSO-d$_6$) ppm 1.35 (d, J=11.77 Hz, 2H) 1.48-1.73 (m, 6H) 1.81-2.22 (m, 5H) 3.36-3.51 (m, 3H) 3.73-3.87 (m, 3H) 4.32 (s, 1H) 7.32 (d, J=8.45 Hz, 2H) 7.39-7.57 (m, 6H) 7.68 (d, J=8.15 Hz, 2H) 7.71-7.82 (m, 1H) 8.56 (dd, J=8.00, 1.96 Hz, 1H) 8.67 (dd, J=4.53, 1.81 Hz, 1H). The product fraction containing the lower rf material afforded 3-[4-((1S,2S,3R,5S,7S)-5-hydroxy-adamantan-2-ylcarbamoyl)-benzyl]-4-oxo-1-phenyl-1,4-dihydro-[1,8]naphthyridine-2-carboxylic acid methyl ester (128.7 mg, 53%) as an off white solid.

Example 3 rel-7-Chloro-3-[4-((1S,2S,3R,5S,7S)-5-hydroxy-adamantan-2-ylcarbamoyl)-benzyl]-4-oxo-1-phenyl-1,4-dihydro-quinoline-2-carboxylic acid methyl ester

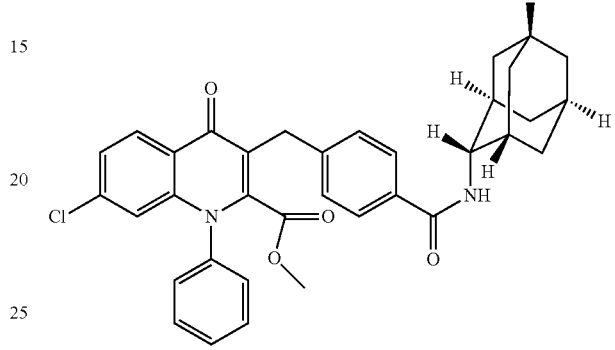

A solution of 3-(4-carboxy-benzyl)-7-chloro-4-oxo-1-phenyl-1,4-dihydro-quinoline-2-carboxylic acid methyl ester (100 mg, 223 µmol) in methylene chloride (10 mL) was treated with N,N-diisopropylethylamine (291 mg, 2.25 mmol), (1S,3R,5S,7S)-4-amino-adamantan-1-ol hydrochloride (see WO2007/107470 A2, 71.8 mg, 335 µmol), 1-[3-dimethylaminopropyl]-3-ethylcarbodiimide hydrochloride (69.2 mg, 357 µmol), and 1-hydroxybenzotriazole (55.8 mg, 357 µmol). The reaction was stirred at 25° C. for 18 h. At this time, the reaction was diluted with methylene chloride and was washed with a 1N aqueous hydrochloric acid solution, a 1M aqueous potassium carbonate solution, water and a saturated aqueous sodium chloride solution. The organics were dried over magnesium sulfate, filtered and concentrated in vacuo. The residue was diluted with a small amount of methylene chloride and absorbed onto silica gel. Flash chromatography (Varian Intelliflash 310, 12 g silica gel column, 0-6% methanol/methylene chloride) afforded 7-chloro-3-[4-((1S,2S,3R,5S,7S)-5-hydroxy-adamantan-2-ylcarbamoyl)-benzyl]-4-oxo-1-phenyl-1,4-dihydro-quinoline-2-carboxylic acid methyl ester (33.3 mg, 25%) as a white solid. ES$^+$-HRMS m/e calcd for $C_{35}H_{33}ClN_2O_5$ [M+H$^+$] 597.2151. found 597.2151; $^1$H NMR (DMSO-d$_6$) δ ppm 8.22 (d, J=8.8 Hz, 1H), 7.73-7.81 (m, 1H), 7.63-7.70 (m, 5H), 7.53-7.60 (m, 2H), 7.47 (dd, J=8.8, 1.8 Hz, 1H), 7.31 (d, J=8.2 Hz, 2H), 6.71 (d, J=1.8 Hz, 1H), 4.41 (s, 1H), 3.85-3.96 (m, 1H), 3.81 (s, 2H), 3.43 (s, 3H), 1.89-2.11 (m, 5H), 1.55-1.75 (m, 6H), 1.31 (d, J=11.8 Hz, 2H).

Example 4 rel-7-Chloro-3-[4-((1S,2R,3R,5S,7S)-5-hydroxy-adamantan-2-ylcarbamoyl)-benzyl]-4-oxo-1-phenyl-1,4-dihydro-quinoline-2-carboxylic acid methyl ester

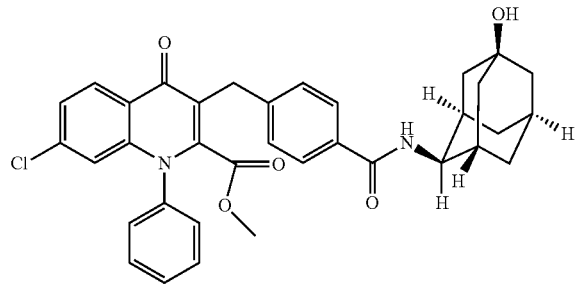 [SMILES: COC(=O)c1c(Cc2ccc(C(=O)N[C@H]3[C@@H]4C[C@@H]5C[C@H]3C[C@@](O)(C5)C4)cc2)c(=O)c2ccc(Cl)cc2n1-c1ccccc1]

A solution of 3-(4-carboxy-benzyl)-7-chloro-4-oxo-1-phenyl-1,4-dihydro-quinoline-2-carboxylic acid methyl ester (100 mg, 223 µmol) in methylene chloride (10 mL) was treated with N,N-diisopropylethylamine (291 mg, 2.25 mmol), (1S,3R,5S,7S)-4-amino-adamantan-1-ol hydrochloride (see WO2007/107470 A2, 71.8 mg, 335 µmol), 1-[3-dimethylaminopropyl]-3-ethylcarbodiimide hydrochloride (69.2 mg, 357 µmol), and 1-hydroxybenzotriazole (55.8 mg, 357 µmol). The reaction was stirred at 25° C. for 18 h. At this time, the reaction was diluted with methylene chloride and was washed with a 1N aqueous hydrochloric acid solution, a 1M aqueous potassium carbonate solution, water and a saturated aqueous sodium chloride solution. The organics were dried over magnesium sulfate, filtered and concentrated in vacuo. The residue was diluted with a small amount of methylene chloride and absorbed onto silica gel. Flash chromatography (Varian Intelliflash 310, 12 g silica gel column, 0-6% methanol/methylene chloride) afforded 7-chloro-3-[4-((1S,3R,5S,7S)-5-hydroxy-adamantan-2-ylcarbamoyl)-benzyl]-4-oxo-1-phenyl-1,4-dihydro-quinoline-2-carboxylic acid methyl ester (50.3 mg, 37.7%) as a white solid. ES$^+$-HRMS m/e calcd for $C_{35}H_{33}ClN_2O_5$ [M+H$^+$] 597.2151 found 597.2149; $^1$H NMR (DMSO-d$_6$) δ ppm 8.23 (d, J=8.7 Hz, 1H), 7.79 (d, J=5.7 Hz, 1H), 7.62-7.73 (m, 5H), 7.53-7.61 (m, 2H), 7.47 (dd, J=8.7, 1.9 Hz, 1H), 7.32 (d, J=8.5 Hz, 2H), 6.71 (d, J=1.9 Hz, 1H), 4.33 (s, 1H), 3.82 (s, 2H), 3.74-3.85 (m, 1H), 3.44 (s, 3H), 2.16 (br. s., 2H), 2.01 (br. s., 1H), 1.94 (d, J=12.1 Hz, 2H), 1.50-1.71 (m, 6H), 1.37 (d, J=11.8 Hz, 2H).

Example 5 rel-4-(7-Chloro-4-oxo-1-pyridin-2-yl-1,4-dihydro-quinolin-3-ylmethyl)-N-((1S,2S,3R,5S,7S)-5-hydroxy-adamantan-2-yl)-benzamide

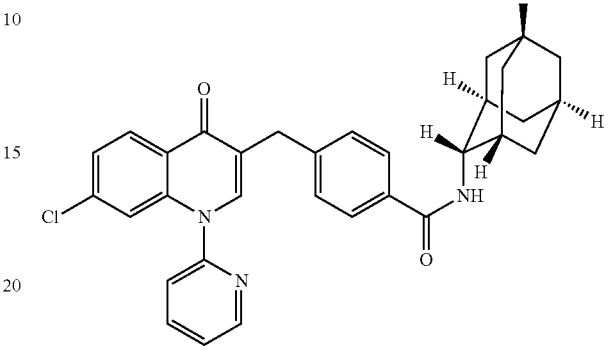

A 2 liter three neck flask equipped with an addition funnel, an argon inlet, and an overhead mechanical stirrer was charged with 2-amino-4-chlorobenzonitrile (15 g, 0.098 mol) and anhydrous diethyl ether (1.2 L). The reaction flask was back-filled with argon gas. The mixture was then cooled to 0° C. in an ice water bath. At this time, the reaction was treated with a solution of methyl magnesium chloride (3.0 M in tetrahydrofuran, 100 mL, 0.30 mol). The addition process occurred over 90 min. At this time, the reaction mixture was stirred at 0° C. for an additional 90 min. The reaction was then warmed to 25° C. and was stirred at 25° C. for 20 min. At this time, the reaction mixture was cooled to −60° C. using a dry ice/acetone bath and was then treated slowly dropwise with a 6N aqueous hydrochloric acid solution (100 mL). The reaction mixture was then allowed to warm to 18° C. with stirring over the course of 3 h. At this time, the reaction was treated with an additional amount of the 6N aqueous hydrochloric acid solution (100 mL). At this time, the reaction mixture was transferred to a separatory funnel. The organic layer was separated and set aside. The aqueous layer was brought to pH 9 by the slow addition of solid potassium hydroxide with stirring. The resulting mixture was then extracted with ethyl acetate. The combined organic layers were dried over magnesium sulfate, filtered and concentrated in vacuo to afford 1-(2-amino-4-chlorophenyl)ethanone (16.1 g, 96%) as a tan solid. This material was used without further purification.

A solution of 1-(2-amino-4-chlorophenyl)ethanone (1000 mg, 5.9 mmol) in dioxane (14.7 mL) at 25° C. in a thick walled high pressure reaction flask was treated with sodium phenoxide (958 mg, 8.25 mmol), 4,5-bis(diphenylphosphino)-9,9-dimethylxanthene (108 mg, 118 µmol), tris(dibenzylideneacetone)dipalladium(0) (75.1 mg, 130 µmol) and 2-chloropyridine (669 mg, 5.9 mmol). The reaction flask was tightly capped and then heated to 100° C. for 2 d. At this time, the reaction was cooled to 25° C., diluted with a 10% solution of methanol/methylene chloride (50 mL) and filtered through a pad of Celite® rinsing with a 10% solution of methanol/methylene chloride (2×30 mL). The filtrate was concentrated in vacuo. The crude material was purified using reverse phase chromatography (ammonium acetate/acetonitrile with trifluoroacetic acid) to afford the trifluoroacetic acid salt of 1-[4-chloro-2-(pyridin-2-ylamino)-phenyl]-ethanone (544 mg, 25.6%) as an off-white solid. ES$^+$-HRMS m/e calcd for $C_{13}H_{11}ClN_2O$ [M+H$^+$] 247.0633. Found 247.0628; $^1$H NMR (400 MHz, DMSO-d$_6$) δ ppm 12.26 (br. s., 1H) 8.87 (s, 1H) 8.71 (d, J=6.4 Hz, 1H) 8.14 (t, J=7.8 Hz, 1H) 7.65 (d, J=8.5 Hz, 1H) 7.28-7.45 (m, 3H) 7.19 (br. s., 1H) 1.82 (br. s., 3H).

A mixture of the trifluoroacetic acid salt of 1-[4-chloro-2-(pyridin-2-ylamino)-phenyl]-ethanone (273 mg, 757 μmol) in methanol (3.78 mL) at 25° C. was treated with methyl 4-formylbenzoate (124 mg, 757 μmol) and sodium methoxide in methanol (4.37M, 520 μL, 2.27 mmol). The reaction was stirred at 25° C. for 3 d. At this time, the reaction was diluted with water (50 mL), neutralized with a 1N aqueous hydrochloric acid solution and extracted with methylene chloride (3×50 mL). The combined organics were dried over sodium sulfate, filtered and concentrated in vacuo to afford 4-{(E)-3-[4-chloro-2-(pyridin-2-ylamino)-phenyl]-3-oxo-propenyl}-benzoic acid methyl ester (287.3 mg, 96.6%) as an orange solid. The material was used without further purification.

A mixture of 4-{(E)-3-[4-chloro-2-(pyridin-2-ylamino)-phenyl]-3-oxo-propenyl}-benzoic acid methyl ester (287 mg, 731 μmol) in methanol (12.2 mL) at 25° C. was treated with platinum (IV) oxide (8.3 mg, 36.5 μmol). The reaction was stirred under a balloon of hydrogen gas at 25° C. for 18 h. At this time, the reaction was filtered through a pad of Celite® to remove the catalyst. The Celite® was rinsed with a 10% solution of methanol/methylene chloride (2×30 mL). The filtrate was concentrated in vacuo to afford 4-{3-[4-chloro-2-(pyridin-2-ylamino)-phenyl]-3-oxo-propyl}-benzoic acid methyl ester (291 mg, quant.) as a dark green solid. The material was used without further purification.

A solution of N,N-dimethylformamide (268 mg, 286 μL, 3.67 mmol) and tetrahydrofuran (2.94 mL) cooled to 0° C. was treated with oxalyl chloride (373 mg, 256 μL, 2.94 mmol). During the addition process, vigorous gas evolution occurred, the reaction became cloudy and a thick white precipitate formed. At this time, the ice bath was removed. The reaction mixture was stirred at 25° C. for 45 min and then was concentrated in vacuo. The resulting white paste was treated with toluene (11.8 mL) and 4-{3-[4-chloro-2-(pyridin-2-ylamino)-phenyl]-3-oxo-propyl}-benzoic acid methyl ester (290 mg, 734 μmol). This mixture was then heated to 115° C. for 5 h and then was stirred at 25° C. overnight. At this time, the reaction was diluted with water (30 mL) and extracted into methylene chloride (3×30 mL). The organics were dried over sodium sulfate, filtered and concentrated in vacuo. Flash chromatography (40 g column; 1-10% methanol/methylene chloride) afforded 4-(7-chloro-4-oxo-1-pyridin-2-yl-1,4-dihydro-quinolin-3-ylmethyl)-benzoic acid methyl ester (28.7 mg, 9.65%) as a brown solid. ES$^+$-HRMS m/e calcd for $C_{23}H_{17}ClN_2O_3$ [M+H$^+$] 405.1000. Found 405.0995; $^1$H NMR (300 MHz, DMSO-d$_6$) δ ppm 8.73 (d, J=4.7 Hz, 1H) 8.29 (s, 1H) 8.14-8.24 (m, 2H) 7.85 (d, J=8.2 Hz, 2H) 7.79 (d, J=7.9 Hz, 1H) 7.63-7.72 (m, 1H) 7.47 (d, J=8.2 Hz, 2H) 7.43 (m, 1H) 7.21 (d, J=1.7 Hz, 1H) 3.89 (s, 2H) 3.82 (s, 3H).

A solution of 4-(7-chloro-4-oxo-1-pyridin-2-yl-1,4-dihydro-quinolin-3-ylmethyl)-benzoic acid methyl ester (28 mg, 69.2 μmol) in tetrahydrofuran (553 μL) at 25° C. was treated with a solution of lithium hydroxide monohydrate (5.8 mg, 138 μmol) in water (138 μL). The reaction was stirred at 25° C. for 24 h. At this time, LCMS indicated that the reaction was incomplete. The reaction was treated with additional lithium hydroxide monohydrate (5.8 mg, 138 μmol). The reaction was stirred overnight at 25° C. At this time, LCMS still indicated that the reaction was incomplete. The reaction was treated with a third portion of lithium hydroxide monohydrate (5.8 mg, 138 μmol). The reaction was stirred overnight at 25° C. At this time, the reaction was diluted with water (30 mL) and extracted with methylene chloride (1×30 mL). The aqueous layer was then acidified with a 1N aqueous hydrochloric acid solution and extracted with a 10% solution of methanol/methylene chloride (3×50 mL). These organics were dried over sodium sulfate, filtered and concentrated in vacuo to afford 4-(7-chloro-4-oxo-1-pyridin-2-yl-1,4-dihydro-quinolin-3-ylmethyl)-benzoic acid (18 mg, 66.6%) as a light brown solid. ES$^+$-HRMS m/e calcd for $C_{22}H_{15}ClN_2O_3$ [M+H$^+$] 391.0844. Found 391.0835; $^1$H NMR (400 MHz, DMSO-d$_6$) δ ppm 12.79 (br. s., 1H) 8.73 (dd, J=4.8, 1.2 Hz, 1H) 8.29 (s, 1H) 8.17-8.25 (m, 1H) 7.77-7.86 (m, 3H) 7.68 (dd, J=7.1, 5.2 Hz, 1H) 7.41-7.48 (m, 3H) 7.22 (d, J=1.8 Hz, 1H) 3.88 (s, 1H).

A solution of 4-(7-chloro-4-oxo-1-pyridin-2-yl-1,4-dihydro-quinolin-3-ylmethyl)-benzoic acid (16 mg, 40.9 μmol), (1S,3R,4S,5S,7S)-4-amino-adamantan-1-ol hydrochloride (see WO2007/107470 A2, 6.85 mg, 40.9 μmol), 1-[3-dimethylamino]propyl]-3-ethylcarbodiimide hydrochloride (12.7 mg, 65.5 μmol) and 1-hydroxybenzotriazole (9.03 mg, 65.5 μmol) in methylene chloride (1.64 mL) was treated with N,N-diisopropylethylamine (53.4 mg, 72.2 μL, 409 μmol). The reaction was stirred at 25° C. for 2 d. At this time, the reaction was diluted with methylene chloride (50 mL) and was washed with a saturated aqueous ammonium chloride solution (1×100 mL) and a saturated aqueous sodium bicarbonate solution (1×100 mL). The organics were dried over sodium sulfate, filtered and concentrated in vacuo. Flash chromatography (1.5-5% methanol/methylene chloride) afforded 4-(7-chloro-4-oxo-1-pyridin-2-yl-1,4-dihydro-quinolin-3-ylmethyl)-N-((1S,2S,3R,5S,7S)-5-hydroxy-adamantan-2-yl)-benzamide (7.8 mg, 35.3%) as a light brown solid. ES$^+$-HRMS m/e calcd for $C_{32}H_{30}ClN_3O_3$ [M+H$^+$] 540.2048. Found 540.2038; $^1$H NMR (400 MHz, DMSO-d$_6$) δ ppm 8.74 (dd, J=4.8, 1.4 Hz, 1H) 8.26 (s, 1H) 8.23 (d, J=8.7 Hz, 1H) 8.21 (td, J=7.8, 1.8 Hz, 1H) 7.76-7.84 (m, 2H) 7.65-7.72 (m, 3H) 7.45 (dd, J=8.7, 1.8 Hz, 1H) 7.41 (d, J=8.1 Hz, 2H) 7.21 (d, J=1.8 Hz, 1H) 4.43 (s, 1H) 3.90 (br. s., 1H) 3.87 (s, 2H) 1.91-2.13 (m, 5H) 1.56-1.76 (m, 6H) 1.32 (d, J=12.3 Hz, 2H).

Example 6 rel-3-[4-((1S,2S,3R,5S,7S)-5-Acetoxy-adamantan-2-ylcarbamoyl)-benzyl]-7-chloro-4-oxo-1-phenyl-1,4-dihydro-quinoline-2-carboxylic acid methyl ester

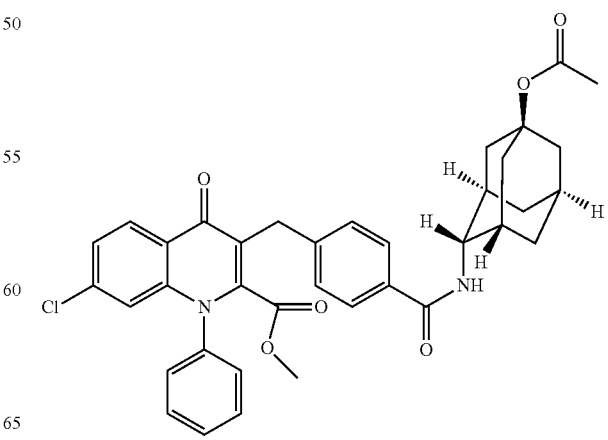

A mixture of 7-chloro-3-[4-(5-hydroxy-adamantan-2-yl-carbamoyl)-benzyl]-4-oxo-1-phenyl-1,4-dihydro-quinoline-2-carboxylic acid methyl ester (74.9 mg, 125 μmol) and chloroacetonitrile (102 mg, 85 μL, 1.32 mmol) was treated with glacial acetic acid (105 mg, 100 μL, 1.74 mmol). The resulting slurry was cooled to 0° C. and then treated with concentrated sulfuric acid (184 mg, 100 μL, 1.79 mmol). The reaction mixture was stirred at 0° C. for 30 min. At this time, the reaction was allowed to slowly warm to 25° C. where it stirred for 3.5 h. At this time, the reaction was stored in the freezer overnight. At this time, the reaction was allowed to warm to 25° C. and was stirred at 25° C. for 1 d. At this time, the reaction was diluted with ice-water (3 mL) and then further diluted with more water (9 mL). The resulting mixture was stirred at 25° C. for 30 min. At this time, the resulting precipitate was collected by filtration, washed with water and dried under house vacuum overnight. Reverse phase liquid chromatography (Pursuit C-18 column; ammonium acetate/acetonitrile modifier) afforded 3-[4-((1S,2S,3R,5S,7S)-5-acetoxy-adamantan-2-ylcarbamoyl)-benzyl]-7-chloro-4-oxo-1-phenyl-1,4-dihydro-quinoline-2-carboxylic acid methyl ester (10 mg, 12.5%) as a white solid. LC/MS-ES(+/−) calcd for $C_{37}H_{35}ClN_2O_6$ [M+] 638. Found 638. $^1$H NMR (400 MHz, DMSO-$d_6$) δ ppm 1.23 (s, 2H) 1.41 (d, J=12.09 Hz, 2H) 1.93 (s, 3H) 1.96-2.23 (m, 10H) 3.44 (s, 3H) 3.82 (s, 2H) 3.97 (d, J=6.04 Hz, 1H) 6.71 (d, J=2.01 Hz, 1H) 7.32 (d, J=8.26 Hz, 2H) 7.47 (dd, J=8.66, 1.81 Hz, 1H) 7.53-7.59 (m, 2H) 7.63-7.72 (m, 5H) 7.86 (d, J=6.45 Hz, 1H) 8.22 (d, J=8.66 Hz, 1H).

Example 7 rel-3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester

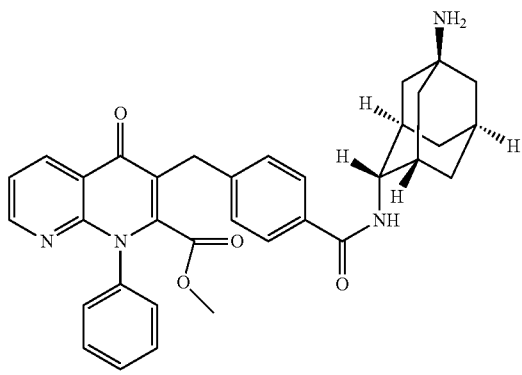 [SMILES: COC(=O)c1c(Cc2ccc(C(=O)N[C@@H]3[C@@H]4C[C@@H]5C[C@H]3C[C@@](N)(C5)C4)cc2)c(=O)c2cccnc2n1-c1ccccc1]

A mixture of 3-[4-((1S,2S,3R,5S,7S)-5-hydroxy-adamantan-2-ylcarbamoyl)-benzyl]-4-oxo-1-phenyl-1,4-dihydro-[1,8]naphthyridine-2-carboxylic acid methyl ester (80.4 mg, 143 mol) and chloroacetonitrile (64.6 mg, 54 μL, 856 μmol) in glacial acetic acid (67.9 μL) cooled to 0° C. was treated with sulfuric acid (126 mg, 68.4 μL, 1.28 mmol). The reaction was stirred at 0° C. for 1 h. It was then allowed to gradually warm to 25° C. where it stirred overnight. At this time, additional sulfuric acid (0.12 mL) and acetic acid (0.12 mL) was added to facilitate stirring and dissolution. The reaction continued to stir for an additional 24 h. At this time, the reaction was diluted with water and then was neutralized with a saturated aqueous sodium bicarbonate solution. This solution was extracted into methylene chloride (3×30 mL), dried over sodium sulfate, filtered and concentrated in vacuo to afford 3-{4-[(1S,2S,3R,5S,7S)-5-(2-chloro-acetylamino)-adamantan-2-ylcarbamoyl]-benzyl}-4-oxo-1-phenyl-1,4-dihydro-[1,8]naphthyridine-2-carboxylic acid methyl ester (112.1 mg) as a light yellow solid. The material was used without further purification.

A solution of 3-{4-[(1S,2S,3R,5S,7S)-5-(2-chloro-acetylamino)-adamantan-2-ylcarbamoyl]-benzyl}-4-oxo-1-phenyl-1,4-dihydro-[1,8]naphthyridine-2-carboxylic acid methyl ester (91.4 mg, 143 μmol) and thiourea (15.2 mg, 200 μmol) in ethanol (1.19 mL) cooled to 0° C. was treated with glacial acetic acid (238 μL). The reaction was heated to reflux where it stirred overnight. At this time, the reaction was cooled to 25° C., diluted with water (5 mL) and neutralized by the dropwise addition of a saturated aqueous sodium bicarbonate solution. This solution was then extracted with methylene chloride (3×30 mL). The organics were dried over sodium sulfate, filtered and concentrated in vacuo. Flash chromatography (4 g, 2-10% methanol/methylene chloride) afforded 3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester (26.6 mg, 33.1%) as an off-white solid. ES$^+$-HRMS m/e calcd for $C_{34}H_{34}N_4O_4$ [M+H$^+$] 563.2653. Found 563.3642; $^1$H NMR (500 MHz, DMSO-$d_6$) δ ppm 8.68 (dd, J=4.3, 1.8 Hz, 1H) 8.57 (dd, J=8.1, 2.0 Hz, 1H) 7.89 (d, J=6.0 Hz, 1H) 7.69 (d, J=8.1 Hz, 2H) 7.52-7.58 (m, 3H) 7.50 (dd, J=8.1, 4.5 Hz, 1H) 7.40-7.46 (m, 2H) 7.33 (d, J=8.6 Hz, 2H) 7.11 (br. s, 2H) 3.88-3.96 (m, 1H) 3.84 (s, 2H) 3.44 (s, 3H) 2.12 (br. s., 2H) 1.98-2.07 (m, 3H) 1.81-1.88 (m, 2H) 1.75-1.81 (m, 2H) 1.73 (br. s., 2H) 1.37 (d, J=12.1 Hz, 2H).

Example 8 rel-3-[4-((1S,2R,3R,5S,7S)-5-amino-adamantan-2-ylcarbamoyl)-benzyl]-4-oxo-1-phenyl-1,4-dihydro-[1,8]naphthyridine-2-carboxylic acid methyl ester

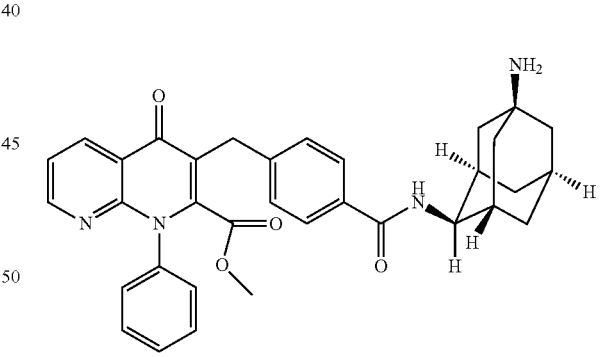

A mixture of 3-[4-((1S,2R,3R,5S,7S)-5-hydroxy-adamantan-2-ylcarbamoyl)-benzyl]-4-oxo-1-phenyl-1,4-dihydro-[1,8]naphthyridine-2-carboxylic acid methyl ester (103.3 mg, 183 μmol) chloroacetonitrile (83.0 mg, 69.4 μL, 1.1 mmol) in glacial acetic acid (87.3 μL) cooled to 0° C. was treated with concentrated sulfuric acid (162 mg, 87.9 μL, 1.65 mmol). The reaction was stirred at 0° C. for 1 h. At this time, the reaction was diluted with water and then neutralized with a saturated aqueous sodium bicarbonate solution. This solution was extracted into methylene chloride (3×30 mL), dried over sodium sulfate, filtered and concentrated in vacuo to afford 3-{4-[(1S,2R,3R,5S,7S)-5-(2-chloro-acetylamino)-adamantan-2-ylcarbamoyl]-benzyl}-4-oxo-1-phenyl-1,4-dihydro-[1,8]naphthyridine-2-carboxylic acid methyl ester. This material was used without further purification.

A solution of 3-{4-[(1S,2R,3R,5S,7S)-5-(2-chloro-acetylamino)-adamantan-2-ylcarbamoyl]-benzyl}-4-oxo-1-phenyl-1,4-dihydro-[1,8]naphthyridine-2-carboxylic acid methyl ester (117 mg, 183 μmol) and thiourea (19.5 mg, 256 μmol) in ethanol (1.52 mL) cooled to 0° C. was treated with glacial acetic acid (305 μL). The reaction was heated to reflux where it stirred overnight. At this time, the reaction was cooled to 25° C., diluted with water (5 mL) and neutralized by the dropwise addition of a saturated aqueous sodium bicarbonate solution. This solution was then extracted with methylene chloride (3×30 mL). The organics were dried over sodium sulfate, filtered and concentrated in vacuo. Flash chromatography (4 g, 2-10% methanol/methylene chloride) followed by supercritical fluid chromatography column: YMC PVA-SIL; modifier: 40% ethanol modifier; flow rate: 60 mL; wavelength: 250 nM) afforded 3-[4-((1S,2R,3R,5S,7S)-5-amino-adamantan-2-ylcarbamoyl)-benzyl]-4-oxo-1-phenyl-1,4-dihydro-[1,8]naphthyridine-2-carboxylic acid methyl ester (10.6 mg, 10.3%) a white solid. ES+-HRMS m/e calcd for $C_{34}H_{34}N_4O_4$ [M+H+] 563.2653. Found 563.2645; $^1$H NMR (300 MHz, DMSO-$d_6$) δ ppm 8.68 (dd, J=4.4, 1.9 Hz, 1H) 8.57 (dd, J=7.8, 1.9 Hz, 1H) 7.69 (d, J=8.2 Hz, 2H) 7.64-7.75 (m, 1H) 7.40-7.58 (m, 6H) 7.33 (d, J=8.2 Hz, 2H) 4.32-4.39 (m, 1H) 3.84 (s, 3H) 3.44 (s, 3H) 2.07 (br. s., 2H) 1.77-1.98 (m, 3H) 1.53-1.68 (m, 4H) 1.16-1.50 (m, 6H)

Example 9 rel-3-[4-((1S,2S,3R,5S,7S)-5-Amino-adamantan-2-ylcarbamoyl)-benzyl]-7-chloro-4-oxo-1-phenyl-1,4-dihydro-quinoline-2-carboxylic acid methyl ester

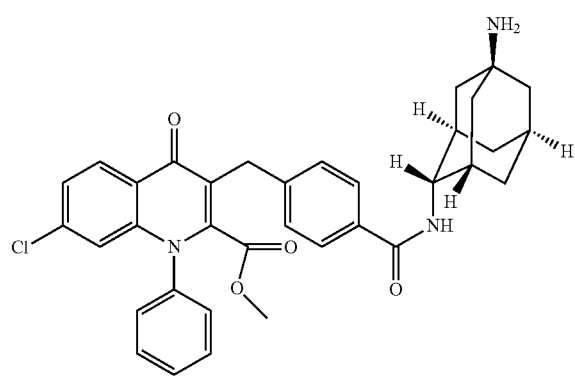

A mixture of 7-chloro-3-[4-((1S,2S,3R,5S,7S)-5-hydroxy-adamantan-2-ylcarbamoyl)-benzyl]-4-oxo-1-phenyl-1,4-dihydro-quinoline-2-carboxylic acid methyl ester (1.01 g, 1.69 mmol), and chloroacetonitrile (759 mg, 635 μL, 10.1 mmol) in glacial acetic acid (2.5 mL) cooled to 0° C. was treated with concentrated sulfuric acid (4.6 g, 2.5 mL, 46.9 mmol). The reaction was stirred at 0° C. for 1 h. At this time, the reaction was then allowed to gradually warm to 25° C. where it stirred for 36 h. At this time, more chloroacetonitrile (759 mg, 635 μL, 10.1 mmol) was added. The reaction was stirred at 25° C. for an additional 18 h. At this time, the reaction was diluted with water (50 mL) and brought to pH 5-6 with a saturated aqueous sodium bicarbonate solution. This solution was then extracted with a solution of 10% methanol/methylene chloride (3×100 mL). The combined organics were dried over sodium sulfate, filtered, and concentrated in vacuo to afford 7-chloro-3-{4-[(1S,2S,3R,5S,7S)-5-(2-chloro-acetylamino)-adamantan-2-ylcarbamoyl]-benzyl}-4-oxo-1-phenyl-1,4-dihydro-quinoline-2-carboxylic acid methyl ester as a white foamy solid. This material was used without further purification in the next reaction.

A solution of 7-chloro-3-{4-[(1S,2S,3R,5S,7S)-5-(2-chloro-acetylamino)-adamantan-2-ylcarbamoyl]-benzyl}-4-oxo-1-phenyl-1,4-dihydro-quinoline-2-carboxylic acid methyl ester (1.14 g, 1.69 mmol) in 200 proof ethanol (15 mL) was treated with thiourea (0.19 g, 2.5 mmol). The mixture was cooled to 0° C. in an ice/water bath and was then treated with glacial acetic acid (3 mL). The flask was then fitted with a reflux condenser and was warmed to 100° C. The reaction was warmed to 100° C. for 18 h. At this time, the reaction was cooled to 25° C. and was diluted with water (50 mL). The resulting thick gel was neutralized to pH 6 with a saturated aqueous sodium bicarbonate solution. This solution was extracted with a solution of 10% methanol/methylene chloride. The combined organics were dried over magnesium sulfate, filtered, rinsed with methylene chloride and concentrated in vacuo to afford 3-[4-((1S,2S,3R,5S,7S)-5-amino-adamantan-2-ylcarbamoyl)-benzyl]-7-chloro-4-oxo-1-phenyl-1,4-dihydro-quinoline-2-carboxylic acid methyl ester as a viscous, clear solid. Further purification using supercritical fluid chromatography (pyr-amide column; $CO_2$ pressure: 100 bar; flow rate: 2 mL/min; modifier: 35% methanol) afforded 3-[4-((1S,2S,3R,5S,7S)-5-amino-adamantan-2-ylcarbamoyl)-benzyl]-7-chloro-4-oxo-1-phenyl-1,4-dihydro-quinoline-2-carboxylic acid methyl ester (0.31 g, 31%) as a white solid: ES+-HRMS m/e calcd for $C_{35}H_{34}ClN_3O_4$ [M+H+] 596.2311 found 596.2302; $^1$H NMR (400 MHz, DMSO-$d_6$) δ ppm 8.22 (d, J=8.7 Hz, 1H) 7.79 (d, J=6.4 Hz, 1H) 7.63-7.72 (m, 5H) 7.57 (dd, J=6.6, 3.0 Hz, 2H) 7.47 (dd, J=8.7, 2.0 Hz, 1H) 7.32 (d, J=8.3 Hz, 2H) 6.71 (d, J=2.0 Hz, 1H) 3.90 (br. s., 1H) 3.82 (s, 2H) 3.44 (s, 3H) 1.87-2.18 (m, 7H) 1.47-1.68 (m, 6H) 1.31 (d, J=12.3 Hz, 2H).

rel-3-[4-((1S,2S,3R,5S,7S)-5-Amino-adamantan-2-ylcarbamoyl)-benzyl]-7-chloro-4-oxo-1-phenyl-1,4-dihydro-quinoline-2-carboxylic acid methyl ester hydrochloride salt

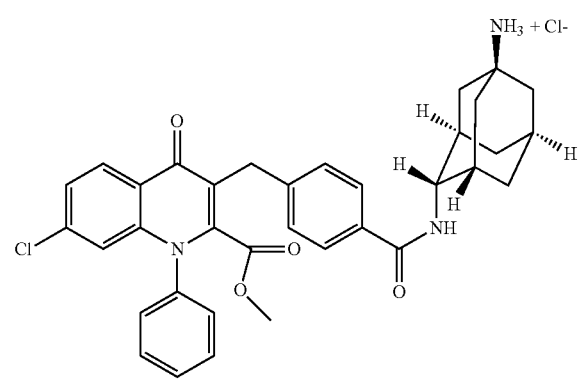

A mixture of 3-[4-((1S,2S,3R,5S,7S)-5-amino-adamantan-2-ylcarbamoyl)-benzyl]-7-chloro-4-oxo-1-phenyl-1,4- dihydro-quinoline-2-carboxylic acid methyl ester (26 mg, 43.6 µmol) was diluted with dioxane (5 mL). The solution was heated with a heat gun to fully dissolve all of the particulates. The resulting solution was allowed to cool to 25° C. At this time, the solution was treated with a 0.5M solution of hydrochloric acid in dioxane. Upon the dropwise addition of this acidic solution, a white precipitate formed. A total of 20 drops of 0.5M solution of hydrochloric acid in dioxane was added. The resulting solids were collected by filtration through a medium fritted sintered glass funnel, washed with hexanes, and dried in vacuo to afford 3-[4-((1S,2S,3R,5S,7S)-5-Amino-adamantan-2-ylcarbamoyl)-benzyl]-7-chloro-4-oxo-1-phenyl-1,4-dihydro-quinoline-2-carboxylic acid methyl ester hydrochloride salt (25.7 mg, 93.1%) as a white solid. ES$^+$-HRMS m/e calcd for $C_{35}H_{34}ClN_3O_4$ [M+H$^+$] 596.2311. Found 596.2309; $^1$H NMR (300 MHz, DMSO-d$_6$) δ ppm 8.23 (d, J=8.7 Hz, 1H) 7.93 (d, J=6.6 Hz, 1H) 7.86 (br. s., 3H) 7.61-7.74 (m, 5H) 7.52-7.61 (m, 2H) 7.48 (dd, J=8.7, 1.9 Hz, 1H) 7.34 (d, J=8.1 Hz, 2H) 6.72 (d, J=1.9 Hz, 1H) 3.94 (br. s., 1H) 3.83 (s, 2H) 3.44 (s, 3H) 2.00-2.21 (m, 5H) 1.76-1.96 (m, 6H) 1.39 (d, J=11.1 Hz, 2H).

Example 10 rel-3-[4-((1S,2S,3R,5S,7S)-5-Acetylamino-adamantan-2-ylcarbamoyl)-benzyl]-7-chloro-4-oxo-1-phenyl-1,4-dihydro-quinoline-2-carboxylic acid methyl ester

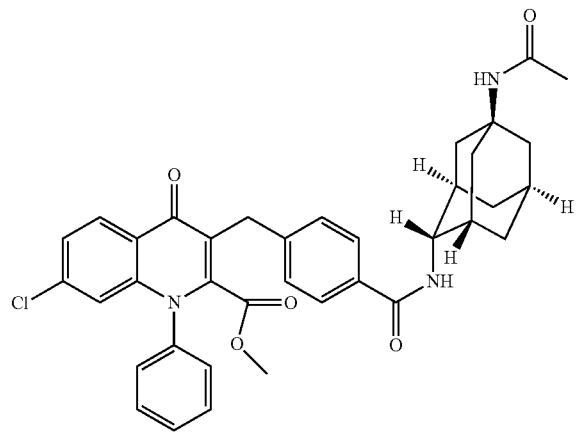 [SMILES: COC(=O)c1c(Cc2ccc(C(=O)N[C@@H]3[C@@H]4C[C@@H]5C[C@H]3C[C@@](NC(C)=O)(C5)C4)cc2)c(=O)c2ccc(Cl)cc2n1-c1ccccc1]

A solution of 3-(4-carboxy-benzyl)-7-chloro-4-oxo-1-phenyl-1,4-dihydro-quinoline-2-carboxylic acid methyl ester (45.1 mg, 101 µmol), benzotriazol-1-yloxytris(dimethylamino)-phosphonium hexafluorophosphate (71.4 mg, 161 µmol) and N,N-diisopropylethylamine (44.4 mg, 60.0 µL, 342 µmol) in methylene chloride (1 mL) was treated with N-(4-amino-adamantan-1-yl)-acetamide (see for example PCT WO2008/138920 A1, 27.4 mg, 132 µmol). The resulting reaction mixture was treated with more methylene chloride (1 mL) to assist in solubilizing the reaction. The reaction mixture was shaken at 25° C. for 2 d. At this time, the reaction mixture was concentrated in vacuo to afford a light yellow gum. Supercritical fluid chromatography (OD column; 50% methanol) followed by lyophilization from acetonitrile/water afforded 3-[4-((1S,2S,3R,5S,7S)-5-acetylamino-adamantan-2-ylcarbamoyl)-benzyl]-7-chloro-4-oxo-1-phenyl-1,4-dihydro-quinoline-2-carboxylic acid methyl ester (45 mg, 75%) as a white solid. ES$^+$-HRMS m/e calcd for $C_{37}H_{36}ClN_3O_5$ [M+H$^+$] 638.2416. Found 6382415; $^1$H NMR (300 MHz, DMSO-d$_6$) δ ppm 8.23 (d, J=8.6 Hz, 1H) 7.82 (d, J=6.3 Hz, 1H) 7.62-7.72 (m, 5H) 7.52-7.62 (m, 2H) 7.47 (dd, J=8.6, 1.9 Hz, 1H) 7.28-7.40 (m, 3H) 6.71 (d, J=1.9 Hz, 1H) 3.89-3.98 (m, 1H) 3.82 (s, 2H) 3.44 (s, 3H) 1.85-2.11 (m, 11H) 1.75 (s, 3H) 1.39 (d, J=11.8 Hz, 2H).

Example 11 rel-7-Chloro-3-{4-[(1S,2S,3R,5S,7S)-5-(2,2-dimethyl-propionylamino)-adamantan-2-ylcarbamoyl]-benzyl}-4-oxo-1-phenyl-1,4-dihydro-quinoline-2-carboxylic acid methyl ester

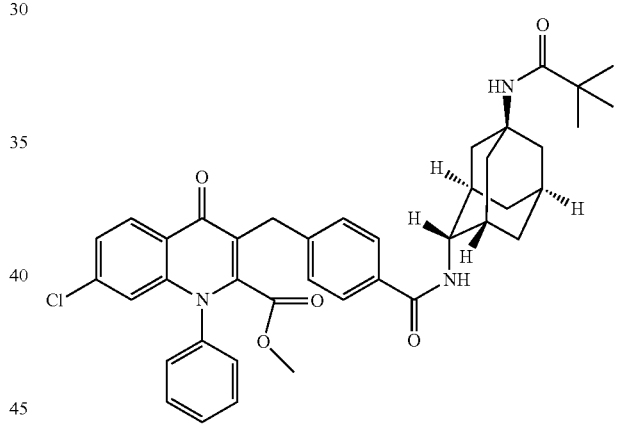

A solution of 3-[4-((1S,2S,3R,5S,7S)-5-amino-adamantan-2-ylcarbamoyl)-benzyl]-7-chloro-4-oxo-1-phenyl-1,4-dihydro-quinoline-2-carboxylic acid methyl ester (99.8 mg, 167 µmol) in methylene chloride (5.0 mL) was treated with triethylamine (84.9 mg, 117 µL, 839 µmol), trimethylacetyl chloride (51 mg, 52 µL, 423 µmol), and catalytic N,N-dimethylaminopyridine (spatula tip). The reaction was stirred at 25° C. for 2 d. At this time, flash chromatography (AnaLogix IntelliFlash 280, 12 g silica gel column, 1%-10% methanol/methylene chloride) afforded 7-chloro-3-{4-[(1S,2S,3R,5S,7S)-5-(2,2-dimethyl-propionylamino)-adamantan-2-ylcarbamoyl]-benzyl}-4-oxo-1-phenyl-1,4-dihydro-quinoline-2-carboxylic acid methyl ester (80.9 mg, 71%) as a white solid. ES$^+$-HRMS m/e calcd for $C_{40}H_{42}ClN_3O_5$ [M+H$^+$] 680.2886. Found 680.2867; $^1$H NMR (300 MHz, DMSO-d$_6$) δ ppm 8.23 (d, J=8.7 Hz, 1H) 7.81 (d, J=6.6 Hz, 1H) 7.63-7.74 (m, 5H) 7.53-7.61 (m, 2H) 7.47 (dd, J=8.7, 1.9 Hz, 1H) 7.32 (d, J=8.3 Hz, 2H) 6.71 (d, J=1.9 Hz, 1H) 6.40 (s, 1H) 3.95 (d, J=5.7 Hz, 1H) 3.82 (s, 2H) 3.44 (s, 3H) 1.89-2.13 (m, 11H) 1.39 (d, J=11.7 Hz, 2H) 1.07 (s, 9H).

Example 12 rel-3-{4-[(1S,2S,3R,5S,7S)-5-(2-Acetoxy-2-methyl-propionylamino)-adamantan-2-ylcarbamoyl]-benzyl}-7-chloro-4-oxo-1-phenyl-1,4-dihydro-quinoline-2-carboxylic acid methyl ester

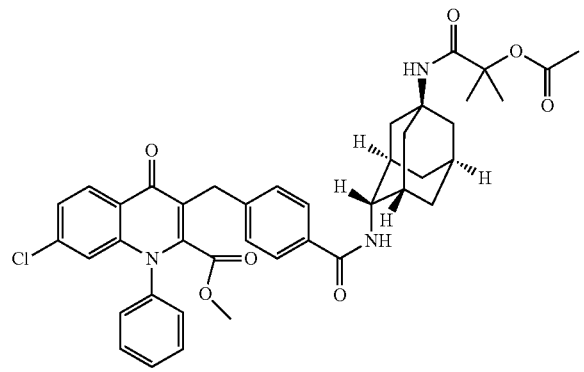 [SMILES: COC(=O)c1c(Cc2ccc(C(=O)N[C@@H]3[C@@H]4C[C@@H]5C[C@H]3C[C@@](NC(=O)C(C)(C)OC(C)=O)(C5)C4)cc2)c(=O)c2ccc(Cl)cc2n1-c1ccccc1]

A solution of 3-[4-((1S,2S,3R,5S,7S)-5-amino-adamantan-2-ylcarbamoyl)-benzyl]-7-chloro-4-oxo-1-phenyl-1,4-dihydro-quinoline-2-carboxylic acid methyl ester (250 mg, 419 μmol) in methylene chloride (11.5 mL) was treated with triethylamine (211 mg, 290 μL, 2.08 mmol), 2-acetoxyisobutyryl chloride (173 mg, 152 μL, 1.05 mmol) and catalytic N,N-dimethylaminopyridine (spatula tip). The reaction was stirred at 25° C. for 18 h. At this time, flash chromatography (AnaLogix IntelliFlash 280, 40 g silica gel column, 60%-100% ethyl acetate/hexanes) afforded 3-{4-[(1S,2S,3R,5S,7S)-5-(2-acetoxy-2-methyl-propionylamino)-adamantan-2-ylcarbamoyl]-benzyl}-7-chloro-4-oxo-1-phenyl-1,4-dihydro-quinoline-2-carboxylic acid methyl ester (291.1 mg, 96%) as an off-white solid. ES$^+$-HRMS m/e calcd for $C_{41}H_{42}N_3O_7Cl$ [M+H$^+$] 724.2784. Found 724.2788. $^1$H NMR (400 MHz, DMSO-$d_6$) δ ppm 8.23 (d, J=8.8 Hz, 1H) 7.83 (d, J=6.5 Hz, 1H) 7.63-7.72 (m, 5H) 7.53-7.60 (m, 2H) 7.47 (dd, J=8.8, 1.9 Hz, 1H) 7.32 (d, J=8.5 Hz, 2H) 6.67-6.74 (m, 2H) 3.95 (br. s., 1H) 3.82 (s, 2H) 3.44 (s, 3H) 2.00 (s, 3H) 1.84-2.13 (m, 11H) 1.43 (s, 6H) 1.39 (d, J=12.5 Hz, 2H).

Example 13 rel-7-Chloro-3-{4-[(1S,2S,3R,5S,7S)-5-(2-hydroxy-2-methyl-propionylamino)-adamantan-2-ylcarbamoyl]-benzyl}-4-oxo-1-phenyl-1,4-dihydro-quinoline-2-carboxylic acid methyl ester

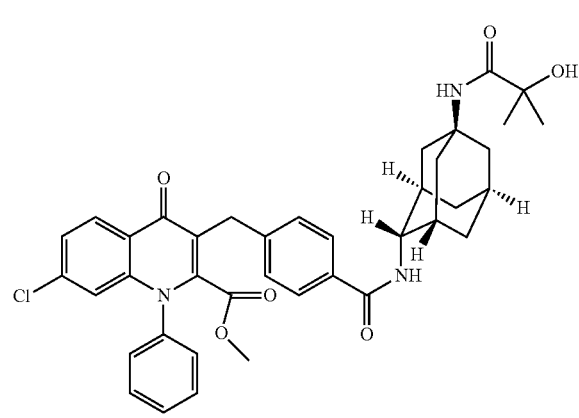 [SMILES: COC(=O)c1c(Cc2ccc(C(=O)N[C@@H]3[C@@H]4C[C@@H]5C[C@H]3C[C@@](NC(=O)C(C)(C)O)(C5)C4)cc2)c(=O)c2ccc(Cl)cc2n1-c1ccccc1]

A solution of 3-{4-[(1S,2S,3R,5S,7S)-5-(2-acetoxy-2-methyl-propionylamino)-adamantan-2-ylcarbamoyl]-benzyl}-7-chloro-4-oxo-1-phenyl-1,4-dihydro-quinoline-2-carboxylic acid methyl ester (98.8 mg, 136 μmol) in methanol (1 mL) was treated with potassium carbonate (101.3 mg, 733 μmol). The reaction was stirred at 25° C. for 30-35 min. At this time, the reaction was partitioned between a 1N aqueous hydrochloric acid solution (25 mL) and methylene chloride (25 mL). The layers were shaken and separated. The aqueous layer was back extracted with methylene chloride (25 mL). The combined organics were washed with a saturated aqueous sodium chloride solution (25 mL), dried over magnesium sulfate, filtered, rinsed with methylene chloride, and concentrated in vacuo. Flash chromatography (AnaLogix IntelliFlash 280 chromatography, 12 g silica gel column, 75%-100% ethyl acetate/hexanes) afforded 7-chloro-3-{4-[(1S,2S,3R,5S,7S)-5-(2-hydroxy-2-methyl-propionylamino)-adamantan-2-ylcarbamoyl]-benzyl}-4-oxo-1-phenyl-1,4-dihydro-quinoline-2-carboxylic acid methyl ester (74.1 mg, 80%) as a white solid. ES$^+$-HRMS m/e calcd for $C_{39}H_{40}N_3O_6Cl$ [M+H$^+$] 682.2679 found 682.2680. $^1$H NMR (400 MHz, DMSO-$d_6$) δ ppm 8.23 (d, J=8.8 Hz, 1H) 7.84 (d, J=6.5 Hz, 1H) 7.62-7.73 (m, 7H) 7.53-7.61 (m, 3H) 7.47 (dd, J=8.8, 1.9 Hz, 2H) 7.33 (d, J=8.3 Hz, 3H) 6.84 (s, 1H) 6.71 (d, J=1.9 Hz, 1H) 5.45 (s, 2H) 3.97 (d, J=5.8 Hz, 2H) 3.82 (s, 3H) 3.44 (s, 3H) 1.90-2.12 (m, 11H) 1.41 (d, J=12.3 Hz, 2H) 1.21 (s, 6H).

Example 14 rel-7-Chloro-3-[4-((1S,2S,3R,5S,7S)-5-cyclopropanesulfonylamino-adamantan-2-ylcarbamoyl)-benzyl]-4-oxo-1-phenyl-1,4-dihydro-quinoline-2-carboxylic acid methyl ester

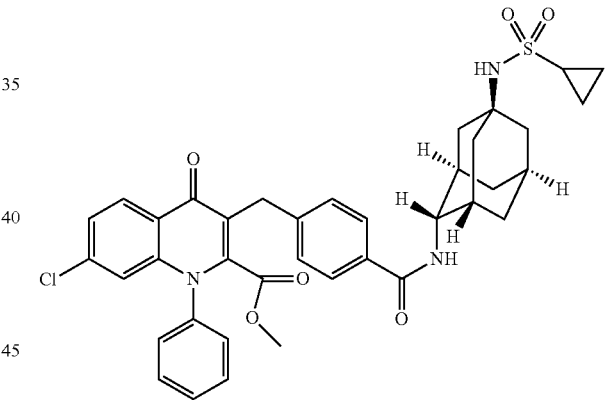

A solution of 3-[4-((1S,2S,3R,5S,7S)-5-amino-adamantan-2-ylcarbamoyl)-benzyl]-7-chloro-4-oxo-1-phenyl-1,4-dihydro-quinoline-2-carboxylic acid methyl ester (39.0 mg, 65.4 μmol) in methylene chloride (2 mL) was treated with triethylamine (33.4 mg, 46 μL, 330 μmol), cyclopropanesulfonyl chloride (11.0 mg, 8.0 μL, 78.5 μmol), and catalytic N,N-dimethylaminopyridine (spatula tip). The reaction was stirred at 25° C. overnight. At this time, flash chromatography (AnaLogix IntelliFlash 280, 4 g silica gel column, 1%-10% methanol/methylene chloride) afforded 7-chloro-3-[4-((1S,2S,3R,5S,7S)-5-cyclopropanesulfonylamino-adamantan-2-ylcarbamoyl)-benzyl]-4-oxo-1-phenyl-1,4-dihydro-quinoline-2-carboxylic acid methyl ester as a white solid: (2.9 mg, 6%). ES$^+$-HRMS m/e calcd for $C_{38}H_{38}N_3O_6SCl$ [M+H$^+$] 700.2243. Found 700.2239. $^1$H NMR (300 MHz, DMSO-$d_6$) δ ppm 8.22 (d, J=8.7 Hz, 1H) 7.82 (d, J=6.6 Hz, 1H) 7.62-7.71 (m, 5H) 7.52-7.59 (m, 1H) 7.47 (dd, J=8.7, 1.9 Hz, 1H) 7.32 (d, J=8.3 Hz, 1H) 6.87 (s, 1H) 6.71 (d, J=1.9 Hz, 1H) 3.94 (br. s., 1H) 3.82 (s, 2H) 3.43 (s, 3H) 2.54-2.58 (m, 1H) 1.84-2.12 (m, 11H) 1.37 (d, J=11.3 Hz, 2H) 0.84-0.99 (m, 4H).

Example 15 rel-7-Chloro-3-[4-((1S,2S,3R,5S,7S)-5-methane-sulfonylamino-adamantan-2-ylcarbamoyl)-benzyl]-4-oxo-1-phenyl-1,4-dihydro-quinoline-2-carboxylic acid methyl ester

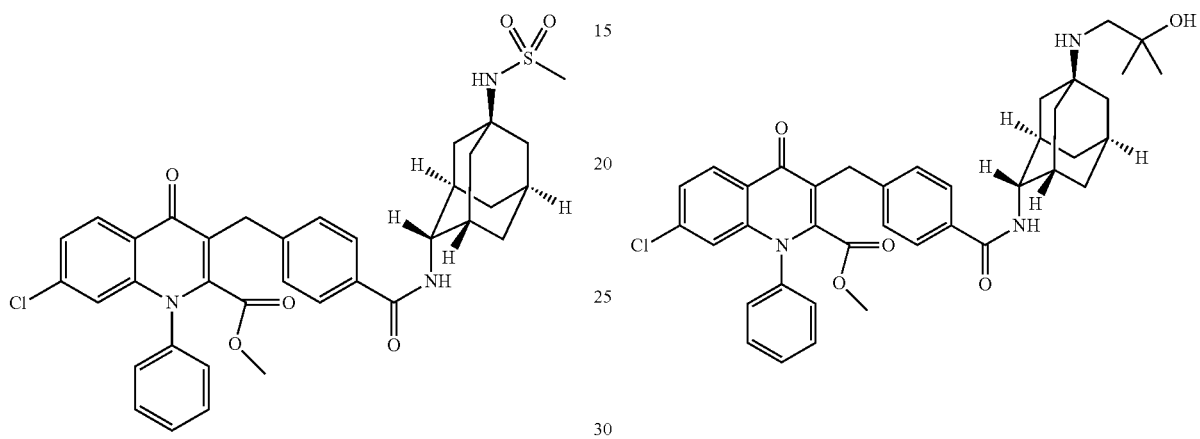

A solution of 3-[4-((1S,2S,3R,5S,7S)-5-amino-adamantan-2-ylcarbamoyl)-benzyl]-7-chloro-4-oxo-1-phenyl-1,4-dihydro-quinoline-2-carboxylic acid methyl ester (48.0 mg, 80.5 µmol) in methylene chloride (2.5 mL) was treated with triethylamine (42.8 mg, 59 µL, 423 µmol), methanesulfonyl chloride (22.0 mg, 15.0 µL, 192 µmol), and catalytic N,N-dimethylaminopyridine (spatula tip). The reaction was stirred at 25° C. overnight. At this time, the reaction was diluted with methylene chloride (25 mL), washed with water (25 mL), dried over magnesium sulfate, filtered, rinsed with methylene chloride and concentrated in vacuo. Flash chromatography (AnaLogix IntelliFlash 280, 12 g silica gel column, 1%-5% methanol/methylene chloride) afforded 7-chloro-3-[4-((1S,2S,3R,5S,7S)-5-methanesulfonylamino-adamantan-2-ylcarbamoyl)-benzyl]-4-oxo-1-phenyl-1,4-dihydro-quinoline-2-carboxylic acid methyl ester (44.0 mg, 81%) as a white solid. ES$^+$-HRMS m/e calcd for $C_{36}H_{36}ClN_3O_6S$ [M+H$^+$] 674.2086. Found 674.2074. $^1$H NMR (400 MHz, DMSO-d$_6$) δ ppm 8.23 (d, J=8.7 Hz, 1H) 7.85 (br. s., 1H) 7.62-7.72 (m, 5H) 7.57 (br. s., 2H) 7.47 (d, J=7.5 Hz, 1H) 7.32 (d, J=7.3 Hz, 2H) 6.90 (br. s., 1H) 6.71 (s, 1H) 3.93 (br. s., 1H) 3.82 (br. s., 2H) 3.44 (br. s., 3H) 2.95 (s, 3H) 1.82-2.12 (m, 11H) 1.37 (d, J=12.1 Hz, 2H).

Example 16 rel-7-Chloro-3-{4-[(1S,2S,3R,5S,7S)-5-(2-hydroxy-2-methyl-propylamino)-adamantan-2-ylcarbamoyl]-benzyl}-4-oxo-1-phenyl-1,4-dihydro-quinoline-2-carboxylic acid methyl ester A solution of 3-[4-((1S,2S,3R,5S,7S)-5-amino-adamantan-2-ylcarbamoyl)-benzyl]-7-chloro-4-oxo-1-phenyl-1,4-dihydro-quinoline-2-carboxylic acid methyl ester (48.7 mg, 81.7 µmol) in methanol (0.5 mL) was treated with 2,2-dimethyloxirane (8.0 µL, 90.1 µmol). The flask was tightly capped and warmed to 100° C. for 2.75 h. At this time, the reaction had evaporated to dryness. The vial was charged again with methanol (500 µL) and a second aliquot of 2,2-dimethyloxirane (16 µL). The flask was tightly sealed and warmed to 100° C. overnight. At this time, the reaction was concentrated in vacuo. Preparative chromatography (YMC PVA-SIL 3×35 preparatory column; flow rate=70 mL; wavelength=220 nM; modifier—methanol) afforded 7-chloro-3-{4-[(1S,2S,3R,5S,7S)-5-(2-hydroxy-2-methyl-propylamino)-adamantan-2-ylcarbamoyl]-benzyl}-4-oxo-1-phenyl-1,4-dihydro-quinoline-2-carboxylic acid methyl ester (23.6 mg, 43%) as a white solid (23.6 mg, 43%); ES$^+$-HRMS m/e calcd for $C_{39}H_{42}ClN_3O_5$ [M+H$^+$] 668.2886. Found 668.2877. $^1$H NMR (300 MHz, DMSO-d$_6$) δ ppm 8.22 (d, J=8.7 Hz, 1H) 7.78 (d, J=6.2 Hz, 1H) 7.62-7.72 (m, 5H) 7.53-7.59 (m, 2H) 7.47 (dd, J=8.7, 1.8 Hz, 1H) 7.32 (d, J=8.1 Hz, 2H) 6.71 (d, J=1.8 Hz, 1H) 4.10 (br. s., 1H) 3.91 (br. s., 1H) 3.82 (s, 2H) 3.43 (s, 3H) 2.40 (br. s., 2H) 1.87-2.19 (m, 5H) 1.61 (d, J=18.3 Hz, 6H) 1.35 (d, J=12.2 Hz, 2H) 1.07 (s, 6H).

Example 17 rel-3-[4-((1S,2S,3R,5S,7S)-5-Acetylamino-adamantan-2-ylcarbamoyl)-benzyl]-4-oxo-1-phenyl-1,4-dihydro-[1,8]naphthyridine-2-carboxylic acid methyl ester

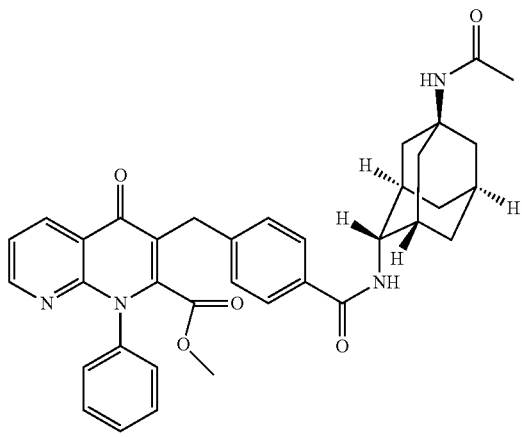 [SMILES: COC(=O)c1c(Cc2ccc(C(=O)N[C@@H]3[C@@H]4C[C@@H]5C[C@H]3C[C@@](NC(C)=O)(C5)C4)cc2)c(=O)c2cccnc2n1-c1ccccc1]

A solution of 3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester (98.8 mg, 176 μmol) in methylene chloride (5 mL) was treated with triethylamine (124 μL, 890 μmol), acetyl chloride (31 μL, 436 μmol), and catalytic N,N-dimethylaminopyridine (spatula tip). The reaction was stirred at 25° C. overnight. At this time, flash chromatography (AnaLogix IntelliFlash 280, 25 g silica gel column, 1%-10% methanol/methylene chloride) afforded 3-[4-((1S,2S,3R,5S,7S)-5-acetylamino-adamantan-2-ylcarbamoyl)-benzyl]-4-oxo-1-phenyl-1,4-dihydro-[1,8]naphthyridine-2-carboxylic acid methyl ester (79.5 mg, 75%) as a white solid. ES$^+$-HRMS m/e calcd for $C_{36}H_{36}N_4O_5$ [M+H$^+$] 605.2759. Found 605.2758. $^1$H NMR (300 MHz, DMSO-d$_6$) δ ppm 8.68 (dd, J=4.3, 1.6 Hz, 1H) 8.58 (dd, J=7.9, 1.6 Hz, 1H) 7.82 (d, J=6.8 Hz, 1H) 7.69 (d, J=8.2 Hz, 2H) 7.42-7.59 (m, 6H) 7.36 (br. s., 1H) 7.34 (d, J=8.2 Hz, 2H) 3.96 (br. s., 1H) 3.84 (s, 2H) 3.43 (s, 3H) 1.89-2.10 (m, 11H) 1.75 (s, 3H) 1.40 (d, J=12.2 Hz, 2H).

Example 18 rel-3-[4-((1S,2S,3R,5S,7S)-5-Cyclopropanesulfonylamino-adamantan-2-ylcarbamoyl)-benzyl]-4-oxo-1-phenyl-1,4-dihydro-[1,8]naphthyridine-2-carboxylic acid methyl ester

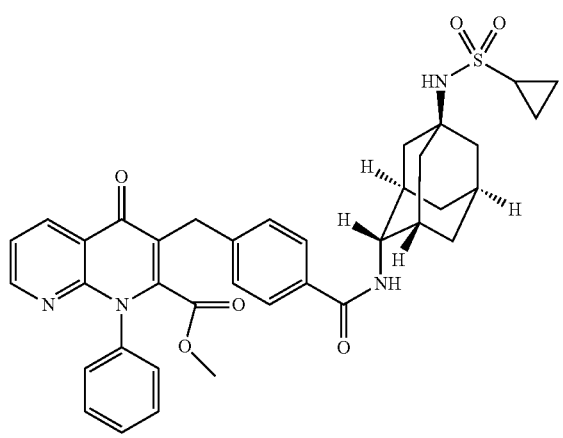 [SMILES: COC(=O)c1c(Cc2ccc(C(=O)N[C@@H]3[C@@H]4C[C@@H]5C[C@H]3C[C@@](NS(=O)(=O)C3CC3)(C5)C4)cc2)c(=O)c2cccnc2n1-c1ccccc1]

A solution of 3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester (73.0 mg, 130 μmol) in methylene chloride (4.0 mL) was treated with triethylamine (93 μL, 667 μmol), cyclopropanesulfonyl chloride (34 μL, 334 μmol), and catalytic N,N-dimethylaminopyridine (spatula tip). The reaction was stirred at 25° C. overnight. At this time, a second aliquot of cyclopropanesulfonyl chloride (46.9 mg, 34 μL, 334 μmol) was added. The reaction stirred at 25° C. overnight. At this time, the reaction was purified. Flash chromatography (AnaLogix IntelliFlash 280, 12 g silica gel column, 1%-10% methanol/methylene chloride) afforded 3-[4-((1S,2S,3R,5S,7S)-5-cyclopropanesulfonylamino-adamantan-2-ylcarbamoyl)-benzyl]-4-oxo-1-phenyl-1,4-dihydro-[1,8]naphthyridine-2-carboxylic acid methyl ester (39.1 mg, 45.2%) as a white solid. ES$^+$-HRMS m/e calcd for $C_{37}H_{38}N_4O_6S$ [M+H$^+$] 667.2585. Found 667.2576. $^1$H NMR (300 MHz, DMSO-d$_6$) δ ppm 8.68 (dd, J=4.4, 2.0 Hz, 1H) 8.57 (dd, J=7.9, 2.0 Hz, 1H) 7.83 (d, J=6.6 Hz, 1H) 7.69 (d, J=8.3 Hz, 2H) 7.52-7.59 (m, 3H) 7.50 (dd, J=7.9, 4.4 Hz, 1H) 7.40-7.46 (m, 2H) 7.33 (d, J=8.3 Hz, 2H) 6.87 (s, 1H) 3.89-3.99 (m, 1H) 3.84 (s, 2H) 3.44 (s, 3H) 2.53-2.62 (m, 1H) 1.81-2.16 (m, 11H) 1.38 (d, J=12.1 Hz, 2H) 0.83-1.01 (m, 4H).

Example 19 rel-3-[4-((1S,2S,3R,5S,7S)-5-Methanesulfonylamino-adamantan-2-ylcarbamoyl)-benzyl]-4-oxo-1-phenyl-1,4-dihydro-[1,8]naphthyridine-2-carboxylic acid methyl ester

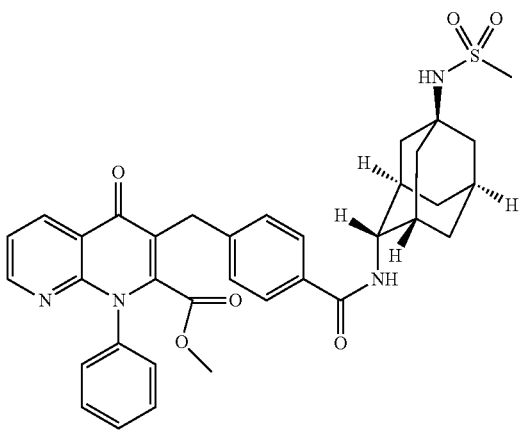 [SMILES: COC(=O)c1c(Cc2ccc(C(=O)N[C@@H]3[C@@H]4C[C@@H]5C[C@H]3C[C@@](NS(C)(=O)=O)(C5)C4)cc2)c(=O)c2cccnc2n1-c1ccccc1]

A solution of 3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester (10.3 mg, 18.3 μmol) in methylene chloride (0.5 mL) was treated with triethylamine (13 μL, 93.3 μmol), methanesulfonyl chloride (1.6 μL, 20.5 μmol), and catalytic N,N-dimethylaminopyridine (spatula tip). The reaction was stirred at 25° C. overnight. At this time, flash chromatography (AnaLogix IntelliFlash 280, 4 g silica gel column, 1%-10% methanol/methylene chloride) afforded 3-[4-((1S,2S,3R,5S,7S)-5-methanesulfonylamino-adamantan-2-ylcarbamoyl)-benzyl]-4-oxo-1-phenyl-1,4-dihydro-[1,8]naphthyridine-2-carboxylic acid methyl ester (1.6 mg, 14%) as a white solid. ES$^+$-HRMS m/e calcd for $C_{35}H_{36}N_4O_6S$ [M+H$^+$] 641.2428. Found 641.2413. $^1$H NMR (400 MHz, DMSO-d$_6$) δ ppm 8.67 (dd, J=4.4, 2.0 Hz, 1H) 8.57 (dd, J=8.0, 2.0 Hz, 1H) 7.85 (d, J=6.6 Hz, 1H) 7.68 (d, J=8.3 Hz, 2H) 7.51-7.58 (m, 3H) 7.50 (dd, J=8.0, 4.4 Hz, 1H) 7.42-7.47 (m, 1H) 7.33 (d, J=8.3 Hz, 2H) 6.89 (s, 1H) 3.92 (br. s., 1H) 3.83 (s, 2H) 3.43 (s, 3H) 2.94 (s, 3H) 1.83-2.10 (m, 11H) 1.37 (d, J=12.5 Hz, 2H).

Example 20 rel-3-{4-[(1S,2S,3R,5S,7S)-5-(2,2-Dimethyl-propionylamino)-adamantan-2-ylcarbamoyl]-benzyl}-4-oxo-1-phenyl-1,4-dihydro-[1,8]naphthyridine-2-carboxylic acid methyl ester

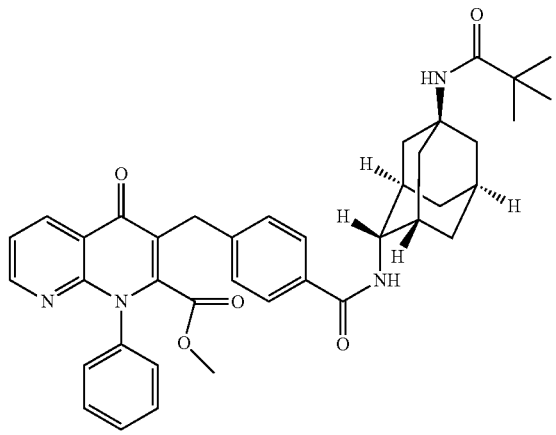 [SMILES: COC(=O)c1c(Cc2ccc(C(=O)N[C@@H]3[C@@H]4C[C@@H]5C[C@H]3C[C@@](NC(=O)C(C)(C)C)(C5)C4)cc2)c(=O)c2cccnc2n1-c1ccccc1]

A solution of 3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester (18.1 mg, 32.2 µmol) in methylene chloride (1.0 mL) was treated with triethylamine (22.5 µL, 161 µmol), trimethylacetyl chloride (10 µL, 81.3 µmol), and catalytic N,N-dimethylaminopyridine (spatula tip). The reaction was stirred at 25° C. for 2 d. At this time, flash chromatography (AnaLogix IntelliFlash 280, 12 g silica gel column, 1%-10% methanol/methylene chloride) afforded 3-{4-[(1S,2S,3R,5S,7S)-5-(2,2-dimethyl-propionylamino)-adamantan-2-ylcarbamoyl]-benzyl}-4-oxo-1-phenyl-1,4-dihydro-[1,8]naphthyridine-2-carboxylic acid methyl ester as a white solid: (13.8 mg, 66%). ES$^+$-HRMS m/e calcd for $C_{39}H_{42}N_4O_5$ [M+H$^+$] 647.3228. Found 647.3212. $^1$H NMR (300 MHz, DMSO-d$_6$) δ ppm 8.67 (dd, J=4.4, 1.9 Hz, 1H) 8.56 (dd, J=8.0, 1.9 Hz, 1H) 7.81 (d, J=6.6 Hz, 1H) 7.68 (d, J=8.3 Hz, 2H) 7.52-7.57 (m, 3H) 7.49 (dd, J=8.0, 4.4 Hz, 1H) 7.39-7.46 (m, 2H) 7.33 (d, J=8.3 Hz, 2H) 6.39 (s, 1H) 3.96 (br. s., 1H) 3.83 (s, 2H) 3.43 (s, 3H) 1.88-2.12 (m, 11H) 1.39 (d, J=10.9 Hz, 2H) 1.06 (s, 9H).

Example 21 rel-3-{4-[(1S,2S,3R,5S,7S)-5-(2-Acetoxy-2-methyl-propionylamino)-adamantan-2-ylcarbamoyl]-benzyl}-4-oxo-1-phenyl-1,4-dihydro-[1,8]naphthyridine-2-carboxylic acid methyl ester

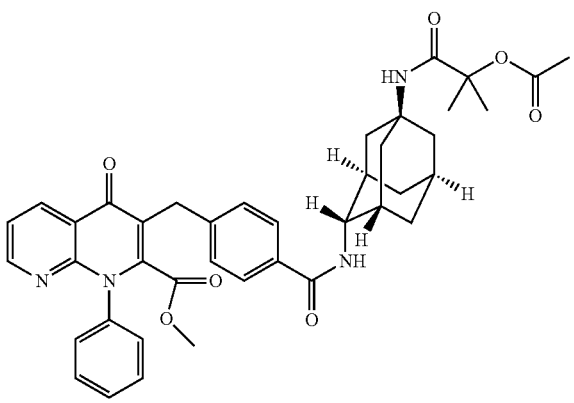 [SMILES: COC(=O)c1c(Cc2ccc(C(=O)N[C@@H]3[C@@H]4C[C@@H]5C[C@H]3C[C@@](NC(=O)C(C)(C)OC(C)=O)(C5)C4)cc2)c(=O)c2cccnc2n1-c1ccccc1]

A solution of 3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester (102.5 mg, 182 µmol) in methylene chloride (5 mL) was treated with triethylamine (126 µL, 904 µmol), 1-chloro-2-methyl-1-oxopropan-2-yl acetate (64 µL, 447 µmol) and catalytic N,N-dimethylaminopyridine (spatula tip). The reaction was stirred at 25° C. for 18 h. At this time, flash chromatography (AnaLogix IntelliFlash 280, 25 g silica gel column, 1%-10% methanol/methylene chloride) afforded 3-{4-[(1S,2S,3R,5S,7S)-5-(2-Acetoxy-2-methyl-propionylamino)-adamantan-2-ylcarbamoyl]-benzyl}-4-oxo-1-phenyl-1,4-dihydro-[1,8]naphthyridine-2-carboxylic acid methyl ester (96.2 mg, 76%) as a white solid. ES$^+$-HRMS m/e calcd for $C_{40}H_{42}N_4O_7$ [M+H$^+$] 691.3126 found 691.3129. $^1$H NMR (300 MHz, DMSO-d$_6$) δ ppm 1.26-1.54 (m, 8H) 1.84-2.15 (m, 14H) 3.39-3.50 (m, 3H) 3.84 (s, 2H) 3.94 (br. s., 1H) 6.69 (s, 1H) 7.33 (d, J=8.48 Hz, 2H) 7.38-7.61 (m, 6H) 7.69 (d, J=8.29 Hz, 2H) 7.82 (d, J=6.40 Hz, 1H) 8.57 (dd, J=7.91, 1.88 Hz, 1H) 8.68 (dd, J=4.43, 1.98 Hz, 1H).

Example 22 rel-3-{4-[(1S,2S,3R,5S,7S)-5-(2-Hydroxy-2-methyl-propionylamino)-adamantan-2-ylcarbamoyl]-benzyl}-4-oxo-1-phenyl-1,4-dihydro-[1,8]naphthyridine-2-carboxylic acid methyl ester

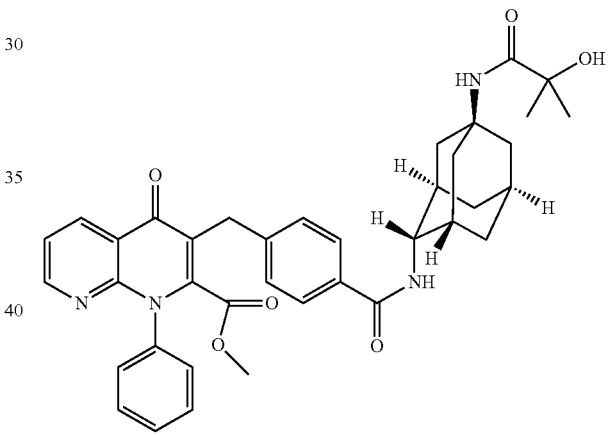

A solution of 3-{4-[(1S,2S,3R,5S,7S)-5-(2-acetoxy-2-methyl-propionylamino)-adamantan-2-ylcarbamoyl]-4-oxo-1-phenyl-1,4-dihydro-[1,8]naphthyridine-2-carboxylic acid methyl ester (69.7 mg, 101 µmol) in methanol (0.7 mL) was treated with potassium carbonate (77.5 mg, 561 µmol). The reaction was stirred at 25° C. for 1 h. At this time, the reaction was partitioned between a 1N aqueous hydrochloric acid solution (25 mL) and methylene chloride (25 mL). The layers were shaken and separated. The aqueous layer was back extracted with methylene chloride (25 mL). The combined organics were dried over magnesium sulfate, filtered, rinsed with methylene chloride, and concentrated in vacuo. Flash chromatography (AnaLogix IntelliFlash 280 chromatography, 25 g silica gel column, 1-10% methanol/methylene chloride) afforded 3-{4-[(1S,2S,3R,5S,7S)-5-(2-hydroxy-2-methyl-propionylamino)-adamantan-2-ylcarbamoyl]-benzyl}-4-oxo-1-phenyl-1,4-dihydro-[1,8]naphthyridine-2-carboxylic acid methyl ester (50.4 mg, 77%) as a white solid. ES$^+$-HRMS m/e calcd for $C_{38}H_{40}N_4O_6$ [M+H$^+$] 649.3021. Found 649.3020. $^1$H NMR (300 MHz, DMSO-d$_6$) δ 8.68 (dd, J=1.98, 4.43 Hz, 1H), 8.57 (dd, J=1.88, 7.91 Hz, 1H), 7.83 (d, J=6.40 Hz, 1H), 7.69 (d, J=8.29 Hz, 2H), 7.47-7.56 (m, 4H), 7.42-7.47 (m, 2H), 7.33 (d, J=8.48 Hz, 2H), 6.84 (s, 1H), 3.97 (br. s., 1H), 3.84 (s, 2H), 3.39-3.49 (m, 3H), 1.90-2.14 (m, 11H), 1.41 (d, J=11.49 Hz, 2H), 1.21 (s, 6H).

Example 23 rel-3-[4-((1S,2S,3R,5S,7S)-5-Hydroxy-adamantan-2-ylcarbamoyl)-2-methoxy-benzyl]-4-oxo-1-phenyl-1,4-dihydro-[1,8]naphthyridine-2-carboxylic acid methyl ester

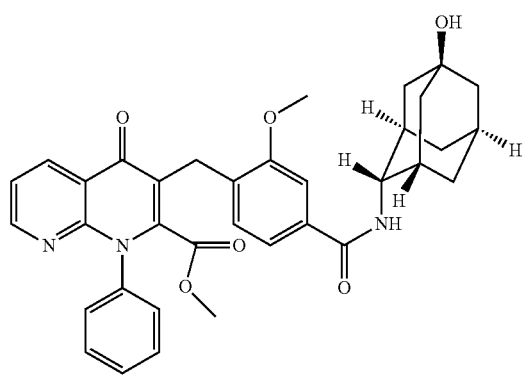 [SMILES: COC(=O)c1c(Cc2ccc(C(=O)N[C@@H]3[C@@H]4C[C@@H]5C[C@H]3C[C@@](O)(C5)C4)cc2OC)c(=O)c2cccnc2n1-c1ccccc1]

A mixture of 4-formyl-3-hydroxy-benzoic acid (1 g, 6.01 mmol) in dimethylsulfoxide (10 mL) at 25° C. was treated with potassium carbonate (5.1 g, 37.3 mmol) and methyl iodide (1.3 mL, 20.4 mmol). The reaction was stirred at 25° C. for 4 h. At this time, the reaction was diluted with water (100 mL) and then was extracted into ethyl acetate (3×50 mL). The organics were washed with water (2×100 mL), dried over anhydrous sodium sulfate, filtered and concentrated in vacuo to afford 4-formyl-3-methoxy-benzoic acid methyl ester (830.2 mg, 71.1%) as a light yellow solid. ES+-HRMS m/e calcd for $C_{10}H_{10}O_4$ [M+H+] 195.0652. Found 195.0652.

A mixture of 1-(2-phenylamino-pyridin-3-yl)-ethanone (833 mg, 3.92 mmol) in methanol (16.5 mL) at 25° C. was treated with 4-formyl-3-methoxy-benzoic acid methyl ester (508 mg, 2.61 mmol) and sodium methoxide in methanol (4.37M, 1.2 mL, 5.23 mmol). The reaction was stirred at 25° C. for 48 h. At this time, the reaction was diluted with water (100 mL), neutralized with a 1N aqueous hydrochloric acid solution, and extracted with methylene chloride (3×75 mL). The combined organics were dried over sodium sulfate filtered and concentrated in vacuo. Flash chromatography (40 g silica column, 10-50% ethyl acetate/hexanes) afforded 3-methoxy-4-[(E)-3-oxo-3-(2-phenylamino-pyridin-3-yl)-propenyl]-benzoic acid methyl ester (880 mg, 86.8%) as a red solid. ES+-HRMS m/e calcd for $C_{23}H_{20}N_2O_4$ [M+H+] 389.1496. Found 389.1494.

A solution of 3-methoxy-4-[(E)-3-oxo-3-(2-phenylamino-pyridin-3-yl)-propenyl]-benzoic acid methyl ester (875 mg, 2.25 mmol) in ethyl acetate was treated with 10% palladium on activated carbon (83 mg). The reaction was stirred under a balloon of hydrogen gas for 6 h. At this time, the reaction was filtered through a pad of Celite®, rinsed with ethyl acetate and concentrated in vacuo. LCMS indicated incomplete conversion to the desired product. Due to solubility issues, the residue was dissolved in acetone (200 mL) at 25° C. and was treated with 10% palladium on activated carbon (83 mg). The reaction was stirred under a balloon of hydrogen gas for 2 d. At this time, the reaction was filtered through a pad of Celite®, rinsed extensively with acetone and concentrated in vacuo. LCMS still indicated incomplete conversion to the desired product. The residue was dissolved in methylene chloride (150 mL) at 25° C. and was treated with 10% palladium on activated carbon (83 mg). The reaction was stirred under a balloon of hydrogen gas for 4 d. At this time, the reaction was filtered through a pad of Celite®, rinsed with methylene chloride (2×50 mL) and concentrated in vacuo. Flash chromatography (40 g silica column, 10-25% ethyl acetate/hexanes) afforded 3-methoxy-4-[3-oxo-3-(2-phenylamino-pyridin-3-yl)-propyl]-benzoic acid methyl ester (313.4 mg, 35.6%) as a yellow solid.

A solution of 3-methoxy-4-[3-oxo-3-(2-phenylamino-pyridin-3-yl)-propyl]-benzoic acid methyl ester (139.6 mg, 358 μmol) in toluene (7.15 mL) was treated with methyl oxalyl chloride (52.6 mg, 39.6 μL, 429 μmol). The reaction was heated to 130° C. for 4 h. At this time, the reaction was cooled to 25° C. and concentrated in vacuo to afford 3-methoxy-4-{3-[2-(methoxyoxalyl-phenyl-amino)-pyridin-3-yl]-3-oxo-propyl}-benzoic acid methyl ester as a brown oil. The residue was used without further purification.

A solution of 3-methoxy-4-{3-[2-(methoxyoxalyl-phenyl-amino)-pyridin-3-yl]-3-oxo-propyl}-benzoic acid methyl ester (171 mg, 358 μmol) in methanol (3.58 mL) was treated with potassium carbonate (495 mg, 3.58 mmol). The reaction was heated to 85° C. for 2 h. At this time, the reaction was cooled to 25° C. and diluted with water (50 mL). The solution was extracted with methylene chloride (1×75 mL). The organics were dried over anhydrous sodium sulfate, filtered and concentrated in vacuo to afford 3-(2-methoxy-4-methoxycarbonyl-benzyl)-4-oxo-1-phenyl-1,4-dihydro-[1,8] naphthyridine-2-carboxylic acid methyl ester as a yellow solid (162.7 mg). The water layer was then acidified with a 1N aqueous hydrochloride acid solution and then was extracted into a solution of 10% methanol/methylene chloride (3×75 mL). These organics were dried over anhydrous sodium sulfate, filtered, and concentrated in vacuo to afford crude 3-(4-carboxy-2-methoxy-benzyl)-4-oxo-1-phenyl-1,4-dihydro-[1,8]naphthyridine-2-carboxylic acid methyl ester yellow solid (88.1 mg, 55.4%). This material was used without further purification.

A solution of 3-(4-carboxy-2-methoxy-benzyl)-4-oxo-1-phenyl-1,4-dihydro-[1,8]naphthyridine-2-carboxylic acid methyl ester (27.6 mg, 62.1 μmol), (1S,3R,4S,5S,7S)-4-amino-adamantan-1-ol hydrochloride (see WO2007/107470 A2, 10.4 mg, 62.1 μmol), 1-[3-dimethylamino]propyl]-3-ethylcarbodiimide hydrochloride (19.0 mg, 99.4 μmol), and 1-hydroxybenzotriazole (13.4 mg, 99.4 μmol) in methylene chloride (0.62 mL) was treated with N,N-diisopropylethylamine (80.3 mg, 108 μL, 621 μmol). The reaction was stirred at 25° C. for 18 h. At this time, the reaction was diluted with methylene chloride (50 mL) and was washed with a saturated aqueous ammonium chloride solution (1×100 mL) and a saturated sodium bicarbonate solution (1×100 mL), dried over sodium sulfate, filtered and concentrated in vacuo. Flash chromatography (12 g, 1-10% methanol/methylene chloride) afforded 3-[4-((1S,2S,3R,5S,7S)-5-hydroxy-adamantan-2-ylcarbamoyl)-2-methoxy-benzyl]-4-oxo-1-phenyl-1,4-dihydro-[1,8]naphthyridine-2-carboxylic acid methyl ester as a light yellow solid (15.5 mg, 42%). ES+-HRMS m/e calcd for $C_{35}H_{35}N_3O_6$ [M+H+] 594.2599. Found 594.2591. $^1$H NMR (500 MHz, DMSO-$d_6$) δ ppm 8.69 (dd, J=4.5, 1.7 Hz, 1H) 8.57 (dd, J=7.8, 1.7 Hz, 1H) 7.77 (d, J=6.5 Hz, 1H) 7.48-7.57 (m, 5H) 7.43-7.48 (m, 2H) 7.29 (d, J=1.2 Hz, 1H) 7.27 (dd, J=8.0, 1.2 Hz, 1H) 7.09 (d, J=8.0 Hz, 1H) 4.41 (s, 1H) 3.87 (s, 3H) 3.82-3.95 (m, 1H) 3.78 (s, 2H) 3.35 (s, 3H) 2.09 (br. s., 2H) 1.92-2.02 (m, 3H) 1.68-1.75 (m, 2H) 1.57-1.66 (m, 4H) 1.33 (d, J=12.6 Hz, 2H).

Example 24 rel-3-[2-Fluoro-4-((1S,2S,3R,5S,7S)-5-hydroxy-adamantan-2-ylcarbamoyl)-benzyl]-4-oxo-1-phenyl-1,4-dihydro-[1,8]naphthyridine-2-carboxylic acid methyl ester

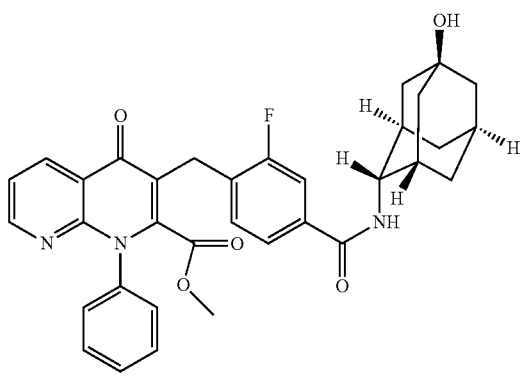 [SMILES: COC(=O)c1c(Cc2ccc(C(=O)N[C@@H]3[C@@H]4C[C@@H]5C[C@H]3C[C@@](O)(C5)C4)cc2F)c(=O)c2cccnc2n1-c1ccccc1]

A solution of 3-fluoro-4-methyl-benzoic acid (2.5 g, 16.2 mmol) in acetone (27.0 mL) was treated with potassium carbonate (5.83 g, 42.2 mmol) and dimethyl sulfate (6.14 g, 4.6 mL, 48.7 mmol). The reaction was stirred at 25° C. for 24 h and then was heated to 90° C. for 8 h. At this time, the reaction was cooled to 25° C. and was stirred at 25° C. for 6 days. At this time, the reaction was filtered through a sintered glass funnel. The potassium carbonate cake was washed thoroughly with acetone. The filtrate was concentrated in vacuo. The residue was then taken up in ethyl acetate (30 mL) and triethylamine (7 mL) and stirred at 25° C. for 30 min. The solution was then transferred to a separatory funnel and washed with water (1×75 mL), a 2N aqueous hydrochloric acid solution (1×75 mL), and a saturated aqueous sodium chloride solution (1×75 mL), dried over sodium sulfate, filtered and concentrated in vacuo to afford 3-fluoro-4-methyl-benzoic acid methyl ester (2.26 g, 82.9%) as a light yellow oil. ES$^+$-HRMS m/e calcd for $C_9H_9O_2F$ [M+H$^+$] 169.0660. Found 169.0659. $^1$H NMR (300 MHz, DMSO-d$_6$) δ ppm 7.70 (dd, J=7.8, 1.5 Hz, 1H) 7.62 (dd, J=10.3, 1.5 Hz, 1H) 7.46 (t, J=7.8 Hz, 1H) 3.85 (s, 3H) 2.31 (d, J=1.5 Hz, 3H).

A solution of 3-fluoro-4-methyl-benzoic acid methyl ester (2.26 g, 13.4 mmol) in carbon tetrachloride (168 mL) was treated with N-bromosuccinimide (6.7 g, 37.6 mmol) and 2,2'-azobis(2-methylpropionitrile) (110 mg, 99.4 μL, 672 μmol). The reaction was heated to reflux at 100° C. for 20 h. At this time, the reaction was cooled to 25° C. and then concentrated in vacuo. The residue was dissolved in ethyl acetate (100 mL) and was then washed with water (1×150 mL), a saturated aqueous sodium bisulfite solution (1×150 mL) and a saturated sodium chloride solution (1×150 mL). The organics were dried over sodium sulfate, filtered and concentrated in vacuo. The residue was dissolved in acetone (80 mL) and water (18 mL) (0.14M, 5:1) and was treated with silver nitrate (6.39 g, 37.6 mmol). The flask was covered with tin foil and the hood light was turned off. The reaction was stirred under these conditions for 24 h. At this time, the reaction was filtered through a coarse sintered glass funnel.

The filtrate was concentrated in vacuo. The resulting solution was transferred to a separatory funnel, diluted with methylene chloride (100 mL) and treated with a saturated aqueous sodium bicarbonate solution (1×100 mL). Upon addition of the saturated aqueous sodium bicarbonate solution, a white precipitate resulted. This precipitate was removed by filtration through a coarse sintered glass funnel and was washed with methylene chloride (20 mL). The filtrate was transferred to another separatory funnel and washed with water (1×100 mL) and a saturated aqueous sodium chloride solution (1×100 mL), dried over sodium sulfate, filtered and concentrated in vacuo. Flash chromatography (40 g, 5-15% ethyl acetate/hexanes) afforded a ~1:1 mixture of 3-fluoro-4-formyl-benzoic acid methyl ester and 4-bromomethyl-3-fluoro-benzoic acid methyl ester (1.56 g) as colorless oil. The material was used without further purification.

A mixture of 1-(2-phenylamino-pyridin-3-yl)-ethanone (700 mg, 3.3 mmol) in methanol (16.5 mL) at 25° C. was treated with 3-fluoro-4-formyl-benzoic acid methyl ester (601 mg, 3.3 mmol, calculated from 50% mixture) and sodium methoxide in methanol (4.37M, 1.51 mL, 6.6 mmol). The reaction was stirred at 25° C. for 48 h. At this time, the reaction was diluted with water (50 mL), neutralized with a 2N aqueous hydrochloric acid solution, and extracted with methylene chloride (3×75 mL). The combined organics were dried over sodium sulfate and filtered. Silica gel was added to the filtrate, concentrated in vacuo and dried under high vacuum. Flash Chromatography (40 g silica column, 1% methanol/methylene chloride) afforded 3-fluoro-4-[(E)-3-oxo-3-(2-phenylamino-pyridin-3-yl)-propenyl]-benzoic acid methyl ester (1 g, 80.6%) as a red solid.

A solution of 3-fluoro-4-[(E)-3-oxo-3-(2-phenylamino-pyridin-3-yl)-propenyl]-benzoic acid methyl ester (890 mg, 2.36 mmol) in methanol (59.1 mL) and ethyl acetate (59.1 mL) at 25° C. was treated with platinum(IV) oxide (26.8 mg, 118 μmol). The reaction was stirred under a balloon of hydrogen gas for 18 h. At this time, the reaction was filtered through a pad of Celite® and was rinsed with a solution of 10% methanol/methylene chloride (3×75 mL). The filtrate was concentrated in vacuo to afford 3-fluoro-4-[3-oxo-3-(2-phenylamino-pyridin-3-yl)-propyl]-benzoic acid methyl ester (860 mg, 96.2%) as a dark green solid. The material was used without further purification.

A solution of 3-fluoro-4-[3-oxo-3-(2-phenylamino-pyridin-3-yl)-propyl]-benzoic acid methyl ester (860.8 mg, 2.27 mmol) in toluene (45.5 mL) was treated with methyl oxalyl chloride (1.39 g, 1.05 mL, 11.4 mmol). The reaction was heated to 130° C. for 5 h. At this time, the reaction was cooled to 25° C. and concentrated in vacuo to afford 3-fluoro-4-{3-[2-(methoxyoxalyl-phenyl-amino)-pyridin-3-yl]-3-oxo-propyl}-benzoic acid methyl ester. The residue was used without further purification.

A solution of 3-fluoro-4-{3-[2-(methoxyoxalyl-phenyl-amino)-pyridin-3-yl]-3-oxo-propyl}-benzoic acid methyl ester (1.05 g, 2.27 mmol) in methanol (22.7 mL) was treated with potassium carbonate (3.14 g, 22.7 mmol). The reaction was heated to 85° C. for 3 h. At this time, the reaction was cooled to 25° C. and diluted with water (100 mL). The solution was extracted with methylene chloride (2×100 mL). The aqueous layer was then acidified with a 3N aqueous hydrochloride acid solution and then was extracted into a solution of 10% methanol/methylene chloride (3×75 mL). These organics were dried over anhydrous sodium sulfate, filtered, and concentrated in vacuo to afford crude 3-(4-carboxy-2-fluoro-benzyl)-4-oxo-1-phenyl-1,4-dihydro-[1,8]naphthyridine-2-carboxylic acid methyl ester as a light yellow solid (520 mg, 53%). This material was used without further purification.

A solution of 3-(4-carboxy-2-fluoro-benzyl)-4-oxo-1-phenyl-1,4-dihydro-[1,8]naphthyridine-2-carboxylic acid methyl ester (150 mg, 347 µmol), (1S,3R,4S,5S,7S)-4-amino-adamantan-1-ol hydrochloride (see WO2007/107470 A2, 70.7 mg, 347 µmol), 1-[3-dimethylamino]propyl]-3-ethylcarbodiimide hydrochloride (107 mg, 555 µmol), and 1-hydroxybenzotriazole (76.5 mg, 555 µmol) in methylene chloride (3.47 mL) was treated with N,N-diisopropylethylamine (453 mg, 612 µL, 3.47 mmol). The reaction was stirred at 25° C. for 2 d. At this time, the reaction was diluted with methylene chloride (50 mL) and was washed with a saturated aqueous ammonium chloride solution (1×100 mL) and a saturated sodium bicarbonate solution (1×100 mL), dried over sodium sulfate, filtered and concentrated in vacuo. Flash chromatography (24 g, 1-10% methanol/methylene chloride) afforded 3-[2-fluoro-4-((1S,2S,3R,5S,7S)-5-hydroxy-adamantan-2-ylcarbamoyl)-benzyl]-4-oxo-1-phenyl-1,4-dihydro-[1,8]naphthyridine-2-carboxylic acid methyl ester as an off-white solid (113.7 mg, 56.4%). ES$^+$-HRMS m/e calcd for $C_{34}H_{32}FN_3O_5$ [M+H$^+$] 582.2399. Found 582.2387. $^1$H NMR (500 MHz, DMSO-$d_6$) δ ppm 8.69 (dd, J=4.5, 2.0 Hz, 1H) 8.58 (dd, J=8.1, 2.0 Hz, 1H) 7.88 (d, J=6.5 Hz, 1H) 7.60 (dd, J=10.6, 1.5 Hz, 1H) 7.50-7.57 (m, 5H) 7.44-7.49 (m, 2H) 7.31 (t, J=7.8 Hz, 1H) 4.41 (s, 1H) 3.87-3.96 (m, 1H) 3.86 (s, 2H) 3.39 (s, 3H) 2.07 (br. s., 2H) 1.97 (d, J=16.1 Hz, 3H) 1.66-1.78 (m, 2H) 1.55-1.66 (m, 4H) 1.32 (d, J=12.1 Hz, 2H).

Example 25 rel-3-[4-((1S,2S,3R,5S,7S)-5-Hydroxy-adamantan-2-ylcarbamoyl)-benzyl]-4-oxo-1-phenyl-7-trifluoromethyl-1,4-dihydro-[1,8]naphthyridine-2-carboxylic acid methyl ester

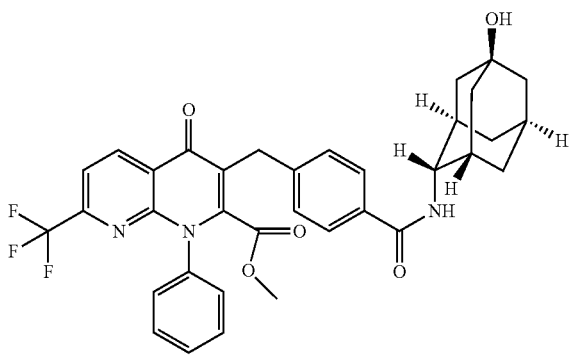 [SMILES: COC(=O)c1c(Cc2ccc(C(=O)N[C@@H]3[C@@H]4C[C@@H]5C[C@H]3C[C@@](O)(C5)C4)cc2)c(=O)c2ccc(C(F)(F)F)nc2n1-c1ccccc1]

A solution of 2-chloro-6-trifluoromethyl-nicotinic acid (5 g, 22.2 mmol) in tetrahydrofuran (20 mL) cooled to −78° C. was treated with lithium bis(trimethylsilyl)amide (1.0 M solution in tetrahydrofuran, 66.5 mL, 66.5 mmol). This solution was stirred at −78° C. for 2 h. At this time, the reaction was treated with a solution of aniline (19.6 g, 19.2 mL, 210 mmol) in tetrahydrofuran (20 mL). The reaction was allowed to gradually warm to 25° C. and was stirred at 25° C. overnight. At this time, the reaction mixture was diluted with ethyl acetate (250 mL), washed with a saturated aqueous sodium bicarbonate solution (2×150 mL), water (1×50 mL), and a saturated sodium chloride solution (1×50 mL). The organic layers were dried over anhydrous magnesium sulfate, filtered and concentrated in vacuo. The residue was triturated in ether to afford 2-phenylamino-6-trifluoromethyl-nicotinic acid (6.19 g, 96.9%) as a light brown solid.

A solution of 2-phenylamino-6-trifluoromethyl-nicotinic acid (6.2 g, 22.0 mmol), N,O-dimethylhydroxylamine hydrochloride (2.79 g, 28.6 mmol) and 2-(1H-benzotriazol-1-yl)-1,1,3,3-tetramethyluronium hexafluorophosphate (13.3 g, 35.2 mmol) in N,N-dimethylformamide (120 mL) was treated with N,N-diisopropylethylamine (8.88 g, 12 mL, 68.7 mmol). The reaction mixture was stirred at 25° C. for 4 h. At this time, the reaction was diluted with methylene chloride (400 mL), washed with a saturated aqueous ammonium chloride solution (1×300 mL), a saturated aqueous sodium bicarbonate solution (1×300 mL), and a saturated aqueous sodium chloride solution (1×200 mL), dried over anhydrous sodium sulfate, filtered and concentrated in vacuo. Flash chromatography (250 g silica column, 10-35% ethyl acetate/hexanes) afforded N-methoxy-N-methyl-2-phenylamino-6-trifluoromethyl-nicotinamide (6.86 g, 96%) as a brown oil which upon trituration with ether became a brown solid.

A solution of N-methoxy-N-methyl-2-phenylamino-6-trifluoromethyl-nicotinamide (5.10 g, 15.7 mmol) in tetrahydrofuran (100 mL) cooled to 0° C. was treated with a solution of 3 M methylmagnesium chloride (15.7 mL, 47.0 mmol). The reaction was then stirred at 0° C. for 90 min. At this time, the reaction was warmed to 25° C. and was quenched with water (150 mL). The reaction was then partitioned between ethyl acetate (250 mL) and water (250 mL). The aqueous layer was back extracted with ethyl acetate (2×150 mL). The combined organics were washed with a saturated aqueous sodium chloride solution (50 mL), filtered, rinsed with ethyl acetate and concentrated in vacuo. Flash chromatography (20%-40% ethyl acetate/hexanes) afforded 1-(2-phenylamino-6-trifluoromethyl-pyridin-3-yl)-ethanone (4.28 g, 97.4%) as a yellow solid.

A mixture of 1-(2-phenylamino-6-trifluoromethyl-pyridin-3-yl)-ethanone (4.28 g, 15.3 mmol) in methanol (60.4 mL) at 25° C. was treated with methyl 4-formylbenzoate (3.01 g, 18.3 mmol) and sodium methoxide in methanol (25% wt, 6.99 mL, 30.5 mmol). The reaction was stirred at 25° C. for 2 d. At this time, the reaction was diluted with water (50 mL), neutralized with a 2N aqueous hydrochloric acid solution, and extracted with methylene chloride (3×75 mL). The combined organics were dried over sodium sulfate and filtered. Silica gel was added to the filtrate, concentrated in vacuo and dried under high vacuum. Flash chromatography (40 g silica column, 10-100% ethyl acetate/hexanes) afforded 4-[(E)-3-oxo-3-(2-phenylamino-6-trifluoromethyl-pyridin-3-yl)-propenyl]-benzoic acid methyl ester (4.04 g, 62%) as an orange solid.

A solution of 4-[(E)-3-oxo-3-(2-phenylamino-6-trifluoromethyl-pyridin-3-yl)-propenyl]-benzoic acid methyl ester (4.02 g, 9.43 mmol) in acetone (150 mL) at 25° C. was treated with 10% palladium on activated carbon (402 mg, 3.78 µmol). The reaction was stirred under a balloon of hydrogen gas for 18 h. At this time, the reaction was filtered through a pad of Celite® and was rinsed with a solution of 10% methanol/methylene chloride (3×75 mL). The filtrate was concentrated in vacuo to afford 4-[3-oxo-3-(2-phenylamino-6-trifluoromethyl-pyridin-3-yl)-propyl]-benzoic acid methyl ester (2.64 g, 65.4%) as a yellow solid. The material was used without further purification.

A solution of 4-[3-oxo-3-(2-phenylamino-6-trifluoromethyl-pyridin-3-yl)-propyl]-benzoic acid methyl ester (101 mg, 236 µmol) in toluene (4.72 mL) was treated with methyl oxalyl chloride (289 mg, 218 µL, 2.36 mmol). The reaction was heated to 130° C. for 2 d. At this time, the reaction was cooled to 25° C. and concentrated in vacuo to afford 4-{3-[2-(methoxyoxalyl-phenyl-amino)-6-trifluoromethyl-pyridin-3-yl]-3-oxo-propyl}-benzoic acid methyl ester (121 mg). The residue was used without further purification.

A solution of 4-{3-[2-(methoxyoxalyl-phenyl-amino)-6-trifluoromethyl-pyridin-3-yl]-3-oxo-propyl}-benzoic acid methyl ester (121 mg, 236 µmol) in methanol (2.36 mL) was treated with potassium carbonate (326 mg, 2.36 mmol). The reaction was heated to 85° C. for 2 h. At this time, the reaction was cooled to 25° C. and diluted with water (50 mL). The solution was extracted with methylene chloride (1×30 mL). The aqueous layer was then neutralized with a 1N aqueous hydrochloric acid solution and then was extracted into a solution of 10% methanol/methylene chloride (3×50 mL). The organics were dried over anhydrous sodium sulfate, filtered, and concentrated in vacuo to afford crude 3-(4-carboxy-benzyl)-4-oxo-1-phenyl-7-trifluoromethyl-1,4-dihydro-[1,8] naphthyridine-2-carboxylic acid methyl ester as a yellow solid (20 mg, 17.6%). This material was used without further purification.

A solution of 3-(4-carboxy-benzyl)-4-oxo-1-phenyl-7-trifluoromethyl-1,4-dihydro-[1,8]naphthyridine-2-carboxylic acid methyl ester (51.2 mg, 106 μmol), (1S,3R,4S,5S,7S)-4-amino-adamantan-1-ol hydrochloride (see WO2007/107470 A2, 19.5 mg, 95.7 μmol) and bis(2-oxo-3-oxazolidinyl)phosphinic chloride (40.5 mg, 159 μmol) in N,N-dimethylformamide (531 μL) was treated with N,N-diisopropylethylamine (41.2 mg, 55.5 μL, 318 μmol). The reaction was stirred at 25° C. for 2 d. At this time, the reaction was diluted with methylene chloride (50 mL) and was washed with a saturated aqueous ammonium chloride solution (1×50 mL) and a saturated sodium bicarbonate solution (1×50 mL), dried over sodium sulfate, filtered and concentrated in vacuo. Flash chromatography (12 g, 20-100% ethyl acetate/hexanes) afforded 3-[4-((1S,2S,3R,5S,7S)-5-hydroxy-adamantan-2-ylcarbamoyl)-benzyl]-4-oxo-1-phenyl-7-trifluoromethyl-1,4-dihydro-[1,8]naphthyridine-2-carboxylic acid methyl ester (11.3 mg, 16.9%) as light yellow solid. ES$^+$-HRMS m/e calcd for $C_{35}H_{32}F_3N_3O_5$ [M+H$^+$] 632.2367. Found 632.2366. $^1$H NMR (300 MHz, DMSO-d$_6$) δ ppm 8.82 (d, J=7.8 Hz, 1H), 7.93 (d, J=8.2 Hz, 1H), 7.80 (d, J=6.6 Hz, 1H), 7.69 (d, J=8.5 Hz, 2H), 7.52-7.60 (m, 3H), 7.44-7.53 (m, 2H), 7.34 (d, J=8.5 Hz, 2H), 4.42 (s, 1H), 3.90 (br. s., 1H), 3.86 (s, 2H), 3.45 (s, 3H), 1.91-2.12 (m, 4H), 1.54-1.77 (m, 6H), 1.20-1.39 (m, 3H).

Example 26 rel-7-Chloro-3-[4-((1S,2S,3R,5S,7S)-5-hydroxy-adamantan-2-ylcarbamoyl)-2-oxo-2H-pyridin-1-ylmethyl]-4-oxo-1-phenyl-1,4-dihydro-quinoline-2-carboxylic acid methyl ester

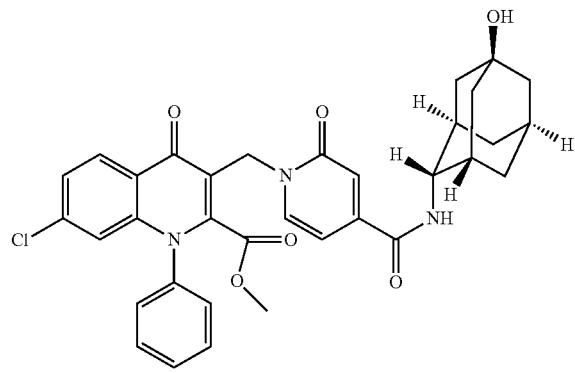 [SMILES: COC(=O)c1c(Cn2ccc(C(=O)N[C@@H]3[C@@H]4C[C@@H]5C[C@H]3C[C@@](O)(C5)C4)cc2=O)c(=O)c2ccc(Cl)cc2n1-c1ccccc1]

A solution of 2-bromo-4-chlorobenzoic acid (25.0 g, 106.0 mmol) in 2-ethoxy ethanol (40 mL) was treated with copper powder (0.74 g, 11.6 mmol), copper (I) oxide (0.76 g, 5.3 mmol) and potassium carbonate (15.8 g, 114.0 mmol) at 25° C. under nitrogen. The reaction was stirred at 25° C. for 5 min. At this time, the reaction was treated with aniline (11.2 mL, 124 mmol) and then was heated 135° C. for 48 h. At this time, the reaction was cooled to 25° C., diluted with water (30 mL) and was acidified with a 1N aqueous hydrochloric acid solution. The resulting mixture was stirred at 25° C. overnight. At this time, the resulting precipitate was collected by filtration through a sintered glass funnel. The solids were washed with an excess amount of water (2×100 mL) and then were dried under high vacuum to afford 4-chloro-2-phenylamino-benzoic acid (19 g, 72.3%) as a brown solid. This material was used without further purification.

A solution of 4-chloro-2-phenylamino-benzoic acid (10.1 g, 41.0 mmol) in N,N-dimethylformamide (200 mL) at 25° C. was treated with O-benzotriazole-N,N,N',N'-tetramethyl-uronium-hexafluoro-phosphate (31.2 g, 82.0 mmol), N,O-dimethyl hydroxylamine hydrochloride (7.94 g, 82.0 mmol), and N,N-diisopropylethylamine (45.0 g, 350 mmol). The resulting mixture was stirred at 25° C. for 24 h. At this time, the reaction mixture was diluted with ethyl acetate (600 mL) and washed with water (4×200 mL) and a saturated aqueous sodium chloride solution (1×200 mL). The organics were dried over anhydrous sodium sulfate, filtered and concentrated in vacuo. Flash chromatography (silica gel, 100-200 mesh, ethyl acetate/hexanes 10-25%) afforded 4-chloro-N-methoxy-N-methyl-2-phenylamino-benzamide (6.62 g, 56.4%) as a yellow solid. $^1$H NMR (DMSO-d$_6$) δ ppm 7.93 (s, 1H), 7.20-7.39 (m, 3H), 7.02-7.17 (m, 3H), 6.88-6.99 (m, 2H), 3.50 (s, 3H), 3.20 (s, 3H); MS m/e calcd for $C_{15}H_{15}ClN_2O_2$ [(M+H)$^+$] 291.0. Found 291.0; [(M−$C_2H_6NO$)$^+$] 230.0. Found 230.0.

A solution of 4-chloro-N-methoxy-N-methyl-2-phenylamino-benzamide (5.0 g, 17.2 mmol) in tetrahydrofuran (60 mL) was treated dropwise with ethylmagnesium bromide (1M solution in tetrahydrofuran, 70 mL, 70 mmol). Upon completion of addition, the mixture was allowed to slowly warm to 25° C. where it was stirred for 2 h. At this time, the reaction was cooled to 0° C., was quenched with a 1N aqueous hydrochloric acid solution (50 mL) and was then extracted with ethyl acetate (2×300 mL). The combined organics were washed with water (100 mL) and a saturated aqueous sodium chloride solution (100 mL), dried over anhydrous sodium sulfate, filtered and concentrated in vacuo. Flash chromatography (silica gel; 100-200 mesh, ethyl acetate/hexanes 10-25%) afforded 1-(4-chloro-2-phenylamino-phenyl)-propan-1-one (4.15 g, 92.9%) as a yellow oil. $^1$H NMR (DMSO-d$_6$) δ ppm 10.53 (s, 1H), 8.00 (d, J=8.7 Hz, 1H), 7.34-7.51 (m, 2H), 7.28 (d, J=7.7 Hz, 2H), 7.13-7.23 (m, 1H), 7.07 (d, J=1.8 Hz, 1H), 6.82 (dd, J=8.6, 1.9 Hz, 1H), 3.07 (q, J=7.2 Hz, 2H), 1.09 (t, J=7.3 Hz, 3H).

A solution of 1-(4-chloro-2-phenylamino-phenyl)-propan-1-one (13.0 g, 50.2 mmol) in toluene (150 mL) at 25° C. was treated with methyl chlorooxoacetate (42.86 g, 350 mmol). The reaction mixture was then heated at 110° C. for 16 h. At this time, the reaction mixture was concentrated in vacuo to afford N-(5-chloro-2-propionyl-phenyl)-N-phenyl-oxalamic acid methyl ester (15.2 g, 87.6%). The material was used without further purification.

A stirred suspension of N-(5-chloro-2-propionyl-phenyl)-N-phenyl-oxalamic acid methyl ester (15.0 g, 43.5 mmol) in methanol (200 mL) was treated with potassium carbonate (35.0 g, 253 mmol) at 25° C. The mixture was then heated at 80° C. for 1 h. At this time, the reaction was cooled to 25° C. The resulting solids were collected by filtration through a sintered glass funnel and then washed with methanol (2×50 mL). The filtrate was concentrated in vacuo. The resulting residue was dissolved in ethyl acetate (500 mL) and was washed with water (2×200 mL). The organics were dried over sodium sulfate, filtered and concentrated in vacuo. The resulting solids were triturated with hexanes and diethyl ether to afford 7-chloro-3-methyl-4-oxo-1-phenyl-1,4-dihydro-quinoline-2-carboxylic acid methyl ester (10.5 g, 73.4%). $^1$H NMR (DMSO-$d_6$) δ ppm 8.24 (d, J=8.7 Hz, 1H), 7.28-7.78 (m, 6H), 6.69 (d, J=1.7 Hz, 1H), 3.49 (s, 3H), 1.97 (s, 3H); MS m/e calcd for $C_{18}H_{14}ClNO_3$ [(M+H)$^+$] 328.0. Found 327.9.

A solution of 7-chloro-3-methyl-4-oxo-1-phenyl-1,4-dihydro-quinoline-2-carboxylic acid methyl ester (1.6 g, 4.88 mmol), N-bromosuccinimide (869 mg, 4.88 mmol) and benzoyl peroxide (118 mg, 488 μmol) in carbon tetrachloride (50 mL) was heated at 100° C. for 5 h. At this time, the reaction was cooled to 25° C. The resulting solids were collected by filtration to afford 3-bromomethyl-7-chloro-4-oxo-1-phenyl-1,4-dihydro-quinoline-2-carboxylic acid methyl ester (1.7 g, 85.6%) as a white solid. The material was used without further purification.

A solution of 3-bromomethyl-7-chloro-4-oxo-1-phenyl-1,4-dihydro-quinoline-2-carboxylic acid methyl ester (550 mg, 1.35 mmol), methyl-2-hydroxyisonicotinate (290 mg, 1.89 mmol) and potassium carbonate (280 mg, 2.03 mmol) in N,N-dimethylformamide (15 mL) was stirred at 25° C. overnight. At this time, the reaction was concentrated in vacuo. Flash chromatography (ISCO column, 40% ethyl acetate/hexanes) afforded 7-chloro-3-(4-methoxycarbonyl-2-oxo-2H-pyridin-1-ylmethyl)-4-oxo-1-phenyl-1,4-dihydro-quinoline-2-carboxylic acid methyl ester (300 mg, 46%) as a white solid. MS m/e calcd for $C_{25}H_{19}ClN_2O_6$ [(M+H)$^+$] 479.0. Found 479.0.

A solution of 7-chloro-3-(4-methoxycarbonyl-2-oxo-2H-pyridin-1-ylmethyl)-4-oxo-1-phenyl-1,4-dihydro-quinoline-2-carboxylic acid methyl ester (0.22 g, 459 μmol) in tetrahydrofuran (10 mL) at 25° C. was treated with a 1N aqueous sodium hydroxide solution (0.7 mL, 459 μmol). The reaction was stirred at 25° C. for 2 h. At this time, the reaction was acidified with a 1N aqueous hydrochloric acid solution and then concentrated in vacuo to afford 3-(4-carboxy-2-oxo-2H-pyridin-1-ylmethyl)-7-chloro-4-oxo-1-phenyl-1,4-dihydro-quinoline-2-carboxylic acid methyl ester. The material was used without further purification.

A solution of 3-(4-carboxy-2-oxo-2H-pyridin-1-ylmethyl)-7-chloro-4-oxo-1-phenyl-1,4-dihydro-quinoline-2-carboxylic acid methyl ester (80 mg, 172 μmol), (1S,3R,4S,5S,7S)-4-amino-adamantan-1-ol hydrochloride (see WO2007/107470 A2, 34.8 mg, 172 μmol) and bromo-tris-pyrrolidino phosphoniumhexafluorophosphate (120 mg, 258 μmol) in methylene chloride (10 mL) at 25° C. was treated with N,N-diisopropylethylamine (120 μL, 688 μmol). The reaction was stirred at 25° C. for 24 h. At this time, the reaction was concentrated in vacuo. Flash chromatography (12 g, 40-100% ethyl acetate/hexanes) afforded 7-chloro-3-[4-((1S,2S,3R,5S,7S)-5-hydroxy-adamantan-2-ylcarbamoyl)-2-oxo-2H-pyridin-1-ylmethyl]-4-oxo-1-phenyl-1,4-dihydro-quinoline-2-carboxylic acid methyl ester (32 mg, 30%) as a light brown solid. $^1$H NMR (400 MHz, DMSO-$d_6$) δ ppm 1.30 (d, J=12.55 Hz, 2H) 1.52-1.75 (m, 6H) 1.85-2.11 (m, 5H) 2.53 (s, 2H) 3.43 (s, 3H) 3.86 (br. s., 1H) 4.41 (s, 1H) 5.00 (s, 2H) 6.41 (dd, J=7.15, 1.88 Hz, 1H) 6.73 (dd, J=12.17, 1.88 Hz, 2H) 7.45-7.62 (m, 3H) 7.63-7.72 (m, 3H) 7.86 (d, J=7.28 Hz, 1H) 8.08 (d, J=6.53 Hz, 1H) 8.26 (d, J=8.78 Hz, 1H); MS m/e calcd for $C_{34}H_{32}ClN_3O_6$ [(M+)$^+$] 614.0. Found 614.0.

Example 27

Rel-4-(7-Chloro-2-oxazol-2-yl-4-oxo-1-phenyl-1,4-dihydro-quinolin-3-ylmethyl)-N-((1S,2S,3R,5S,7S)-5-hydroxy-adamantan-2-yl)-benzamide

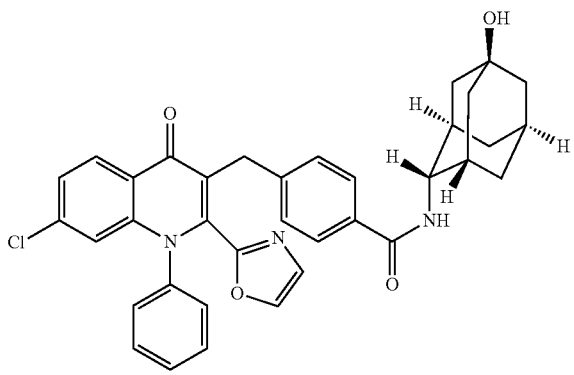 [SMILES: O=C(N[C@@H]1[C@@H]2C[C@@H]3C[C@H]1C[C@@](O)(C3)C2)c1ccc(Cc2c(-c3ncco3)n(-c3ccccc3)c3cc(Cl)ccc3c2=O)cc1]

In a 250 mL round-bottomed flask, oxazole-2-carboxylic acid (obtained from Princeton Biomolecular Research, 0.30 g, 2.6 mmol) and N,N-dimethylformamide (50 μL) were combined with $CH_2Cl_2$ (6 mL) to give a white suspension. Oxalyl chloride (0.8 mL, 9.3 mmol) was added dropwise, then the reaction mixture was stirred at room temperature for 1 hr. After this time, the reaction mixture was a slightly yellow, homogeneous mixture. The reaction mixture was concentrated on the rotary evaporator, then the crude oxazole-2-carbonyl chloride was used immediately in the next step without further purification.

Separately, in a 100 mL round-bottomed flask, methyl 4-(3-(4-chloro-2-(phenylamino)phenyl)-3-oxopropyl)benzoate (898 mg, 2.28 mmol) was combined with THF to give a yellow solution. A 1.0 M solution of NaHMDS in THF (5.7 ml, 5.7 mmol) was added. The reaction mixture was stirred at room temperature for 15 minutes. A heterogeneous mixture of oxazole-2-carbonyl chloride from above, THF (5 mL), DMF (500 μL) was added dropwise to the reaction mixture. The mixture was stirred at room temperature overnight. The reaction flask was cooled to 0° C., then the reaction was quenched with water. The resulting heterogeneous mixture was extracted with ethyl acetate, and the organic phase was dried over $MgSO_4$, filtered, then concentrated. The crude product was dissolved in methylene chloride, then concentrated over silica gel. The silica gel supported crude product was loaded onto a 80 gram analogix column. Flash chromatography (15% EtOAc-hexanes→55% EtOAc-hexanes) provided 4-(7-Chloro-2-oxazol-2-yl-4-oxo-1-phenyl-1,4-dihydro-quinolin-3-ylmethyl)-benzoic acid methyl ester (28 mg, 2.6%) as a light yellow solid.

A solution of 4-(7-chloro-2-oxazol-2-yl-4-oxo-1-phenyl-1,4-dihydro-quinolin-3-ylmethyl)-benzoic acid methyl ester (28 mg, 60 μmol) in THF (1 mL) was combined with an aqueous solution of sodium hydroxide (1 mL, 100 μmol). The mixture was stirred at room temperature for 2 hrs. The reaction was quenched with 1 N aqueous HCl then concentrated to a solid. The crude 4-(7-chloro-2-oxazol-2-yl-4-oxo-1-phenyl-1,4-dihydro-quinolin-3-ylmethyl)-benzoic acid was used in the next step without further purification.

In a 20 mL round-bottomed flask, 4-(7-chloro-2-oxazol-2-yl-4-oxo-1-phenyl-1,4-dihydro-quinolin-3-ylmethyl)-benzoic acid (0.027 g, 59 μmol), 1-hydroxybenzotriazole (14.5 mg, 94.6 µmol), 1-[3-dimethylaminopropyl]-3-ethylcarbodiimide hydrochloride (18.1 mg, 94.6 µmol) and N,N-diisopropylethylamine (103 µL, 590 µmol) were combined with $CH_2Cl_2$ (5 mL). The mixture was stirred for 10 minutes, then (1S,3R,4S,5S,7S)-4-amino-adamantan-1-ol hydrochloride (see WO2007/107470 A2, 9.9 mg, 59 µmol) was added. The reaction mixture was stirred at room temperature overnight. The crude mixture was loaded onto an Isco (40 g silica column, 1%-10% methanol/methylene chloride) to afford 4-(7-Chloro-2-oxazol-2-yl-4-oxo-1-phenyl-1,4-dihydro-quinolin-3-ylmethyl)-N-((1S,2S,3R,5S,7S)-5-hydroxy-adamantan-2-yl)-benzamide (10.5 mg, 28%) as a white powder. $^1$H NMR (DMSO-d$_6$) δ: 8.28 (d, J=8.5 Hz, 1H), 8.06 (s, 1H), 7.76 (d, J=6.5 Hz, 1H), 7.63 (d, J=8.0 Hz, 2H), 7.39-7.54 (m, 6H), 7.26 (s, 1H), 7.14 (d, J=8.0 Hz, 2H), 6.71 (d, J=1.8 Hz, 1H), 4.41 (s, 1H), 3.85-3.96 (m, 1H), 3.72 (s, 2H), 2.06 (br. s., 2H), 1.96 (d, J=14.1 Hz, 3H), 1.65-1.75 (m, 2H), 1.54-1.64 (m, 4H), 1.31 (d, J=12.0 Hz, 2H); MS m/e calcd for $C_{36}H_{33}ClN_3O_4$ [(M+H)$^+$] 606.2. Found 606.3

Biological Examples

In vitro JNK1 Assay

Phosphorylation of GST-c-Jun protein (amino acid residues 1-79) was measured as JNK1 activity. The kinase reaction contained 0.2 nM of active JNK1 kinase and 26.7 nM of GST-c-Jun in the presence of 2 µM ATP. The reaction buffer contained 50 mM HEPES, pH 7.0, 10 mM $MgCl_2$, 1 mM DTT, 0.1 mM $Na_3VO_4$ and 0.2 mg/mL BSA. After 30 min. incubation at room temperature, the reaction was terminated by adding buffer containing 8 mM EDTA and a polyclonal anti-phospho-c-Jun antibody (Cell Signaling #9261L), followed by an additional incubation of 30 min. at room temperature. A detection reagent mixture containing 2 nM Europium labeled goat anti-rabbit antibody and 20 nM of Allophycocyanin labeled anti-GST antibody (Columbia Biosciences #D3-1310), was then added. Time-resolved Fluorescence Resonance Energy Transfer (TR-FRET) signals were measured 1 hr. later on the EnVision reader (Perkin Elmer). Compound potency was assessed at 10 serially diluted concentrations. Percentage of inhibition at each concentration was determined to generate an $IC_{50}$ value for each compound.

TABLE II

Representative Compound $IC_{50}$'s for JNK1

| Compound | JNK1, $IC_{50}$ (µM) | HK-2, $EC_{50}$ (µM) |
|---|---|---|
| I-1 | 0.012 | 4.1 |
| I-2 | 0.047 | 8.5 |
| I-3 | 0.012 | 5.8 |
| I-4 | 0.051 | 6.3 |
| I-5 | 0.33 | not tested |
| I-6 | 0.11 | 4.4 |
| I-7 | 0.049 | 22 |
| I-8 | 0.12 | 44 |
| I-9 | 0.027 | 3.2 |
| I-10 | 0.030 | 3.5 |
| I-11 | 0.062 | 6.9 |
| I-12 | 0.017 | 3.3 |
| I-13 | 0.042 | 1.9 |
| I-14 | 0.026 | 3.1 |
| I-15 | 0.057 | 3.2 |
| I-16 | 0.010 | 1.9 |
| I-17 | 0.026 | 3.1 |
| I-18 | 0.005 | 1.8 |
| I-19 | 0.011 | 2.1 |
| I-20 | 0.039 | 5.3 |
| I-21 | 0.025 | 4.8 |
| I-22 | 0.022 | 4.1 |
| I-23 | 0.027 | 7.8 |
| I-24 | 0.034 | 8.6 |
| I-25 | 0.077 | 3.6 |
| I-26 | 0.040 | 3.9 |
| I-27 | 0.027 | 8.6 |
| 7-chloro-3-(4-methanesulfonyl-benzyl)-4-oxo-1-phenyl-1,4-dihydro-quinoline-2-carboxylic acid methyl ester | 0.032 | 15 |

Cell-Based Assay for JNK Inhibitors

The cell-based assay employed the in-cell ELISA method to determine the ability of compounds to prevent the generation of phospho(Ser63)-c-jun in HK-2 cells (human proximal tubule cells) in response to stimulation with tumor necrosis factor α (TNFα). In brief, for quantification of phospho (Ser63)-c-jun, the cells (in 96-well format) were fixed and permeablized then incubated sequentially with a rabbit anti-phospho-c-jun First Antibody specific for the presence of the phospho-Ser63 epitope and a donkey anti-rabbit IgG Second Antibody linked to horseradish peroxidase (HRP) for colorimetric quantitation of binding. For determination of non-specific binding of the First Antibody, Blank wells were pre-incubated with a mouse anti-phospho(Ser63)-c-jun Blocking Antibody that prevented specific binding of the First Antibody to the phospho-Ser63 epitope, but which was not recognized by the donkey anti-rabbit IgG Second Antibody. Thus the remaining signal represented non-specific binding only and this was used as the value for 100% inhibition (Blank value). Blank wells received no TNFα stimulation or compound. Additional Control wells received TNFα stimulation, but no compound. The signal obtained in this case was considered the value for 0% inhibition (Control value).

Stock cultures of HK-2 cells (ATCC, Manassas, Va.) were grown under a 5% CO2/95% O2 atmosphere at 37 degrees C. in Keratinocyte-SFM medium (KSFM, Invitrogen, Grand Island, N.Y.) containing 5 µg/L epidermal growth factor and 5 mg/L bovine pituitary extract (both supplied with the medium), additionally supplemented with 10% (v/v) fetal calf serum (FCS; Invitrogen, Grand Island, N.Y.) and 1% (v/v) antibiotic-antimycotic (ABAM: Sigma, St. Louis, Mo.). For assays, cells were seeded in collagen coated 96-well polystyrene plates (BD Biosciences, Franklin Lakes, N.J.) at a density of 40,000 cells/well and cultured for 24 h in the same medium (100 µL/well) followed by a further 16-24 h in 100 µL of similar medium, but without FCS. The medium was then replaced by 100 µL/well of Assay Medium (KSFM supplemented only with ABAM as above and 0.2% (w/v) low-endotoxin bovine serum albumin (BSA, Sigma, St. Louis, Mo.). Stock solutions of test compounds in dimethylsulfoxide (DMSO) were diluted into Assay Medium to the desired concentrations such that the final DMSO concentration was 1% (v/v) in all cases. For determination of $EC_{50}$s, six concentrations of compound were used (4-fold dilutions). Assay Medium for Blank and Control wells was made 1% with respect to DMSO, but without compound. To initiate the assay, the medium was replaced with the Assay Medium containing compound and culture was continued for 60 minutes after which time 5 µL of a solution of TNFα (Sigma, St. Louis, Mo.) in phosphate buffered saline (PBS; Invitrogen, Grand Island, N.Y.) was added to give a final concentration of 10 ng/mL TNFα (except Blank and PBS Control wells that received PBS alone). Cells were incubated for a further 30 minutes and then the medium was aspirated and the wells washed with 100 μL/well PBS followed by the addition of 100 μL 3.7% (v/v) Formaldehyde (Fisher Scientific, Fair Lawn, N.J.) in PBS. Plates were then allowed to stand at room temperature for 20 minutes before being washed with 200 μL/well of PBS. (Further steps were performed immediately or the plates were stored at 4 degrees C. and the assay completed the next day.) To each well was added 100 μL 1% (v/v) TritonX-100 (Sigma, St. Louis, Mo.) in PBS followed by 20 minutes standing at room temperature, washing with 200 μL/well PBS, the addition of 100 μL/well of Quenching buffer (1% (v/v) hydrogen peroxide (Sigma, St. Louis, Mo.) and 0.1% (w/v) sodium azide (Fisher Scientific, Fair Lawn, N.J.)) in PBS and a further 20 minutes at room temperature. Plates were then washed twice with 200 μL/well of 0.1% (v/v) Tween-20 (Teknova, Hollister, Calif.) in PBS before addition of 200 μL/well of 2% BSA/0.10% Tween-20 in PBS and a further 1 hour at room temperature. At this time, buffer was removed from Blank wells and replaced with 90 μL/well of mouse anti-phospho-c-jun-Ser63 (BD Bioscience, 558036) diluted 1:4000 in PBS containing 1% BSA/0.1% Tween-20 (Antibody Dilution Buffer). All other wells are replaced with 90 μL/well of rabbit anti-phospho-c-jun-Ser63 (Cell Signaling, 9261) diluted 1:250 in Antibody Dilution Buffer. After a further one hour, rabbit anti-phospho-c-jun-Ser63 is added directly to the solution in the Blank wells resulting in 1:250 dilution of this antibody. Plates were then placed on a slowly rotating platform at 4 degrees C. overnight. Wells were then washed thrice with 200 μL/well PBS/0.1% Tween-20. After addition of the third wash, the plates were placed on a slowly rotating platform for 15 minutes at room temperature. The final PBS/Tween20 wash was then replaced with 100 μL/well of donkey anti-rabbit HRP-labeled Second Antibody (Jackson ImmunoResearch Laboratory, West Grove, Pa.) diluted 1:10,000 in Antibody Dilution Buffer and the plates placed on a slowly rotating platform for 1 hour at room temperature. Wells were then washed four times with 200 μL/well PBS/ 0.1% Tween-20, including slow rotation for minutes for the third wash and 10 minutes for the final wash. The wells were then washed once with 200 μL PBS without Tween-20. To each well was then added 100 μL of TMB solution (Sigma, St. Louis, Mo.) followed by incubation at room temperature for 8 minutes and then the addition of 100 μL/well of 3% v/v phosphoric acid (Sigma, St. Louis, Mo.). Absorbance was determined at a 450 nm wavelength using a spectrophotometer (Molecular Devices SpectraMax 250).

In Vivo Assays

Example A

Mouse In Vivo TNFα-Induced Kidney and Liver Phospho-c-Jun Assay

Male C57/BL6 mice were obtained from Jackson Labs and acclimatized for at least one week prior to use at age 10-12 weeks. Mice (n=8 per group) were administered Compound I-1 (Group 3; 50 mg/kg from a 12.5 mg/mL preparation in 20% (v/v)DMSO/80% (v/v) PEG400) or vehicle alone (Groups 1 and 2) via oral gavage. One hour later, mice received an intravenous challenge of 5 μg/kg recombinant mouse TNFα (Sigma) in saline (Groups 2 and 3) or saline alone (Group 1). After a further 1 h, the animals were killed by carbon dioxide inhalation. Kidneys and livers were removed, rapidly frozen in liquid nitrogen and stored at −80 degrees until analysis.

For analysis of kidneys, whole frozen organs were added to a denaturing electrophoresis buffer (1×LDS sample buffer (Invitrogen) supplemented with 1× sample reducing agent (Invitrogen) and 25 mM sodium pyrophosphate (Sigma) at room temperature and homogenized for approximately 5 seconds using a Polytron Tissumizer. Portions were subjected to SDS-PAGE by conventional means. Phospho-c-jun was identified using a rabbit primary antibody directed against phospho-(Ser63)-c-jun (Epitomics) and a goat anti-rabbit secondary antibody possessing a fluorescent tag (LI-COR). Band intensity was quantified using a LI-COR Odyssey scanner and LI-COR software.

For analysis of livers, portions of frozen tissue (100-200 mg) were homogenized in lysis buffer (Cell Signaling Technology) supplemented with 1% (v/v) of each of Phosphatase Inhibitor Cocktail-1 (Sigma), Phosphatase Inhibitor Cocktail-2 (Sigma), Protease Inhibitor Cocktail (Sigma) and 1 mM AEBSF (Sigma). The phospho-(Ser63)-c-jun content was quantified using an ELISA kit (Cell Signaling Technology).

The results, normalized to the Group 2 value as 100%, are shown in Table III, below.

TABLE III

| Group | Treatment | Kidney phospho-c-jun | Liver phospho-c-jun |
|---|---|---|---|
| 1 | no compound, no TNFα | 21.3 (15.3) | 4.5 (2.1) |
| 2 | no compound, TNFα | 100 (15.4) | 100 (16.1) |
| 3 | Compound I-1, TNFα | 29.5* (10.1) | 33.2* (9.1) |

(mean +/− standard deviation;
*indicates significant difference between Groups 2 and 3, $p < 0.05$)

Example B

Mouse In Vivo TNFα-Induced Kidney and Liver Phospho-c-Jun Assay

Experimental procedures were identical to Example A, but using 7-chloro-3-(4-methanesulfonyl-benzyl)-4-oxo-1-phenyl-1,4-dihydro-quinoline-2-carboxylic acid methyl ester. No significant effect of the compound was found on the levels of phospho-(Ser63)-c-jun in the livers or kidneys of the mice.

Example C

Rat In Vivo TNFα-Induced Kidney Phospho-c-Jun Assay

Male Sprague-Dawley rats were obtained from Charles River and acclimatized for at least one week prior to use at age 6-8 weeks. Rats (n=8 per group) were administered Compound I-1 (Group 3; 75 mg/kg from a Microprecipitated Bulk Powder formulation resuspended in Klucel vehicle at 18.75 mg/mL) or vehicle alone (Groups 1 and 2) via oral gavage. Seven hours later, rats received an intravenous challenge of 2.5 μg/kg recombinant rat TNFα (Sigma) in saline (Groups 2 and 3) or saline alone (Group 1). After a further 1 h, the animals were killed by carbon dioxide inhalation. Kidneys were removed, rapidly frozen in liquid nitrogen and stored at −80 degrees until analysis.

Sample analysis was performed as described for mouse kidneys in Example a.

The results, normalized to the Group 2 value as 100%, are shown in Table IV, below.

TABLE IV

| Group | Treatment | Kidney phospho-c-jun |
|---|---|---|
| 1 | no compound, no TNFα | 24.3 (6.0) |
| 2 | no compound, TNFα | 100 (38.6) |
| 3 | Compound I-1, TNFα | 51.8* (41.1) |

(mean +/− standard deviation;

*indicates significant difference between Groups 2 and 3, p < 0.05)

Example D

Rat In Vivo TNFα-Induced Kidney Phospho-c-Jun Assay

Male Sprague-Dawley rats were obtained from Charles River and acclimatized for at least one week prior to use at age 6-8 weeks. Rats (n=8 per group) were administered Compound I-1 (Groups 3 and 4; 75 mg/kg from a Microprecipitated Bulk Powder formulation resuspended in Klucel vehicle at 18.75 mg/mL) or vehicle alone (Groups 1 and 2) via oral gavage. Group 3 received an additional identical dose 12 hours later. Group 4 received an additional identical dose at 8 and 16 hours after the first dose. Twenty-three hours following the initial dosing, rats received an intravenous challenge of 2.5 ug/kg recombinant rat TNFα (Sigma) in saline (Groups 2, 3 and 4) or saline alone (Group 1). After a further 1 h, the animals were killed by carbon dioxide inhalation. Kidneys were removed, rapidly frozen in liquid nitrogen and stored at −80 degrees until analysis.

Sample analysis was performed as described for mouse kidneys in Example A.

The results, normalized to the Group 2 value as 100%, are shown in Table V, below.

TABLE V

| Group | Treatment | Kidney phospho-c-jun |
|---|---|---|
| 1 | no compound, no TNFα | 12.0 (5.0) |
| 2 | no compound, TNFα | 100 (36.8) |
| 3 | Compound I-1 (2 doses), TNFα | 59.6 (30.0) |
| 4 | Compound I-1 (3 doses), TNFα | 52.3* (21.5) |

(mean +/− standard deviation;

*indicates significant difference between Groups 2 and 4, p < 0.05)

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

We claim:
1. A compound of formula I

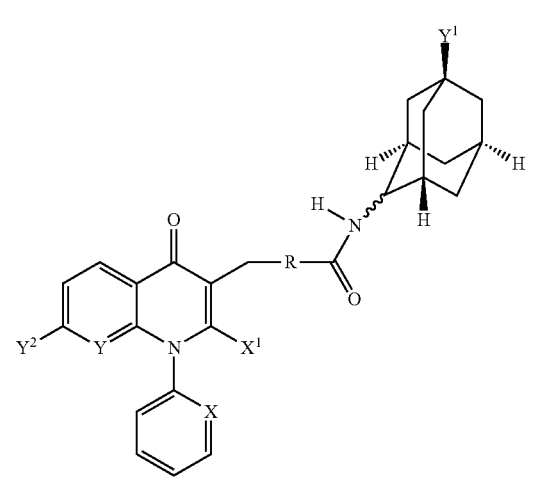

wherein:
R is phenyl, or pyridonyl, optionally substituted with one or more R';
R' is halo or methoxy;
X is CH or N;
$X^1$ is H or $C(=O)OCH_3$ or 2-oxazole;
Y is CH or N;
$Y^1$ is OH, $OC(=O)Y^{1'}$, $N(Y^{1'})_2$, $NHS(=O)_2Y^{1'}$, $NHC(=O)Y^{1'}$, $NHC(=O)C(CH_3)_2OH$, $NHCH_2C(CH_3)_2OH$, or $NHC(=O)C(CH_3)_2C(=O)Y^{1'}$;
each $Y^{1'}$ is independently H, lower alkyl, lower hydroxyalkyl, or cycloalkyl;
$Y^2$ is H, halo, or haloalkyl;
or a pharmaceutically acceptable salt thereof.

2. The compound of claim 1, wherein X is CH, and $X^1$ is $C(=O)OCH_3$.

3. The compound of claim 2, wherein R is phenyl.

4. The compound of claim 3, wherein Y is CH and $Y^2$ is Cl.

5. The compound of claim 3, wherein Y is N and $Y^2$ is H.

6. The compound of claim 3, wherein $Y^1$ is OH or $OC(=O)Y^{1'}$.

7. The compound of claim 3, wherein $Y^1$ is $NH_2$.

8. The compound of claim 3, wherein $Y^1$ is $NHS(=O)_2Y^{1'}$.

9. The compound of claim 3, wherein $Y^1$ is $NHC(=O)Y^{1'}$.

10. The compound of claim 3, wherein $Y^1$ is $NHC(=O)C(CH_3)_2C(=O)CH_3$.

11. The compound of claim 3, wherein $Y^1$ is $NHC(=O)C(CH_3)_2OH$.

12. The compound of claim 3, wherein $Y^1$ is $NHC(=O)CH_3$.

13. The compound of claim 3, wherein $Y^1$ is $NHC(=O)C(CH_3)_3$.

14. A compound selected from the group consisting of:
rel-3-[4-((1S,2S,3R,5S,7S)-5-Hydroxy-adamantan-2-yl-carbamoyl)-benzyl]-4-oxo-1-phenyl-1,4-dihydro-[1,8]naphthyridine-2-carboxylic acid methyl ester;
rel-3-[4-((1S,2R,3R,5S,7S)-5-Hydroxy-adamantan-2-yl-carbamoyl)-benzyl]-4-oxo-1-phenyl-1,4-dihydro-[1,8]naphthyridine-2-carboxylic acid methyl ester;
rel-7-Chloro-3-[4-((1S,2S,3R,5S,7S)-5-hydroxy-adamantan-2-ylcarbamoyl)-benzyl]-4-oxo-1-phenyl-1,4-dihydro-quinoline-2-carboxylic acid methyl ester;

rel-7-Chloro-3-[4-((1S,2R,3R,5S,7S)-5-hydroxy-adamantan-2-ylcarbamoyl)-benzyl]-4-oxo-1-phenyl-1,4-dihydro-quinoline-2-carboxylic acid methyl ester;

rel-4-(7-Chloro-4-oxo-1-pyridin-2-yl-1,4-dihydro-quinolin-3-ylmethyl)-N-((1S,2S,3R,5S,7S)-5-hydroxy-adamantan-2-yl)-benzamide;

rel-3-[4-((1S,2S,3R,5S,7S)-5-Acetoxy-adamantan-2-ylcarbamoyl)-benzyl]-7-chloro-4-oxo-1-phenyl-1,4-dihydro-quinoline-2-carboxylic acid methyl ester;

rel-3-[4-((1S,2S,3R,5S,7S)-5-amino-adamantan-2-ylcarbamoyl)-benzyl]-4-oxo-1-phenyl-1,4-dihydro-[1,8]naphthyridine-2-carboxylic acid methyl ester;

rel-3-[4-((1S,2R,3R,5S,7S)-5-amino-adamantan-2-ylcarbamoyl)-benzyl]-4-oxo-1-phenyl-1,4-dihydro-[1,8]naphthyridine-2-carboxylic acid methyl ester;

rel-3-[4-((1S,2S,3R,5S,7S)-5-Amino-adamantan-2-ylcarbamoyl)-benzyl]-7-chloro-4-oxo-1-phenyl-1,4-dihydro-quinoline-2-carboxylic acid methyl ester;

rel-3-[4-((1S,2S,3R,5S,7S)-5-Acetylamino-adamantan-2-ylcarbamoyl)-benzyl]-7-chloro-4-oxo-1-phenyl-1,4-dihydro-quinoline-2-carboxylic acid methyl ester;

rel-7-Chloro-3-{4-[(1S,2S,3R,5S,7S)-5-(2,2-dimethyl-propionylamino)-adamantan-2-ylcarbamoyl]-benzyl}-4-oxo-1-phenyl-1,4-dihydro-quinoline-2-carboxylic acid methyl ester;

rel-3-{4-[(1S,2S,3R,5S,7S)-5-(2-Acetoxy-2-methyl-propionylamino)-adamantan-2-ylcarbamoyl]-benzyl}-7-chloro-4-oxo-1-phenyl-1,4-dihydro-quinoline-2-carboxylic acid methyl ester;

rel-7-Chloro-3-{4-[(1S,2S,3R,5S,7S)-5-(2-hydroxy-2-methyl-propionylamino)-adamantan-2-ylcarbamoyl]-benzyl}-4-oxo-1-phenyl-1,4-dihydro-quinoline-2-carboxylic acid methyl ester;

rel-7-Chloro-3-{4-[(1S,2S,3R,5S,7S)-5-cyclopropanesulfonylamino-adamantan-2-ylcarbamoyl]-benzyl}-4-oxo-1-phenyl-1,4-dihydro-quinoline-2-carboxylic acid methyl ester;

rel-7-Chloro-3-{4-[(1S,2S,3R,5S,7S)-5-methanesulfonylamino-adamantan-2-ylcarbamoyl]-benzyl}-4-oxo-1-phenyl-1,4-dihydro-quinoline-2-carboxylic acid methyl ester;

rel-7-Chloro-3-{4-[(1S,2S,3R,5S,7S)-5-(2-hydroxy-2-methyl-propylamino)-adamantan-2-ylcarbamoyl]-benzyl}-4-oxo-1-phenyl-1,4-dihydro-quinoline-2-carboxylic acid methyl ester;

rel-3-[4-((1S,2S,3R,5S,7S)-5-Acetylamino-adamantan-2-ylcarbamoyl)-benzyl]-4-oxo-1-phenyl-1,4-dihydro-[1,8]naphthyridine-2-carboxylic acid methyl ester;

rel-3-[4-((1S,2S,3R,5S,7S)-5-Cyclopropanesulfonylamino-adamantan-2-ylcarbamoyl)-benzyl]-4-oxo-1-phenyl-1,4-dihydro-[1, 8]naphthyridine-2-carboxylic acid methyl ester;

rel-3-[4-((1S,2S,3R,5S,7S)-5-Methanesulfonylamino-adamantan-2-ylcarbamoyl)-benzyl]-4-oxo-1-phenyl-1,4-dihydro-[1,8]naphthyridine-2-carboxylic acid methyl ester;

rel-3-{4-[(1S,2S,3R,5S,7S)-5-(2,2-Dimethyl-propionylamino)-adamantan-2-ylcarbamoyl]-benzyl}-4-oxo-1-phenyl-1,4-dihydro-[1, 8]naphthyridine-2-carboxylic acid methyl ester;

rel-3-{4-[(1S,2S,3R,5S,7S)-5-(2-Acetoxy-2-methyl-propionylamino)-adamantan-2-ylcarbamoyl]-benzyl}-4-oxo-1-phenyl-1,4-dihydro-[1, 8]naphthyridine-2-carboxylic acid methyl ester;

rel-3-{4-[(1S,2S,3R,5S,7S)-5-(2-Hydroxy-2-methyl-propionylamino)-adamantan-2-ylcarbamoyl]-benzyl}-4-oxo-1-phenyl-1,4-dihydro-[1, 8]naphthyridine-2-carboxylic acid methyl;

rel-3-[4-((1S,2S,3R,5S,7S)-5-Hydroxy-adamantan-2-ylcarbamoyl)-2-methoxy-benzyl]-4-oxo-1-phenyl-1,4-dihydro-[1, 8]naphthyridine-2-carboxylic acid methyl ester;

rel-3-[2-Fluoro-4-((1S,2S,3R,5S,7S)-5-hydroxy-adamantan-2-ylcarbamoyl)-benzyl]-4-oxo-1-phenyl-1,4-dihydro-[1, 8]naphthyridine-2-carboxylic acid methyl ester;

rel-3-[4-((1S,2S,3R,5S,7S)-5-Hydroxy-adamantan-2-ylcarbamoyl)-benzyl]-4-oxo-1-phenyl-7-trifluoromethyl-1,4-dihydro-[1,8]naphthyridine-2-carboxylic acid methyl ester;

rel-7-Chloro-3-[4-((1S,2S,3R,5S,7S)-5-hydroxy-adamantan-2-ylcarbamoyl)-2-oxo-2H-pyridin-1-ylmethyl]-4-oxo-1-phenyl-1,4-dihydro-quinoline-2-carboxylic acid methyl ester; and Rel-4-(7-Chloro-2-oxazol-2-yl-4-oxo-1-phenyl-1,4-dihydro-quinolin-3-ylmeth yl)-N-((1S,2S,3R,5S,7S)-5-hydroxy-adamantan-2-yl)-benzamide.

15. A pharmaceutical composition comprising the compound of claim 1, admixed with at least one pharmaceutically acceptable carrier, excipient or diluent.

* * * * *